(12) United States Patent
Grinstaff et al.

(10) Patent No.: US 10,821,204 B2
(45) Date of Patent: Nov. 3, 2020

(54) INJECTABLE TISSUE SUPPLEMENT

(71) Applicant: TRUSTEES OF BOSTON UNIVERSITY, Boston, MA (US)

(72) Inventors: Mark Grinstaff, Brookline, MA (US); Benjamin Goldman Cooper, Brookline, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 22 days.

(21) Appl. No.: 15/840,302

(22) Filed: Dec. 13, 2017

(65) Prior Publication Data

US 2018/0099072 A1 Apr. 12, 2018

Related U.S. Application Data

(63) Continuation of application No. 15/159,184, filed on May 19, 2016, now Pat. No. 9,872,936, which is a continuation of application No. PCT/US2014/066584, filed on Nov. 20, 2014.

(60) Provisional application No. 61/906,689, filed on Nov. 20, 2013.

(51) Int. Cl.
| | |
|---|---|
| *A61L 27/18* | (2006.01) |
| *A61L 27/50* | (2006.01) |
| *A61L 27/54* | (2006.01) |
| *C08L 43/02* | (2006.01) |
| *C08F 220/28* | (2006.01) |
| *C08F 230/02* | (2006.01) |
| *A61L 27/52* | (2006.01) |
| *A61K 9/06* | (2006.01) |

(52) U.S. Cl.
CPC .............. *A61L 27/18* (2013.01); *A61L 27/50* (2013.01); *A61L 27/52* (2013.01); *A61L 27/54* (2013.01); *C08F 220/28* (2013.01); *C08F 230/02* (2013.01); *C08L 43/02* (2013.01); *A61K 9/06* (2013.01); *A61L 2400/06* (2013.01); *A61L 2400/10* (2013.01); *A61L 2430/06* (2013.01); *A61L 2430/34* (2013.01)

(58) Field of Classification Search
CPC .......... A61L 27/18; A61L 27/50; A61L 27/54; A61L 2430/00–40; C08F 220/28; C08F 230/02; C08L 43/02
See application file for complete search history.

(56) References Cited

U.S. PATENT DOCUMENTS

| | | | |
|---|---|---|---|
| 5,854,030 | A | 12/1998 | Dordick et al. |
| 6,224,893 | B1 | 5/2001 | Langer et al. |
| 6,562,330 | B1 | 5/2003 | Stratford et al. |
| 7,625,580 | B1 | 12/2009 | Langer et al. |
| 7,897,165 | B2 | 3/2011 | Elisseeff et al. |
| 8,378,064 | B2 | 2/2013 | Grinstaff et al. |
| 2007/0196454 | A1 | 8/2007 | Stockman et al. |
| 2008/0312156 | A1 | 12/2008 | Setton et al. |
| 2008/0317818 | A1 | 12/2008 | Griffith et al. |
| 2009/0117070 | A1 | 5/2009 | Daniloff et al. |
| 2009/0324722 | A1 | 12/2009 | Elisseeff |
| 2010/0227077 | A1 | 9/2010 | Wen et al. |
| 2011/0124819 | A1 | 5/2011 | Hoelzl et al. |
| 2011/0294189 | A1 | 12/2011 | Chilkoti et al. |
| 2012/0207847 | A1 | 8/2012 | Butler et al. |

FOREIGN PATENT DOCUMENTS

| | | |
|---|---|---|
| EP | 1095665 A1 | 5/2001 |
| EP | 1987849 A1 | 5/2008 |
| EP | 2457539 A1 | 5/2012 |
| JP | 2011-080187 A | 3/1999 |
| JP | 2001-142034 A | 5/2001 |
| JP | 2005-008607 A | 1/2005 |
| JP | 2012-071590 A | 4/2012 |
| WO | 2000001424 A1 | 1/2000 |
| WO | 2005092406 A1 | 3/2005 |
| WO | 2013047395 A1 | 4/2013 |

OTHER PUBLICATIONS

Kiritoshi (Kiritoshi, Y., et al., Preparation of cross-linked biocompatible poly(2-methacryloyloxyethyl phosphorylcholine) gel and its strange swelling behavior in water/ ethanol mixture, J. Biomater. Sci. Polymer Edn, vol. 13, No. 2, pp. 213-224 (2002)).*
Arnold et al., "Evaluation of resorbable baniers for preventing surgical adhesions", Fertility and Sterility 73 (1):157-161 (2000).
Ateshian G., "The role of interstitial fluid pressurization in articular cartilage lubrication", Journal of Biomechanics 42:1163-1176 (2009).
Bai et al., "Construction of an ultrahigh strength hydrogel with excellent fatigue resistance based on strong dipole—dipole interaction", Soft Matter 7:2825-2831 (2011).
Carnahan et al., "Hybrid Dendritic-Linear Polyester-Ethers for in Situ Photopolymerization", Journal of the American Chemical Society 124(19):5291-5293 (2002).
Degoricija et al., "Photo Cross-linkable Biodendrimers as Ophthalmic Adhesives for Central Lacerations and Penetrating Keratoplasties", Investigative Ophthalmology & Visual Science 48(5):2037-2042 (2007).
Degoricija et al., "Hydrogels for Osteochondral Repair Based on Photocrosslinkable Carbamate Dendrimers", Biomacromolecules 9(10):2863-2872 (2008).

(Continued)

*Primary Examiner* — H. Sarah Park
(74) *Attorney, Agent, or Firm* — Nixon Peabody LLP; Ronald I. Eisenstein; Ravinderjit Braich

(57) ABSTRACT

The present invention provides polymers which can be used as tissue supplements or lubricants in vivo. The inventive polymers can be used as tissue-interpenetrating hydrogel supplements, viscosupplements, tribosupplements, viscoelastics, tissue space fillers, and/or anti-adhesive agents. Also provided are pharmaceutical compositions comprising the inventive polymers and methods of using them including, for example, in the treatment of arthritic and injured synovial joints; in reconstruction or cosmetic procedures, intervertebral disc repair, treatment of vocal cord problems, treatment of urinary incontinence, and prevention of adhesion formation following abdominal or gynecological surgery or malfunction of naturally lubricious mucosal tissue.

5 Claims, 22 Drawing Sheets

(56) References Cited

OTHER PUBLICATIONS

Elisseeff et al., "Transdermal photopolymerization for minimally invasive implantation", Proceedings of the National Academy of Sciences 96:3104-3107(1999).
Grinstaff M., "Dendritic Macromers for Hydrogel Formation: Tailored Materials for Ophthalmic, Orthopedic, and Biotech Applications", Journal of Polymer Science Part A: Polymer Chemistry 46:383-400 (2008).
Herrick et al., "PEG-Phosphorylcholine Hydrogels as Tunable and Versatile Platforms for Mechanobiology", Biomacromolecules 14:2294-2304 (2013).
Ibusuki et al., "Tissue-Engineered Cartilage Using an Injectable and in Situ Gelable Thermoresponsive Gelatin: Fabrication and in Vitro Performance", Tissue Engineering 9(2):371-384 (2003).
Klein J., "Polymers in living systems: from biological lubrication to tissue engineering and biomedical devices", Polymers for Advanced Technologies 23:729-735 (2012).
Kon et al., "How to Treat Osteochondritis Dissecans of the Knee: Surgical Techniques and New Trends", The Journal of Bone and Joint Surgery 94(1):e1(1-8) (2012).
Liu et al., "Collagen—phosphorylcholine interpenetrating network hydrogels as corneal substitutes", Biomaterials 30:1551-1559 (2009).
Nettles et al., "Photocrosslinkable Hyaluronan as a Scaffold for Articular Cartilage Repair", Annals of Biomedical Engineering 32(3):391-397 (2004).
Sontjens et al., "Biodendrimer-Based Hydrogel Scaffolds for Cartilage Tissue Repair", Biomacromolecules 7:310-316 (2006).
Steadman et al., "Outcomes of Microfracture for Traumatic Chondral Defects of the Knee: Average 11-Year Follow-up", Arthroscopy: The Journal of Arthroscopic and Related Surgery 19(5):477-484 (2003).
Wang et al., "Enhancing the Tissue-Biomaterial Interface: Tissue-Initiated Integration of Biomaterials", Advanced unctional Materials 14(12):1152-1159 (2004).
Wang et al., "Multifunctional chondroitin sulphate for cartilage tissue—biomaterial integration", Nature Materials 6:385-392 (2007).
Wathier et al., "A Large-Molecular-Weight Polyanion, Synthesized via Ring-Opening Metathesis Polymerization, as a Lubricant for Human Articular Cartilage", Journal of the American Chemical Society 135:4930-4933 (2013).

\* cited by examiner

Resistance of hydrogel-treated tissue to enzymatic digestion: Native cartilage digested by papain within several hours, while hydrogel-treated cartilage resists digestion over 1 week

INJECTABLE TISSUE SUPPLEMENT

CROSS-REFERENCE TO RELATED APPLICATION

This application is a continuation application of U.S. patent application Ser. No. 15/159,184, filed May 19, 2016, which is a continuation of International Patent Application No. PCT/US2014/066584 filed on Nov. 20, 2014, which claims priority to and benefit under 35 U.S.C. § 119(e) of U.S. Provisional Application No. 61/906,689 filed Nov. 20, 2013, the contents of all of which are incorporated herein by reference in their entirety.

GOVERNMENT SUPPORT

This invention was made with government support under grant No. DGE-1247312 awarded by the National Science Foundation. The government has certain rights in the invention.

TECHNICAL FIELD

The present disclosure relates generally to compositions and methods for treating diseased, injured, suboptimal or defective tissue. More specifically, the present invention relates to polymeric tissue supplements, uses of the same, and methods of making the same.

BACKGROUND

Osteoarthritis (OA), a non-inflammatory joint disease characterized by degeneration of joint cartilage, can affect one or more parts of the body, including hands and weight-bearing joints such as knees, hips, feet and the spine. When healthy, cartilage allows bones to glide over each other and has a shock absorbing function. In osteoarthritis, the cartilage breaks down and wears away, which eventually allows the bones under the cartilage to rub together, causing the common OA symptoms of pain, swelling, and loss of motion of the joint. Furthermore, in joints such as the knees, osteoarthritis is often accompanied by loss of viscosity of the synovial fluid, a thick, gel-like substance that cushions the joint and provides lubrication to reduce friction of the bones.

Prior to the disease advancement stage of bone-on-bone contact, a significant hallmark of OA is the loss of glycosaminoglycan (GAG), a polysaccharide that contains many negative charges and thus causes many water molecules to be withheld and immobilized within the cartilage tissue. The water molecules play a significant role in the mechanical properties of cartilage, imparting the ability of the tissue to bear compressive loads. This is an effect of the tissue being biphasic, i.e. being composed of a solid component and a fluid component; during loading of healthy cartilage, the load is initially borne mostly by the fluid component, which has ramifications both in compression properties and consequently for lubrication, as the load being borne mainly by the fluid component of the tissue allows less load to be borne by the solid components, thereby minimizing the frictional force on the solid components.

As GAG depletes during the progression of OA, the tissue withholds water molecules less effectively. Hydraulic permeability increases, allowing water to flow out of the tissue under loading faster than it would if the tissue were not osteoarthritic. As a result, compressive moduli and tau values (time to stress equilibration under strain-controlled loading or time to strain equilibration under stress-controlled loading) of osteoarthritic cartilage are typically lower than those of healthy cartilage, and coefficient of friction of osteoarthritic cartilage is typically greater than that of healthy cartilage. In addition, osteoarthritic cartilage typically exhibits regions with significant variability in compressive strength. From a mechanics standpoint, adjacent regions of a single tissue having disparate compressive strength often exacerbates tissue deterioration under loading compared to a tissue with homogeneous compressive strength throughout the tissue's entirety.

Osteoarthritis is mainly associated with aging, with a prevalence of approximately 80% in individuals over 65. Despite being a condition that causes most problems to populations after retirement age, osteoarthritis is also rated the highest cause of work loss in the U.S. and Europe. In addition to age, risk factors known to be associated with osteoarthritis include obesity, traumatic injury and overuse due to sports and occupational stresses.

There is currently no cure for osteoarthritis, and available arthritis therapies are directed at the symptomatic relief of pain, and at improving, or at least maintaining, joint function. Generally, pain relievers such as non-steroidal anti-inflammatory drugs (NSAIDs) or COX-2 inhibitors are used, along with physical therapy. However, in the context of the recent withdrawals of COX-2 inhibitors, physicians are even more limited in their choice of treatment for osteoarthritis.

Viscosupplementation, a procedure involving the injection of gel-like substances (generally hyaluronates, also known as hyaluronic acids) into the joint to supplement the viscous properties of synovial fluid, has been shown to relieve pain in many osteoarthritis patients who do not get relief from analgesic drugs. The technique has been used in Europe and Asia for several decades, but the U.S. Food and Drug Administration did not approve it until 1997. In current procedures of viscosupplementation, hyaluronate preparations are injected to replace or supplement the body's natural hyaluronan, a polysaccharide component of synovial fluid. The injections coat the articular cartilage surface, and thus provide a possible prophylactic barrier for the articular cartilage in addition to increasing the viscosity of the synovial fluid. However, due to their short lifetime within the joint (about a couple of days), hyaluronate preparations currently available have only limited long-term benefit to the patient and require injection of large quantities of the preparation and/or repeated injections.

In an effort to combat the loss of GAGs during OA, GAGs may be taken orally as supplements (chondroitin sulfate, glucosamine, and other saccharide-based supplements), and are also applied as topical creams. However, these molecules do not enter the bulk of the cartilage and remain there for long durations, and their direct effect of integrating within the tissue is transient. An alternate hypothesis purports that the GAGs are not directly incorporated into the solid matrix of the tissue but rather are used as building blocks by chondrocytes to produce new GAG through natural synthesis. While this hypothesis stands to be further tested, it should be noted that chondrocyte production of GAG is downregulated during OA, and introducing excess supplementary GAG does not necessarily equate with increased incorporation of GAG into the cartilage extracellular matrix.

Accordingly, there is a strong need in the art for compositions and methods to treat, repair or supplement tissues.

SUMMARY

The present disclosure provides compositions (e.g., polymer compositions), their method of use, and their method of production. One factor for the inventive polymer's utility is its hydrophilicity, which can be imparted by hydrophilic monomers incorporated into the polymer's chemical structure.

In some embodiments, a monomer incorporated into the polymer comprises a chemical functionality selected from the group consisting of carboxylic acid, carboxylate, sulfate, sulfonate, sulfuric acid, phosphate, phosphonate, phosphoric acid, amine, ammonium, phosphine, phosphonium, ether, and any combinations thereof. Without limitations, the monomer can be charged (i.e., a negative or positive charge) or uncharged. In some embodiments, the monomer is a charged monomer. In some embodiments, the monomer can be zwitterionic monomer (i.e., a monomer with both a positive and a negative charge).

One aspect of the inventive concept is the formation of a semi-natural and semi-synthetic interpenetrating network (IPN) composition by laparoscopic treatment of degenerative or defective tissue in a living animal. Generally, a composition, e.g., a solution, comprising monomers is first allowed to permeate into the tissue, followed by in situ polymerization of the monomers to form the polymer. This method creates a novel type of interpenetrating network (IPN), also known as a double network, in which one network is the newly polymerized hydrogel or polymer and the other network is the animal's natural tissue. While IPNs of a semi-synthetic and semi-natural nature have been reported previously, all prior examples teach either a) integration of the synthetic network at the surface of the biological tissue—not throughout its entirety, or b) combination of the two networks outside the body (e.g. ex vivo collagen with a synthetic hydrogel)—not in vivo. However, in the compositions and methods disclosed herein, the monomers can polymerize into a hydrogel or polymer that is tangled with the natural components of the tissue. This provides a robust integration that can trap the polymerized monomers (e.g., hydrogel or polymer) in place.

In one embodiment, a solution of monomers and photoinitiators are first allowed to permeate into the tissue, followed by in situ photopolymerization with light through a minimally invasive flexible fiberoptic cable. The light emits radially or non-radially from the device to expose the tissue containing the monomer solution. The monomers polymerize upon exposure to visible light into a hydrogel or polymer that is entangled with the natural components of the animal's tissue, causing a robust integration that traps the hydrogel or polymer in place.

The tissue-polymer IPN is, among other things, designed to improve mechanical properties of the degenerative state of the tissue in order to recapitulate the healthy state of the tissue. Alternatively, the IPN can be formed to change the mechanical properties to any parameter so desired by the practitioner, e.g., a treating medical professional. Mechanical properties, such as compressive modulus, lubrication, prevention of wear, and duration of time that the tissue is resistant to loading, can all be returned to healthy levels and thereby treat disease, or these properties can be tuned to a variety of levels determined by the treatment conditions.

In some embodiments, the IPN can be used to alter compressive mechanical properties of the tissue. For example, upon treatment of osteoarthritic cartilage, an IPN of the type described herein can function in a manner mimetic of GAG; by serving the identical role as GAG of withholding and immobilizing water molecules within the cartilage tissue, the IPN can allow for the recapitulation of mechanical properties seen in healthy cartilage. Compressive modulus can be augmented, in part due to the decrease in hydraulic permeability afforded by the presence of the water-immobilizing hydrogel in the IPN.

Tissues at different levels of health generally have different compressive strengths; the hydrogel IPN treatment described herein can treat tissues at different levels of initial compressive strength to different degrees. When soft tissue is artificially depleted of its GAG molecules to simulate a disease in which GAGs degenerate, identical IPN treatment of the degraded tissue and healthy control tissue results in a greater percent increase in compressive mechanical moduli for the degraded tissue than for the healthy tissue. This property of the hydrogel IPN treatment demonstrates that with a single treatment formulation, a tissue in more dire need of treatment can receive a greater treatment than a tissue in less need of treatment.

The mechanism by which the hydrogel impregnation of a single tissue functions, in the case of an IPN of the type described herein, relies on a systems-level treatment approach. With a single in situ polymerization, more porous regions of the tissue to be treated receive proportionally greater hydrogel content and less porous regions of the tissue to be treated receive proportionally less hydrogel content following treatment. Higher porosity generally correlates with decreased compressive strength, so by the hydrogel's preferential filling of the regions of tissue that have the least compressive strength compared to the surrounding tissue, the overall tissue is reinforced and supplemented most in the regions in most dire need of reinforcement. Thus, the IPN treatment can transform a tissue with inhomogeneous compressive strength in adjacent regions (an indicator of high likelihood of tissue failure if the tissue receives frequent compressive loading) into a tissue with homogeneous compressive strength throughout the entirety of the tissue, thus prolonging the tissue's lifetime.

As a corollary to the augmentation of compressive mechanical properties, treatment with the described IPN can also be used to increase the magnitude of the tissue's Tau value, or relaxation time during deformation. In both scenarios of stress-controlled deformation until equilibrium strain as well as strain-controlled deformation until equilibrium stress, tissue-polymer IPN relaxation time may be increased due to increased immobilization of water molecules and decreased hydraulic permeability. Furthermore, in addition to modifying times to equilibration, the equilibrium values themselves of the tissue's properties may be augmented, e.g., upon treatment, the tissue can be made able to withstand a given stress while deforming less than in the pretreated state, or the tissue can be made able to withstand a given deformation while experiencing less stress.

In some embodiments, the tissue-interpenetrating hydrogel can be formed in a location near, adjacent to, or surrounding another material of increased stiffness such as bone or an implanted device. Other exemplary stiff materials are described below. The interpenetrating hydrogel can lessen the degree of disparity in mechanical properties between the soft tissue it is interpenetrating and the nearby stiff material (e.g. bone or implanted device), thereby preventing damage to the soft tissue and/or undesired mobility of the stiff material.

In some other embodiments, the IPN can be used as a lubricant, e.g., to better lubricate a tissue. For example, upon treatment of cartilage, the tissue will contain increased content of water molecules, and the immobilized water molecules will bear a significant fraction of load when the tissue is loaded via articulation. With a fraction of the load being borne by the fluid component of the tissue, the solid components of the two opposing surfaces will experience a decreased friction force, thereby providing increased lubrication. This may be manifested in a decreased coefficient of friction instantaneously or when compared over time to non-treated tissue. In addition, a surface coating of IPN (e.g., hydrogel) can exist near the articulating surface of the tissue and can act as a boundary lubricant, also providing increased lubrication specifically through boundary mode lubrication.

As a corollary to the IPN's use in improving lubrication, the treatment can also prevent wear. In a non-treated state, the solid components of tissues come into contact and their sliding is resisted by frictional forces that shear the tissue. Upon treatment, the magnitude of the frictional force on the solid components of the tissue will be decreased, thereby decreasing the wear experienced by the tissue.

In some embodiments, the tissue-hydrogel IPN can be used to decrease the diffusion or transport of harmful or otherwise undesired agents within or into a tissue of interest. For example, catabolic enzymes may be present in the synovial fluid and proximal to the articular cartilage when a traumatic injury to a nearby ligament, e.g. the ACL occurs. By formation of a cartilage-hydrogel IPN, the cartilage can thereby be protected to a certain extent from invading degradative enzymes that would otherwise cleave bonds in the tissue. Other undesired agents are described below.

In some embodiments, the hydrogel can be used as a tribosupplement without incorporation into an IPN. At low concentrations and degree of crosslinking, such hydrogels can function as effective lubricants. By application of such a tribosupplement to a diseased or injured synovial joint, mucosal tissue, or any other site of articular soft tissues that may benefit from increased lubrication, tissue wear may be decreased, along with the inflammation, pain, and potentially irreversible damage associated with such tissue wear.

The polymer backbone is less susceptible to the common modes of biomacromolecular degradation, namely, proteolytic or saccharolytic, to which many biologically derived materials are susceptible. Without wishing to be bound by theory, this can be due to the carbon-based backbone exclusively of the lubricating polymers described herein, For example, the polysaccharide hyaluronan has numerous commercial uses as a dermal filler and viscosupplement, and it is enzymatically degraded by physiological levels of the enzyme hyaluronidase. As another example, commercial collagen meshes are enzymatically degraded by physiological levels of collagenases (e.g. of the matrix metalloproteinase variety). This feature of the polymers described herein provides an extended use and the potential for greater duration of therapeutic, cosmetic, or otherwise desired effect.

DETAILED DESCRIPTION

Figure 1:
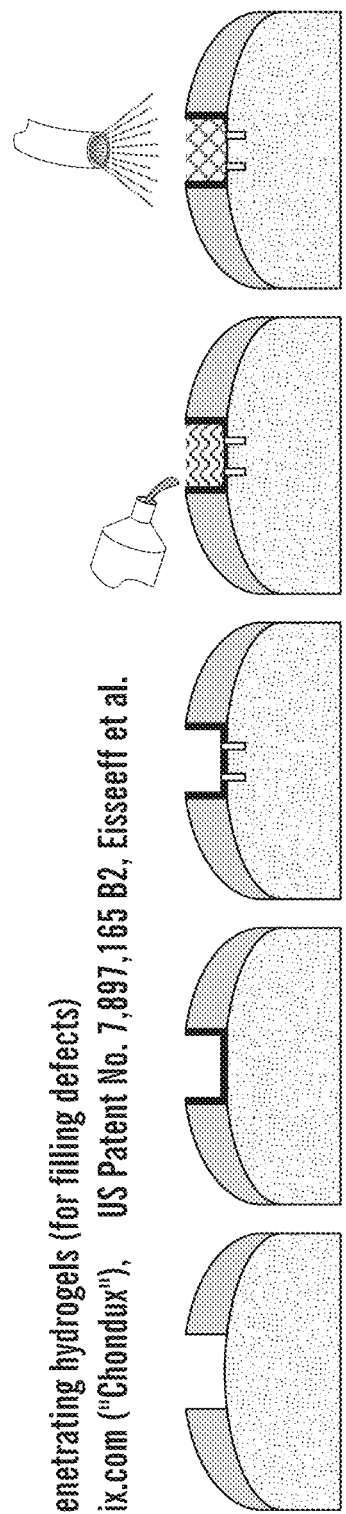
FIG. 1 is a schematic representation comparing art known compositions and methods for filling tissue defects and an embodiment of the compositions and methods disclosed herein.
Figure 1:
Figure 1:
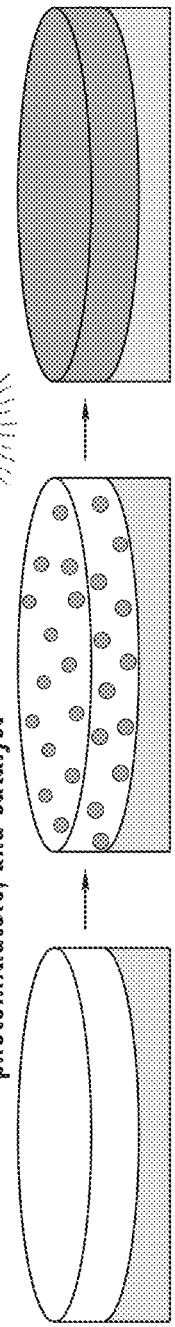
Figure 2:
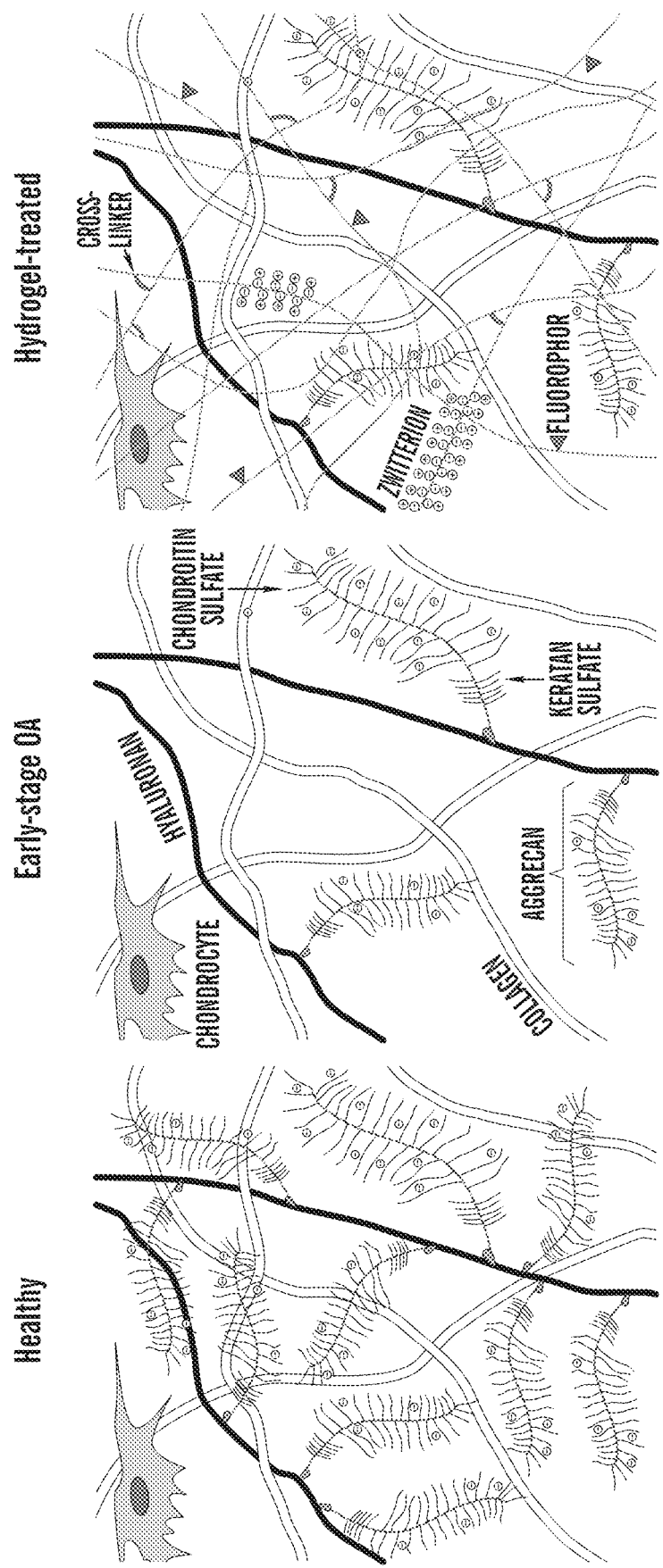
FIG. 2 is a diagram showing the structural differences between a healthy cartilage tissue, a cartilage tissue undergoing early-stage osteoarthritis, and a cartilage tissue treated by the present invention.

The field of in situ polymerization has seen much advancement over the last several decades. For example, many dental applications have involved polymerizing materials using ultraviolet light. More recently, using different photo-initiators that are tuned to be excited at different wavelengths, visible light has been used in a number of in situ polymerizations. These applications have involved shining light in an "open" setting, either directly in a nonconfined region (U.S. Pat. No. 7,897,165 B2) or from a minimally confined bodily opening such as the mouth (FIG. 1). More recently still, there has been a teaching of shining light external to the skin to irradiate molecules that have been injected subcutaneously to cause their gelation. (U.S. Pat. Nos. 6,224,893 and 7,625,580) (FIG. 1); this document further teaches irradiating the synovial space adjacent to a cartilaginous surface for the purpose of gelling a material near or in contact with the cartilage to be repaired or replaced. While the materials disclosed in that document are composed of semi-interpenetrating or interpenetrating polymer networks, the entire components of the double network are synthetic and are injected; neither one of the networks in the final double network was previously in the body prior to injection. Furthermore, in several US Patents enumerated in the present paragraph, none teach the resulting hydrogel or polymer's distribution throughout the target tissue's bulk-only local defects are filled, or substitute tissues are fabricated, but existing tissue is not supplemented or reinforced throughout its bulk (FIG. 1).

The field of interpenetrating networks (IPNs) has likewise seen much advancement recently. Many IPNs have mechanical properties that are similar to those of both "parent" networks alone (when not interpenetrating); there also exist many IPNs that feature mechanical properties that are very dissimilar from those of either of their "parent" networks alone. This situation often arises from complex interactions between the two networks and the results of combining two dissimilar networks can often be unpredictable due to these complexities.

Tribosupplements, or materials that increase lubrication, for augmenting friction at soft tissue interfaces have also seen advancements. Synovial joints and mucosa are two broad categories of animal tissue that may receive medical benefit from increased lubrication; a variety of diseases and injuries are known to cause poor lubrication at these sites. Viscosupplement compositions have been disclosed (e.g. U.S. Pat. No. 8,378,064) and are known to augment lubrication in synovial joints. Charged or zwitterionic polymers that immobilize large quantities of water molecules may act as efficient lubricants due to the abilities of withheld water to resist compressive loads and also to direct shear forces to the withheld water layer rather than to the tissue surface. In the absence of a water-immobilizing lubricant, the relatively greater compressive loads at the tissue surface would cause increased friction and thus wear, and the relatively greater shear forces at the tissue surface would cause increased friction and wear as well.

In one aspect provided herein is a polymer synthesized in situ or ex situ. Generally the polymer is a hydrophilic polymer and comprises one or more hydrophilic monomers. The hydrophilicity can be one aspect needed for the function of the polymer. For example, in the case of the inventive tissue-polymer IPN, the polymer's hydrophilicity supplements the tissue's material properties, and in the case of the inventive biolubricant, the polymer's hydrophilicity functions to lubricate the opposing tissue surfaces. Specifically for the tissue-polymer IPN, the nature of the polymer's entanglement with and within the tissue affects the material properties of the construct.

A polymer's hydrophilicity can be imparted by the chemical nature of the monomers comprising said polymer. In the case of the inventive polymers described herein, monomer hydrophilicity can be imparted by, for example, charged species, zwitterions, hydrogen bond donors, hydrogen bond acceptors, and/or other polar functional groups. Accordingly, in some embodiments, the polymer comprises a charged monomer. The charged monomer can have a positive or negative charge.

In some embodiments, the polymer comprises a monomer that is charged but has no overall net charge, e.g., the monomer is zwitterionic. In some embodiments, the polymer comprises a monomer that is a betaine. It is known in the art that betaines are neutral chemical compound with a positively charged cationic functional group such as a quaternary ammonium or phosphonium cation (generally: onium ions) which bears no hydrogen atom and with a negatively charged functional group such as a carboxylate group which may not be adjacent to the cationic site. Thus, a betaine can be a type of a zwitterion.

In some embodiments, the polymer comprises a monomer having a functional group selected from the group consisting of carboxylic acid, carboxylate, sulfate, sulfonate, sulfuric acid, phosphate, phosphonate, phosphoric acid, amine, ammonium, phosphine, phosphonium, ether, and any combinations thereof. In some embodiments, the polymer comprises a monomer comprising phosphorylcholine.

Generally, any monomer comprising a polymerizable group can be used in the compositions, polymers, and methods disclosed herein. In some embodiments, the polymerizable group is an ethylenically unsaturated polymerizable group. In some embodiments, the polymerizable group is a radically polymerizable group. Exemplary radically polymerizable groups include, but are not limited to, an acrylate group, a methacrylate group, a styrene group, an acryl amide group, a methacryl amide group, a maleate group, a fumarate group, an itaconate group, a vinyl ether group, an allyl ether group, an allyl ester group, a vinyl ester group, and the like.

In some embodiments, the polymer comprises a monomer selected from the group consisting of acrylated or methacrylated (or any ethylenically unsaturated) sugar molecules, compounds of Formula I to XIV, compounds of Formula XVII-XXX, compounds of Formula XXXI-XXXVII, or any combinations thereof. Exemplary acrylated, methacrylated, or ethylenically unsaturated sugars include, but are not limited to, allose, altrose, arabinose, deoxyribose, erythrose, fructose, fucose, fuculose, galactosamine, galactose, glucironolactone, glucosamine, glucose, glucuronic acid, glyceraldehydes, gulose, idose, lyxose, mannose, N-acetylgalactose, N-acetylglucosamine, N-acetylmuramic acid, N-acetylneuraminic acid, N-glycolylneuraminic acid, nonose (neuraminic acid), octose, pneumose, psicose, quinovose, rhamnose, ribose, ribulose, sedoheptulose, sialic acid, sorbose, sulfoquinovose, tagatose, talose, threose, xylose, xylulose, and the like. Without limitations, the sugar can be substituted with one or more substituents selected from the group consisting of sulfate, sulfate, carboxylate, phosphate, amine, acetyl, and any combinations thereof. Monomers applicable in the present invention can be found, for example, in U.S. Pat. No. 8,378,064 and US20070196454, the contents of each of which are incorporated by reference in their entireties.

Compounds of Formulas I-XIV include:

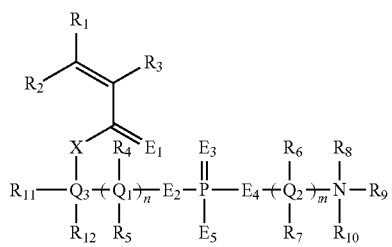

Formula I

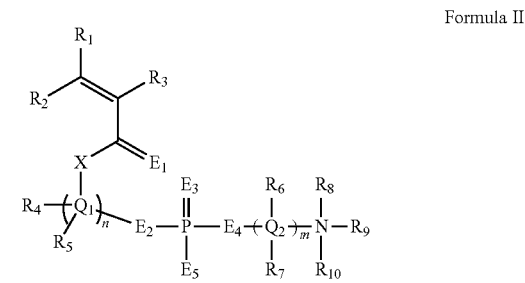

Formula II

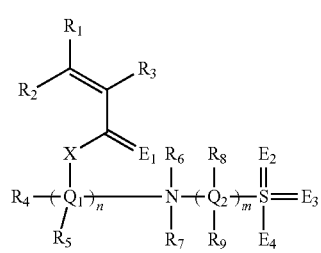

Formula III

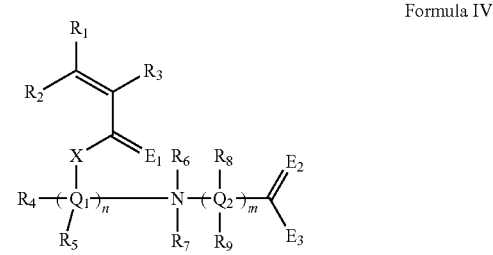

Formula IV

-continued
Formula V
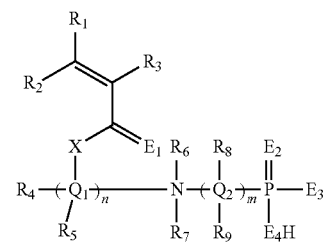
Formula VI
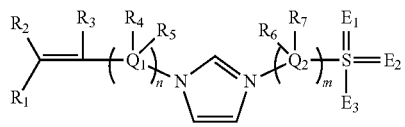
Formula VII
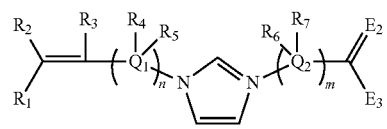
Formula VIII
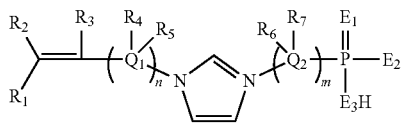
Formula IX
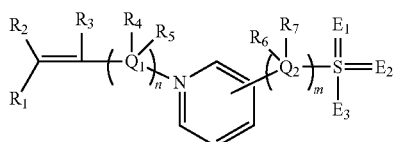
Formula X
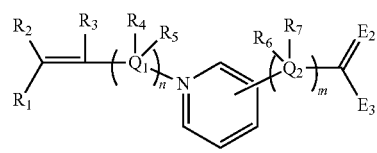
Formula XI
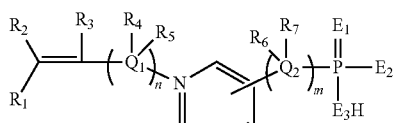
Formula XII
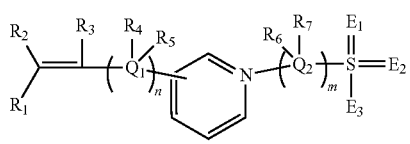
Formual XIII
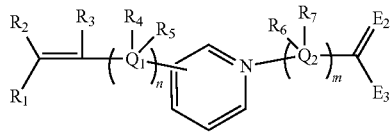
Formula XIV
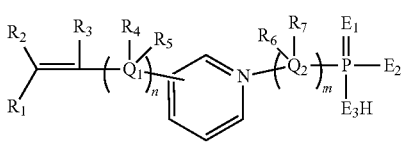
Compounds of Formula XVII-XXX include:
XVII
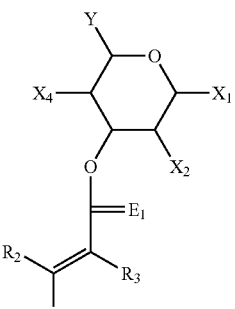
XVIII
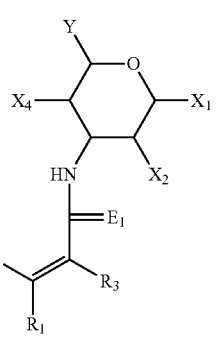
XIX
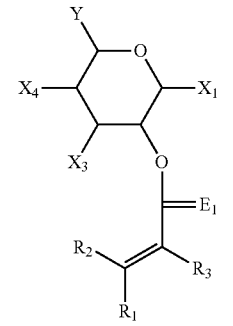
XX
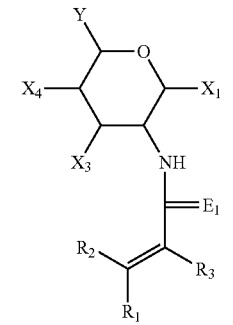

XXI 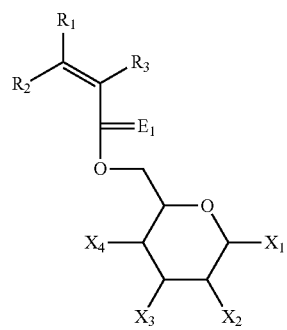
XXII 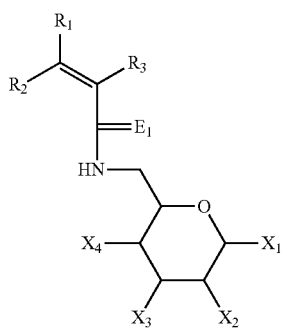
XXIII 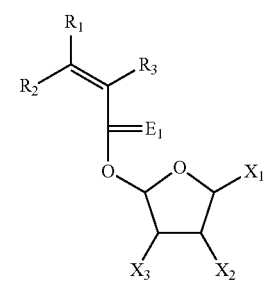
XXIV 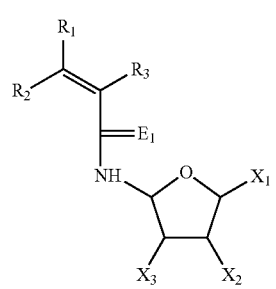
XXV 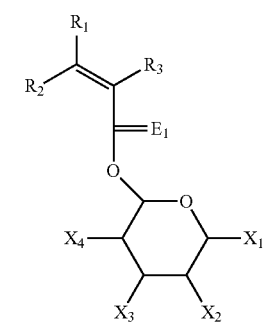
XXVI 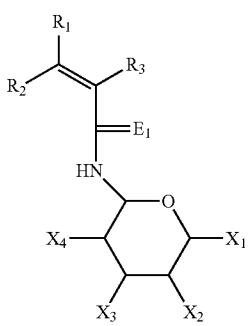
XXVII 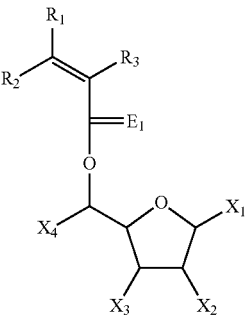
XXVIII 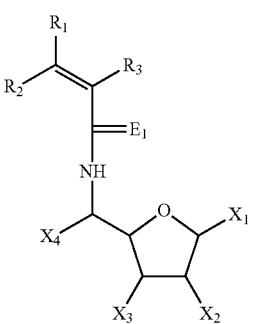
XXIX 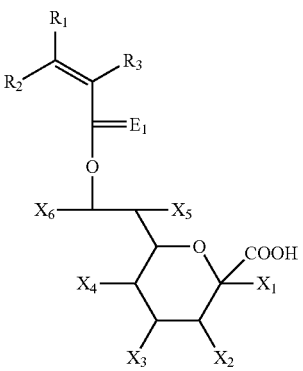

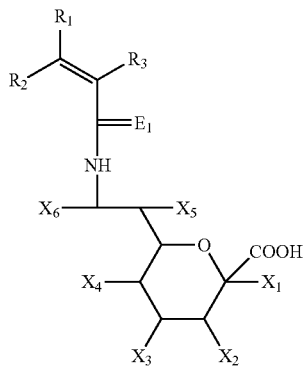

XXX

Compounds of Formula XXXI-XXXVII include:

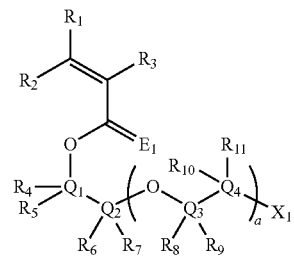

XXXI

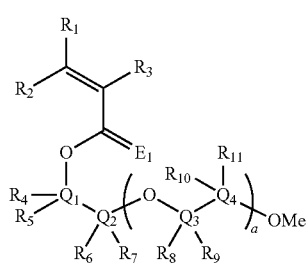

XXXII

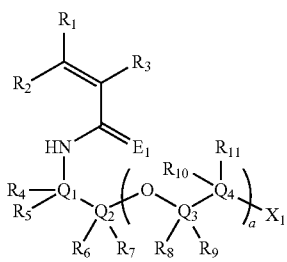

XXXIII

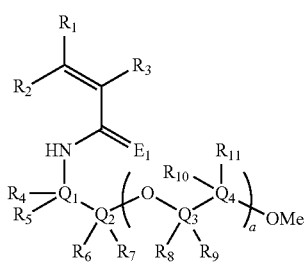

XXXIV

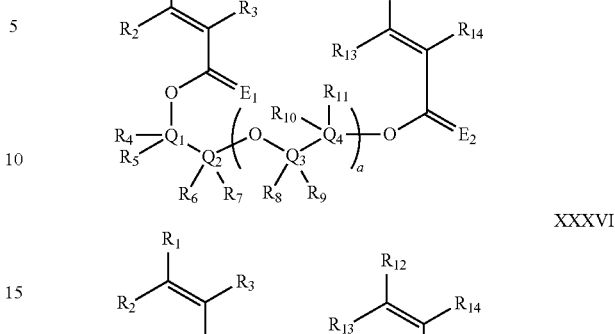

XXXV, XXXVI, XXXVII

In compounds of Formulas I-XIV and XVII-XXXVII, $R_1$, $R_2$, $R_4$, $R_5$, $R_6$, $R_7$, $R_8$, $R_9$, $R_{10}$, $R_{11}$, $R_{12}$, $R_{13}$, and $R_{14}$ are each independently selected from the group consisting of H, halide, alkyl, alkenyl, alkynyl, ether-linked alkyl, ether-linked alkenyl, ether-linked alkynyl. Some exemplary specific groups for $R_1$, $R_2$, $R_4$, $R_5$, $R_6$, $R_7$, $R_8$, $R_9$, $R_{10}$, $R_{11}$, $R_{12}$, $R_{13}$, and $R_{14}$ are H, $C_1$-$C_6$ alkyl, $C_2$-$C_6$ alkenyl, fluoro, bromo, and chloro.

In some embodiments, $R_1$, $R_2$, $R_4$, $R_5$, $R_6$, $R_7$, $R_8$, $R_9$, $R_{10}$, $R_{11}$, $R_{12}$, $R_{13}$, and $R_{14}$ can be selected independently from H or $C_1$-$C_6$ alkyl. In embodiments of compounds of formula I-XIV, $R_1$ and $R_2$ can be same or different. In some embodiments, $R_1$ and $R_2$ are both H. In some embodiments, $R_4$ and $R_5$ can be same. In some other embodiments, $R_4$ and $R_5$ are different. In some embodiments, $R_4$ and $R_5$ are both H. In compounds of formulas I-XIV, $R_6$ and $R_7$ can be same or different. In some embodiments, $R_6$ and $R_7$ are both H.

In some embodiments, $R_8$, $R_9$ and $R_{10}$ are all different. In some embodiments, only two of $R_8$, $R_9$ and $R_{10}$ are same. In some embodiments, $R_8$, $R_9$ and $R_{10}$ are all same. In some embodiments, $R_8$, $R_9$ and $R_{10}$ are all independently $C_1$-$C_6$ alkyl. In one embodiment, $R_8$, $R_9$ and $R_{10}$ are all methyl. In embodiments of compounds of formula I-XIV, $R_{11}$ and $R_{12}$ can be same or different. In some embodiments $R_{11}$ and $R_{12}$ are both H.

In compounds of Formulas I-XIV and XVII-XXXVII, $R_3$ can be selected from the group consisting of hydrogen, a straight or branched alkyl, cycloalkyl, aryl, olefin, silyl, alkylsilyl, arylsilyl, alkylaryl, arylalkyl, methoxy, ethoxy, amino, or fluorocarbon chain of 1-50 carbons, wherein each alkyl, cycloalkyl, aryl, olefin, silyl, alkylsilyl, arylsilyl, alkylaryl, arylalkyl, or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents. In some embodiments, $R_3$ is a $C_1$-$C_6$ alkyl or $C_2$-$C_6$ alkenyl. In some embodiments, $R_3$ can be methyl, ethyl, or propyl.

In compounds of Formulas I-XIV and XVII-XXXVII, X can be O, S, Se, or NH. In some embodiments, X is O or NH. In one embodiment, X is O.

In compounds of Formulas I-XIV and XVII-XXXVII, $X_1$, $X_2$, $X_3$, $X_4$, $X_5$, and $X_6$ are independently OH, $OSO_3H$, $OSO_3^-J^+$, $OPO_3H_2$, $OPO_3H^-J^+$, $OPO_3^{2-}2J^+$, $OPO_3^{2-}Z^{2+}$, $NH_2$, or $NC(O)CH_3$, wherein $J^+$ is a monovalent cation and $Z^{2+}$ is a divalent cation In compounds of Formulas I-XIV and XVII-XXXVII, each Y can be selected independently from H, $CH_2OH$, COOH, $COO^-J^+$, $CH_2OSO_3H$, $CH_2OSO_3^-J^+$, $CH_2OPO_3H_2$, $CH_2OPO_3H^-J^+$, $CH_2OPO_3^{2-}2J^+$, or $CH_2OPO_3^{2-}Z^{2+}$, wherein $J^+$ is a monovalent cation and $Z^{2+}$ is a divalent cation.

In some embodiments, $J^+$ can be Li, Na, K, Rb, Cs, or a complex cation with charge $1^+$. In some embodiments, $Z^{2+}$ can be Be, Mg, Ca, Sr, Ba, or a complex cation with charge $2^+$.

In compounds of Formulas I-XIV and XVII-XXXVII, $Q_1$, $Q_2$ and $Q_3$ are each independently C or Si. In some embodiments, only one of $Q_1$, $Q_2$ and $Q_3$ is C. In some embodiments, only two of $Q_1$, $Q_2$ and $Q_3$ are C. In one embodiment, $Q_1$, $Q_2$ and $Q_3$ all are C.

In some embodiments, at least one (e.g., one, two, or three) of $Q_1$, $Q_2$, and $Q_3$ (and the R substituents linked to it) is replaced by ethylene glycol (e.g., —$CH_2CH_2O$—) or a hydrophilic monomer.

In embodiments of compounds of Formulas I-XIV and XVII-XXXVII, $E_1$, $E_2$, $E_3$, $E_4$, and $E_5$ are each independently selected from the group consisting of O, S, Se, or NH. In some embodiments, at least one of (e.g., one, two, three, four, or five) $E_1$, $E_2$, $E_3$, $E_4$, and $E_5$ is O or S. In some embodiments, at least one of $E_2$, $E_3$, $E_4$, and $E_5$ is S. In some embodiments, $E_1$, $E_2$, $E_3$, $E_4$, and $E_5$ are all O.

Variables n and m in compounds of formulas I-XIV and XVII-XXXVII are independently an integer from 0 to 20. In some embodiments, n and m both are same. In some embodiments, n and m are different. In some embodiments, n and m are selected independently from 1, 2, 3, 4, 5, 6, 7, 8, 9, 10, 11, 12, 13, 14, or 15. In one embodiment, n and m are both 2.

Variable a in compounds of formulas I-XIV and XVII-XXXVII is an integer from 0 to 1200.

In some embodiments, the monomer can be selected from the group consisting of N,N-dimethyl-N-acryloyloxyethyl-N-(3-sulfopropyl)-ammonium betaine, N,N-dimethyl-N-acrylamidopropyl-N-(2-carboxymethyl)-ammonium betaine, N,N-dimethyl-N-acrylamidopropyl-N-(3-sulfopropyl)-ammonium betaine, N,N-dimethyl-N-acrylamidopropyl-N-(2-carboxymethyl)-ammonium betaine, 2-(methylthio)ethyl methacryloyl-S-(sulfopropyl)-sulfonium betaine, 2-[(2-acryloylethyl)dimethylammonio]ethyl 2-methyl phosphate, 2-(acryloyloxyethyl)-2'-(trimethylammonium)ethyl phosphate, [(2-acryloylethyl)dimethylammonio]methyl phosphonic acid, 2-methacryloyloxyethyl phosphorylcholine (MPC), 2-[(3-acrylamidopropyl)dimethylammonio] ethyl 2'-isopropyl phosphate (AAPI), 1-vinyl-3-(3-sulfopropyl)imidazolium hydroxide, (2-acryloxyethyl) carboxymethyl methylsulfonium chloride, 1-(3-sulfopropyl)-2-vinylpyridinium betaine, N-(4-sulfobutyl)-N-methyl-N,N-diallylamine ammonium betaine (MDABS), N,N-diallyl-N-methyl-N-(2-sulfoethyl)ammonium betaine, and any combinations thereof.

In some embodiments, the monomer is 2-methacryloyloxyethyl phosphorylcholine (MPC).

In some embodiments, the monomer is PEGMA.

In some embodiments, the monomer is a combination of MPC and PEGMA.

Without wishing to be bound by a theory, increased entanglement of the polymer within the tissue in the tissue-polymer IPN construct increases the likelihood of the polymer remaining in the tissue. If the polymer is linear and not crosslinked, then a tissue-polymer IPN under repeated loading cycles can deteriorate as the polymer escapes from the construct. Accordingly, to prevent this effect, in some embodiments, the inventive polymers comprise in part a crosslinking agent or crosslinking monomer. This can reduce the mobility of the polymer and thereby increase the residence time of the polymer within the tissue. As used herein, the term "cross-linker monomer" refers to any molecule has a plurality of (e.g., two or more) of reactive groups that can undergo polymerization. Suitable crosslinking agents include compounds whose molecule has a plurality of reactive groups. Such molecular crosslinking agents can be N,N'-methylenebis-acrylamide (BA), polyethyleneglycol di(meth)acrylate (PEG-DM), divinylbenzene (DVB), ethylene glycol dimethacrylate (EGDMA), divinyl ketone, vinyl methacrylate and divinyl oxalate In some embodiments, the cross-linker monomer can be selected from the compounds of formula XV and XVI:

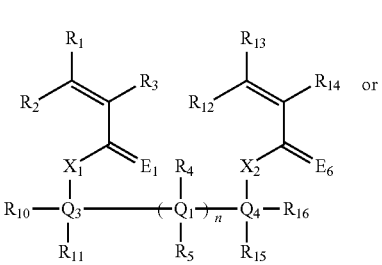

Formula XV

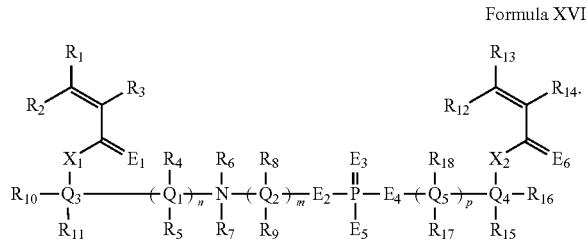

Formula XVI

In compounds of formula XV and XVI, $R_1$, $R_2$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ are each independently selected from the group consisting of alkyl, alkenyl, alkynyl, H, halide, ether-linked alkyl, ether-linked alkenyl, ether-linked alkynyl; $R_3$ is selected from the group consisting of hydrogen, a straight or branched alkyl, cycloalkyl, aryl, olefin, silyl, alkylsilyl, arylsilyl, alkylaryl, arylalkyl, methoxy, ethoxy, amino, or fluorocarbon chain of 1-50 carbons, wherein each alkyl, cycloalkyl, aryl, olefin, silyl, alkylsilyl, arylsilyl, alkylaryl, arylalkyl, or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; $X_1$ and $X_2$ are each independently selected from O, S, Se, and NH; $Q_1$, $Q_2$, $Q_3$, $Q_4$, and $Q_5$ are each independently selected from the group consisting of C or Si; $E_1$, $E_2$, $E_3$, $E_4$, $E_5$, and $E_6$ are each independently selected from the group consisting of O, S, Se, or NH; and n, m, and p are integers, each independently ranging from 0-14.

In some embodiments of compounds of formula XV and XVI, $R_1$, $R_2$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ can be independently H, $C_1$-$C_6$ alkyl, $C_2$-$C_6$ alkenyl, fluoro, bromo, or chloro.

In some embodiments of compounds of formula X and XVI, $R_1$ and $R_2$ can be same or different. In some embodiments, $R_1$ and $R_2$ are both H.

In embodiments of compounds of formula XV and XVI, $R_3$ can be H or $C_1$-$C_6$ alkyl. In some embodiments, $R_3$ is methyl.

In some embodiments of compounds of formula X and XVI, $R_4$ and $R_5$ can be same or different. In some embodiments, $R_4$ and $R_5$ are both H.

In some embodiments of compounds of formula X and XVI, $R_6$ and $R_7$ can be same or different. In some embodiments, $R_6$ and $R_7$ are both independently $C_1$-$C_6$ alkyl. In one embodiment, $R_6$ and $R_7$ are both methyl.

In some embodiments of compounds of formula X and XVI, $R_8$ and $R_9$ can be same or different. In some embodiments, $R_8$ and $R_9$ are both H.

In some embodiments of compounds of formula X and XVI, $R_{10}$ and $R_{11}$ can be same or different. In some embodiments, $R_{10}$ and Rim are both H.

In some embodiments of compounds of formula X and XVI, $R_{12}$ and $R_{13}$ can be same or different. In some embodiments, $R_{12}$ and $R_{13}$ are both H.

In embodiments of compounds of formula XV and XVI, $R_{14}$ can be H or $C_1$-$C_6$ alkyl. In some embodiments, $R_{14}$ is methyl.

In some embodiments of compounds of formula X and XVI, $R_{15}$ and $R_{16}$ can be same or different. In some embodiments, $R_{15}$ and $R_{16}$ are both H.

In some embodiments of compounds of formula X and XVI, $R_{17}$ and $R_{18}$ can be same or different. In some embodiments, $R_{17}$ and $R_{18}$ are both H.

In embodiments of compounds of formula XV and XVI, $X_1$ can $X_2$ can be same or different. In some embodiments, $X_1$ can be O or S. In one embodiment, $X_1$ is O. In some embodiments, $X_2$ can be O or S. In one embodiment, $X_2$ is O.

In some embodiments of compounds of formula XV and XVI, at least one (e.g., one, two, three, four, or five) of $Q_1$, $Q_2$, $Q_3$, $Q_4$, and $Q_5$ are C.

In compounds of Formulas I-XIV and XVII-XXXVII, $Q_1$, $Q_2$ and $Q_3$ are each independently C or Si. In some embodiments, only one of $Q_1$, $Q_2$ and $Q_3$ is C. In some embodiments, only two of $Q_1$, $Q_2$ and $Q_3$ are C. In one embodiment, $Q_1$, $Q_2$ and $Q_3$ all are C.

In some embodiments of compounds of formula XV and XVI, at least one (e.g., one, two, three, four, or five) of $Q_1$, $Q_2$, $Q_3$, $Q_4$, and $Q_5$ are (and the R substituents linked to it) is replaced by ethylene glycol (e.g., —$CH_2CH_2O$—) or a hydrophilic monomer.

In embodiments of compounds of formulas XV and XVI, $E_1$, $E_2$, $E_3$, $E_4$, $E_5$, and $E_6$ are each independently selected from the group consisting of O, S, Se, or NH. In some embodiments, at least one of (e.g., one, two, three, four, or five) $E_1$, $E_2$, $E_3$, $E_4$, $E_5$, and $E_6$ is O or S. In some embodiments, at least one of $E_1$ and $E_6$ is O. In some embodiments, $E_1$ and $E_6$ are both O.

In some embodiments, $E_5$ is O or S. In some embodiments, at least one of (e.g., one, two or three) of $E_2$, $E_3$, and $E_4$ are O or S. In some embodiments, $E_2$, $E_3$, and $E_4$ all are O.

In some compounds of formula XV and XVI, n and m both are same. In some embodiments, n and m are different. In some embodiments, n and m are selected independently from 1, 2, 3, 4, 5, or 6. In one embodiment, n and m are both 2.

In some embodiments, the cross-linker is ethylene glycol dimethacrylate (EGDMA); methacryloyloxyethyl-N-(2-methacryloyloxyethyl phosphorylcholine); di-, tri-, tetra-, penta-, and hexa(ethylene glycol) dimethacrylate; "Medium" length PEG crosslinkers, such as PEG diacrylates or PEG dimethacrylates with molecular weights ranging from 500 to 50,000 Da (e.g., 500, 1,000, 2,000, 3,400, 5,000, 10,000, 20,000, and 50,000 Da). In some embodiments, the cross-linker is methylene bisacrylate, methylene bisacrylamide, methylene bismethacrylate, or methylene bismethacrylamide. In general, any molecule that is hydrophilic and has a plurality of polymerizable groups can be used as a cross-linker. In some embodiments, the cross-linker is a degradable (e.g. biodegradable) cross-linker, including those containing disulfide bonds, ester bonds, carbonate bonds, amide bonds, or other bonds in the crosslinker backbone that may be cleaved.

Without wishing to be bound by a theory, degree of cross-linking in the polymer can also affect its properties. Accordingly, the degree of cross-linking can range from 0% (i.e., no cross-linking) to 100% (i.e. all groups for available for cross-linking are used). In some embodiments, degree of cross-linking is in the range of from about 5% to about 95%, from about 10% to about 90%, from about 15% to about 80%, from about 20% to about 75%, or from about 25% to about 50%. In some embodiments, degree of cross-linking is 5% or less. For example 4%, 3%, 2%, 1.5%, 1%, 0.75%, 0.5%, 0.25%, 0.2% or less. In some embodiments, degree of cross-linking is at least 0.05%. the range of from about 5% to about 95%, from about 10% to about 90%, from about 15% to about 80%, from about 20% to about 75%, or from about 25% to about 50%. In some embodiments, the degree of cross-linking can range from about 0.1% to about 20%. In one embodiments, the degree of cross-linking can range from about 1% to about 5%.

The polymer can be any shape or form. For example, the polymer can be formed as a gel or hydrogel. As used herein, the term "hydrogel" refers to a three-dimensional polymeric structure that is insoluble in water or some other liquid but which is capable of absorbing and retaining large quantities of water or some other liquid to form a stable, often soft and pliable, structure. In some embodiments, water or some other liquid can penetrate in between the polymer chains of the polymer network, subsequently causing swelling and the formation of a hydrogel.

In some embodiments, the polymer can be present in a solution. Amount of the polymer in the solution can be any desired amount. For example, the amount of polymer in the solution can range from about 0.001% (w/v) to about 90% (w/v). In some embodiments, the amount of polymer in the solution can range from about 0.5% (w/v) to about 40% (w/v). In some embodiments, the amount of polymer in the solution can range from about 1% (w/v) to about 10% (w/v). In some embodiments, the amount of polymer in the solution can be about 20% (w/v).

In some embodiments, the solution comprising the polymer is a dilute solution. As used herein, the term "dilute solution" means a solution comprising the polymer wherein amount of the polymer in the solution is about 10% (w/v) or less. In some embodiments, the amount of the polymer in the solution is in the range from about 0.5% (w/v) to about 40% (w/v). In one embodiment, the amount of the polymer in the solution is in the range from about 1% (w/v) to about 10% (w/v).

The amount of the polymer in the solution can affect the viscosity of the solution. Thus, the solution comprising the polymer can be viscous or non-viscous. As used herein, the term "viscous" means a liquid material, e.g. a solution comprising the polymer, with viscosity of several hundreds centipoises to several millions centipoises. For example a viscosity of from about 100 cP to about $10^6$ cP. Without wishing to be bound by a theory non-viscous solutions (1-100 cp) can be useful as non-viscous lubricants and viscous solutions (100-$10^6$ cp) can be useful as viscous lubricants i.e. viscosupplements.

In some embodiments, the inventive polymer is biocompatible. In some embodiments, the inventive polymer is biodegradable.

In one aspect the disclosure provides a method for synthesizing the polymer in situ, for example in a tissue. Generally, the method comprises contacting a tissue with a composition comprising monomers for polymerization; allowing the monomers to permeate the tissue; and polymerizing the monomers. The monomers can be allowed to permeate throughout the tissue or only a part of the tissue. Thus, the synthesized polymer can be present throughout the tissue's bulk or only a part of the tissue's bulk. The composition comprising the monomers for polymerization is also referred to as a polymerizable composition.

Without limitations, said contacting can in vitro, ex vivo, or in vivo. The term "contacting" or "contact" as used herein in connection with contacting a tissue includes subjecting the tissue to an appropriate culture media which comprises the indicated polymerizable composition. Where the tissue is in vivo, "contacting" or "contact" includes administering the polymerizable composition (e.g., formulated in a pharmaceutical composition) to a subject via an appropriate administration route such that the composition contacts the tissue in vivo and can diffuse through at least a part of the tissue. Methods of administering compounds to a subject are known in the art and easily available to one of skill in the art.

Without limitations, the permeation can be by passive diffusion or by a practitioner controlled-diffusion. For example, when the tissue is in vivo, the permeation of the monomers in the tissue can be controlled by a medical practitioner. Diffusion can be controlled by, for example, one or more of ultrasound stimulation, application of heat, application of cold, application of relative high pressure, application of relative low pressure, and mechanical tissue convection.

After the desired amount of permeation, the monomers can be polymerized using any means available to one skill in the art for polymerization. For example, monomers can be polymerized using radical polymerization, cationic polymerization, anionic polymerization, reversible addition-fragmentation chain transfer (RAFT) polymerization, atom-transfer radical (ATR) polymerization, or any combinations thereof. In some embodiments, polymerization can occur spontaneously after permeation. In some other embodiments, polymerization can occur during permeation.

In some embodiments, polymerization can be initiated using a light source. The light source can emit light radially or non-radially. Useful light sources include, but are not limited to, lamps, fiber optics devices, lasers, etc. . . . . In some embodiments, the light source can be a laser. In some other embodiments, the light source is not a laser. In some embodiments, the light source can be part of a device for contacting or administering the polymerizable composition to the tissue.

For initiation polymerization, light can be applied for a period of seconds to several minutes or hours. For example, the light can be applied for about 10 seconds to about 5 minutes. In certain embodiments, light is applied for about 10 to about 60 seconds. In some embodiments, light is applied for about 10 to about 30 seconds. In some embodiments, light is applied for about 20 to about 40 seconds. In some embodiments, light is applied for about 35 seconds. The light source can allow variation of the wavelength of light and/or the intensity of the light.

Light of any wavelength can be used based on the monomers utilized. For example, polymerization can be initiated using UV light (200-500 nm). In certain embodiments, long UV rays can be used. In other embodiments, short UV rays can be used. In some embodiments, polymerization can be initiated using visible light (400-800 nm). In certain embodiments, polymerization can be initiated using blue light (420-500 nm). In certain embodiments, polymerization can be initiated using green light (500-575 nm). In some embodiments, polymerization can be initiated using IR light (800-2500 nm). The output of light can be controlled to provide greater control over the polymerization reaction. Control over the reaction in turn results in control over the characteristics and/or properties of the resulting polymer. In certain embodiments, the intensity of light ranges from about 500 to about $10^6$ μW/cm$^2$. In some embodiments, the intensity of light is about 4000, about 5000, about 6000, about 7000, about 8000, or about 9000 μW/cm$^2$. In some embodiments, the intensity of light is about 200,000-500,000 μW/cm$^2$.

When a light source is used for initiating the polymerization, the polymerizable composition can further comprise one or a combination of two or more photo-initiators.

Photo-initiators produce reactive free radical species that initiate the crosslinking and/or polymerization of monomers upon exposure to light. Any photo-initiator can be used in the crosslinking and/or polymerization reaction. Photoinitiated polymerizations and photo-initiators are discussed in detail in Rabek, Mechanisms of Photophysical Processes and Photochemical Reactions in Polymers, New York: Wiley & Sons, 1987; Fouassier, Photoinitiation, Photopolymerization, and Photocuring, Cincinnati, Ohio: Hanser/Gardner; Fisher et al., 2001, Annu. Rev. Mater. Res., 31:171. A photo-initiator can be designed to produce free radicals at any wavelength of light. For example, a photo-initiator can be designed to work using UV light (200-500 nm). In some embodiments, a photo-initiator is designed to work using visible light (400-800 nm). In certain embodiments, a photo-initiator is designed to work using blue light (420-500 nm). In certain embodiments, a photo-initiator is designed to work using green light (500-575 nm). In some embodiments, the photo-initiator is designed to work using IR light (800-2500 nm).

In some embodiments, the photo-initiator can be a peroxide (e.g., ROOR'), a ketone (e.g., RCOR'), an azo compound (e.g., compounds with a —N═N— group), an acylphosphineoxide, a sulfur-containing compound, a quinone. Exemplary photo-initiators include, but are not limited to, acetophenone; anisoin; anthraquinone; anthraquinone-2-sulfonic acid, sodium salt monohydrate; (benzene) tricarbonylchromium; 4-(boc-aminomethyl)phenyl isothiocyanate; benzin; benzoin; benzoin ethyl ether; benzoin isobutyl ether; benzoin methyl ether; benzoic acid; benzophenyl-hydroxycyclohexyl phenyl ketone; 3,3',4,4'-benzophenonetetracarboxylic dianhydride; 4-benzoylbiphenyl; 2-benzyl-2-(dimethylamino)-4'-morpholinobutyrophenone; 4,4'-bis(diethylamino)benzophenone; 4,4'-bis(dimethylamino)benzophenone; Michler's ketone; camphorquinone; 2-chlorothioxanthen-9-one; 5-dibenzosuberenone; (cumene)cyclopentadienyliron(II) hexafluorophosphate; dibenzosuberenone; 2,2-diethoxyacetophenone; 4,4'-dihydroxybenzophenone; 2,2-dimethoxy2-phenylacetophenone; 4-(dimethylamino)benzophenone; 4,4'-dimethylbenzyl; 2,5-dimethylbenzophenone; 3,4-dimethylbenzophenone; diphenyl(2,4,6-trimethylbenzoyl)phosphine oxide; 2-hydroxy-2-methylpropiophenone; 4'-ethoxyacetophenone; 2-ethylanthraquinone; ferrocene; 3'-hydroxyacetophenone; 4'-hydroxyacetophenone; 3-hydroxybenzophenone; 4-hydroxybenzophenone; 1-hydroxycyclohexyl phenyl ketone; 2-hydroxy-2-methylpropiophenone; 2-methylbenzophenone; 3-methylbenzophenone; methybenzoylformate; 2-methyl-4'-(methylthio)-2-morpholinopropiophenone; 9,10-phenanthrenequinone; 4'-phenoxyacetophenone; thioxanthen-9-one; triarylsulfonium hexafluoroantimonate salts; triarylsulfonium hexafluorophosphate salts; 3-mercapto-1-propanol; 11-mercapto-1-undecanol; 1-mercapto-2-propanol; 3-mercapto-2-butanol; hydrogen peroxide; benzoyl peroxide; 4,4'-dimethoxybenzoin; 2,2-dimethoxy-2-phenylacetophenone; dibenzoyl disulphides; diphenyldithiocarbonate; 2,2'-azobisisobutyronitrile (AIBN); camphorquinone (CQ); eosin; dimethylaminobenzoate (DMAB); dimethoxy-2-phenyl-acetophenone (DMPA); Quanta-cure ITX photosensitizer (Biddle Sawyer); Irgacure 907 (Ciba Geigy); Irgacure 2959 (CIBA Geigy); Irgacure 651 (Ciba Geigy); Darocur 2959 (Ciba Geigy); ethyl-4-N,N-dimethylaminobenzoate (4EDMAB); 1-[-(4-benzoylphenylsulfanyl)phenyl]-2-methyl-2-(4-methylphenylsulfonyl)propan 1-one; 1-hydroxy-cyclohexyl-phenyl-ketone; 2,4,6trimethylbenzoyldiphenylphosphine oxide; diphenyl(2,4,6trimethylbenzoyl) phosphine; 2-ethylhexyl-4dimethylaminobenzoate; 2-hydroxy-2-methyl-1-phenyl-1 propanone; 65% (oligo[2-hydroxy-2-methyl-1-[4-(lmethylvinyl)phenyl]propanone] and 35% propoxylated glyceryl triacrylate; benzil dimethyl ketal; benzophenone; blend of benzophenone and a-hydroxy-cyclohexyl-phenylketone; blend of Esacure KIP150 and Esacure TZT; blend of Esacure KIP150 and Esacure TZT; blend of Esacure KIP150 and TPGDA; blend of phosphine oxide, Esacure KIP150 and Esacure TZT; difunctional a-hydroxy ketone; ethyl 4-(dimethylamino)benzoate; isopropyl thioxanthone; 2-hydroxy-2methyl-phenylpropanone; 2,4,6,-trimethylbenzoyldipheny 1 phosphine oxide; 2,4,6-trimethyl benzophenone; liquidblend of 4-methylbenzophenone and benzophenone; oligo(2-hydroxy-2 methyl-1-(4(1-methylvinyl)phenyl)propanone; oligo(2-hydroxy-2-methyl-1-4(1-methylvinyl)phenyl propanone and 2-hydroxy-2-methyl-1-phenyl-1-propanone (monomeric); oligo(2-hydroxy-2-methyl-1-4(1-methylvinyl)phenyl propanone and 2-hydroxy-2-methyl-1-phenyl-1propanone (polymeric); 4-methylbenzophenone; trimethylbenzophenone and methylbenzophenone; and water emulsion of 2,4,6-trimethylbenzoylphosphine oxide, alpha hydroxyketone, trimethylbenzophenone, and 4-methyl benzophenone. In certain embodiments, the photo-initiator is acetophenone; diphenyl(2,4,6-trimethylbenzoyl)phosphine oxide; 4,4'-dimethoxybenzoin; anthraquinone; anthraquinone-2-sulfonic acid; benzene-chromium(O) tricarbonyl; 4-(boc-aminomethyl)phenyl isothiocyanate; benzil; benzoin; benzoin ethyl ether; benzoin isobutyl ether; benzoin methyl ether; benzophenone; benzoic acid; benzophenone/1 hydroxycyclohexyl phenyl ketone, 50/50 blend; benzophenone-3,3',4,4'-tetracarboxylic dianhydride; 4-benzoylbiphenyl; 2-benzyl-2-(dimethyl amino)-4' morpholinobutyrophenone; 4,4'-bis(diethylamino) benzophenone; Michler's ketone; (±)-camphorquinone; 2-chlorothioxanthen-9-one; 5-dibenzosuberenone; 2,2-diethoxyacetophenone; 4,4'-dihydroxybenzophenone; 2,2dimethoxy-2-phenylacetophenone; 4-(dimethylamino)benzophenone; 4,4'-dimethylbenzil; 3,4dimethylbenzophenone; diphenyl (2,4,6-trimethylbenzoyl) phosphine oxide/2-hydroxy methylpropiophenone; 4'-ethoxyacetophenone; 2-ethylanthraquinone; ferrocene; 3'-hydroxyacetophenone; 4'-hydroxyacetophenone; 3-hydroxybenzophenone; 4-hydroxybenzophenone; 1-hydroxycyclohexyl phenyl ketone; 2-hydroxy-2-methylpropiophenone; 2-methylbenzophenone; 3-methylbenzophenone; methyl benzoylformate; 2-methyl-4'-(methylthio)-2-morpholinopropiophenone; 9,10-phenanthrenequinone; 4'-phenoxyacetophenone; thioxanthen-9-one; triarylsulfonium hexafluorophosphate salts; 3-mercapto-1-propanol; 11-mercapto-1-undecanol; 1-mercapto-2-propanol; and 3-mercapto-2-butanol, all of which are commercially available from Sigma-Aldrich. In certain embodiments, the free radical initiator is selected from the group consisting of benzophenone, benzyl dimethyl ketal, 2-hydroxy-2-methyl-phenylpropanone; 2,4,6-trimethylbenzoyldiphenyl phosphine oxide; 2,4,6-trimethyl benzophenone; oligo(2-hydroxy-2-methyl-1 (4-(1-methylvinyl)phenyl)propanone and 4-methylbenzophenone. In some embodiments, the photo-initiator is dimethoxy-2-phenyl-acetophenone (DMPA), a titanocene, 2-hydroxy-1-(4(hydroxyethoxy)phenyl)-2-methyl-1-propanone, Igracure. In some embodiments, the initiator is 2-hydroxy-1-(4-(hydroxyethoxy) phenyl)-2-methyl-1-propanone (Irgacure 2959, CIBA Chemicals).

An initiator of a cationic or anionic crosslinking and/or polymerization process can be used. Generally, any chromophore or a compound having a plurality of conjugated pi bonds that can be excited by light and can promote an electron from a ground state to an excited state, thus rendering the electron capable of being transferred (either directly or indirectly with the use of a coinitiator, as described below) can be used as an initiator for the polymerization process. Exemplary photo-initiators of cationic crosslinking and/or polymerization include, but are not limited to, titanium tetrachloride, vanadium tetrachloride, bis(cyclopentadienyl)titanium dichloride, ferrocene, cyclopentadienyl manganese tricarbonyl, manganese decacarbonyl, diazonium salts, diaryliodonium salts (e.g., 3,3'-dinitrodiphenyliodonium hexafluoroarsenate, diphenyliodonium fluoroborate, 4-methoxydiphenyliodonium fluoroborate) and triarylsulfonium salts.

In some embodiments, the photo-initiator is selected from the group consisting of eosin, eosin B, eosin Y, an eosin derivative, 1-[4-(2-Hydroxyethoxy)-phenyl]-2-hydroxy-2-methyl-1-propane-1-one, a 1-[4-(2-Hydroxyethoxy)-phenyl]-2-hydroxy-2-methyl-1-propane-1-one derivative, thionine, safranine, methylene blue, acridine orange, xanthene derivatives, and any combinations thereof.

In general, photo-initiators are utilized at concentrations ranging between approximately 0.0005% w/v and 5.0% w/v. For example, photo-initiators can be utilized at concentrations of about 0.005% w/v, about 0.01% w/v, about 0.025% w/v, about 0.05% w/v, about 0.075% w/v, about 0.1% w/w, about 0.125% w/v, about 0.25% w/v, about 0.5% w/v, about 0.75% w/v, about 1% w/v, about 1.125% w/v, about 1.25% w/v, about 1.5% w/v, about 1.75% w/v, about 2% w/v, about 2.125% w/v, about 2.25% w/v, about 2.5% w/v, about 2.75% w/v, about 3% w/v, about 3.125% w/v, about 3.25% w/v, about 3.5% w/v, about 3.75% w/v, about 4% w/v, about 4.125% w/v, about 4.25% w/v, about 4.5% w/v, about 4.75% w/v, about 5% w/v or higher, although high concentrations of photo-initiators can be toxic to cells.

In some embodiments, the polymerizable composition further comprises a co-initiator. In some embodiments, the co-initiator is an amine. In some embodiments, a co-initiator is exogenously added. In some embodiments, a co-initiator is not exogenously added, and a reactant molecule already participating in the polymerization serves a secondary role of co-initiator. In some embodiments, the co-initiator is selected from the group consisting of triethanolamine, N-methyl-N,N-diethanolamine, N-ethyl-N,N-diethanolamine, an ester of dimethylaminobenzoic acid, 2,6-diisopropyl-N,N-dimethylaniline, 2-benzyl-2-(dimethylamino)-4'-morpholinobutyrophenone, carbon tetrabromide, [4-[(2-hydroxytetradecyl)oxy]phenyl]phenyliodonium hexafluoroantimonate, Ethylenediamine-N,N,N',N'-tetra(2-propanol), 1,4-dimethylpiperazine, Tribenzylamine, diazabicyclo[2,2,2]octane, N-phenyldiethanolamine, allylthiourea, 4-(Dimethylamino)benzaldehyde, 2,6-Diisopropyl-N,N-dimethylaniline, 7-(Diethylamino)-4-methylcoumarine, 2-Mercaptobenzimidazol, and any combinations thereof.

Without limitations, a monomer in the polymerization can serve the role of co-initiator (e.g. an amine-containing monomer), and the primary photoinitiator can also serve the role of its own co-initiator (e.g. if the photoinitiator contains an amine, one molecule gets excited by light, and another molecule's amine takes part in co-initiation).

In some embodiments, the polymerizable composition further comprises an accelerant, e.g., a polymerization accelerant. As used herein, an "accelerant" or "accelerator" for a polymerization reaction refers to a compound that can assist the polymerization of polymerizable material following initiation of the reaction. Generally, an accelerator will promote completion of the polymerization reaction and/or increase the rate that the polymerizable material becomes incorporated into a polymerized product. Compounds with an N-vinyl group can serve as accelerants in the compositions, polymers, and methods disclosed herein. In some embodiments, accelerant is N-vinyl pyrrolidone. Other exemplary accelerants are described in, for example, PCT Publication No. WO2005054304 and PCT Application No. PCT/US2004/038053 (Biocompatible polymerization accelerators), contents of both of which are incorporated herein by reference in their entireties.

Similar to photo-initiators, accelerants are utilized at concentrations ranging between approximately 0.005% w/v and 5.0% w/v. For example, accelerant can be utilized at concentrations of about 0.005% w/v, about 0.01% w/v, about 0.025% w/v, about 0.05% w/v, about 0.075% w/v, about 0.1% w/w, about 0.125% w/v, about 0.25% w/v, about 0.5% w/v, about 0.75% w/v, about 1% w/v, about 1.125% w/v, about 1.5% w/v, about 1.5% w/v, about 1.75% w/v, about 2% w/v, about 2.125% w/v, about 2.25% w/v, about 2.5% w/v, about 2.75% w/v, about 3% w/v, about 3.125% w/v, about 3.25% w/v, about 3.5% w/v, about 3.75% w/v, about 4% w/v, about 4.125% w/v, about 4.25% w/v, about 4.5% w/v, about 4.75% w/v, about 5% w/v or higher, although high concentrations of accelerant can be toxic to cells. In some embodiments, accelerant can be utilized at concentrations of about 0.05% w/v to about 5% w/v. Generally, the concentration of the accelerant should be kept to a minimum if the accelerant exhibits toxicity.

Without wishing to be bound by a theory, characteristics or properties of the polymer can be altered and/or controlled by altering polymerization conditions. For example, polymerization utilizing longer wavelengths tends to generate polymeric matrices (e.g., hydrogels) with less toxicity. Polymerization for longer periods of time tends to generate polymeric matrices with stiffer mechanical properties, although higher doses of UV can be toxic to cells. Polymerization utilizing higher-power UV light tends to generate polymeric matrices with higher mechanical stiffnesses and more extensive crosslinking.

The disclosure also provides an interpenetrating network comprising the polymer, e.g., the in situ synthesized polymer and component of the tissue in which the polymer is synthesized. For example, the IPN comprises a first network and a second network, wherein the first network comprises components of the tissue and the second network comprises the polymer disclosed herein. In some embodiments, the tissue is cartilage.

Without wishing to be bound by theory, one exemplary use of in situ formation of a tissue-interpenetrating hydrogel is the formation of said hydrogel near the interface between a soft tissue and a stiff material. The IPN can be formed near, adjacent to, or surrounding the material of increased stiffness. In some contexts, the stiff material can be bone. In yet other contexts, the material can be an implanted device. At such interfaces between soft tissue and a stiffer material, the stiff material can often do damage to the soft tissue because of the mismatch of mechanical properties. To mitigate this pathologic challenge, the interpenetrating hydrogel can lessen the degree of disparity in mechanical properties between the soft tissue it is interpenetrating and the nearby stiff material, thereby creating intermediate mechanical properties so that there exists less of an abrupt change in mechanical properties at the soft-hard interface. This inventive therapeutic approach can protect the soft tissue from damage because the stiff bone, device, or other material's ability to translate throughout the soft tissue can acutely or chronically damage the tissue. The approach can also prevent, minimize, or mitigate the buildup of scar tissue. The approach can also prevent the hard material (e.g. bone) from translating or rotating and may thereby aid in "setting" the bone after a fracture. The approach can afford these advantages for a certain period of time if the in situ synthesized IPN is biodegradable, enabling the alteration of the soft tissue's mechanical properties only for a duration desired by the medical practitioner.

The disclosure of an in situ polymerized hydrogel also provides a means of preventing, mitigating, or minimizing the existence of undesired agents within a tissue. The diffusion or transport of said agents into the tissue can be slowed (i.e. their infiltration into the tissue can be slowed), the final equilibrium quantity of said agents in the tissue can be decreased (i.e. effective intra-tissue concentration of said agents can be decreased), and the transport or ability of the agents to freely diffuse can be decreased (i.e. an effective decrease in tissue permeability to the said agents). Without wishing to be bound by theory, the undesired agents can include invading degradative enzymes (e.g. catabolic enzymes such as proteolytic, saccharolytic, or lipolytic enzymes), inflammatory agents, or harmful/pathogenic agents such as bacteria, viruses, cancerous cells, mutagens, toxic small molecules, toxic large molecules, and the like. Via this intended use, the treated tissue can thereby be protected to a certain extent from the undesired chemical or biological mechanism of action of the undesired agent.

The disclosure also provides a polymer synthesized ex situ. For example a polymer synthesized in the absence of a tissue. Inventors have discovered that the ex situ synthesized polymers can be used as lubricants, e.g., biolubricant.

The provided disclosure of an ex situ synthesized polymer network that can be suspended in aqueous solution to yield a lubricant can be used to lubricate the articulation of numerous tissue types, including but not limited to cartilage, other synovial joint tissues, mucosa, or any other soft tissues that can benefit from increased lubrication. Polymers of the formulations disclosed herein possess benefits such as: extended in vivo residence times due to presence of cross-linking within the polymer backbone (and hence increased effective molecular weight for retention in desired parts of the body), low manufacturing costs compared to lubricants or viscosupplements or other supplements composed of biological polymers (e.g. hyaluronic acids, hyaluronates, or hyaluronans, and owing to its shear-thinning behavior it can be easily passed through a thin 27 gauge needle which is more patient friendly than the 18-22 g needles recommended for prior disclosed lubricants in the art.

The compositions (e.g., polymerizable compositions), polymers (e.g., in situ or ex situ synthesized polymers), and methods disclosed herein can be used for a variety of indications. For example, the compositions, polymers, and methods disclosed herein can be used for tissue supplements, viscosupplements, viscoelastics, tissue space fillers, reconstructive or cosmetic enhancement procedures, urinary incontinence, vocal cord augmentation, and anti-adhesives.

In many indications for which the compositions, polymers, and methods disclosed herein are used, there can exist a benefit or usefulness of long or extended polymer residence time in the intended tissue or part of the body. The polymer backbone is less susceptible to the common modes of biomacromolecular degradation, namely, proteolytic or saccharolytic, to which many biologically derived materials are susceptible. Without wishing to be bound by theory, this can be due to the carbon-based backbone exclusively of the in situ polymerized and ex situ polymerized (exogeneously applied) polymers described herein. For example, the polysaccharides of hyaluronic acids, hyaluronates, hyaluronans, and their derivatives have numerous commercial uses as dermal fillers and viscosupplements, however they are enzymatically degraded by physiological levels of the enzyme hyaluronidase. As another example, commercial collagen meshes are enzymatically degraded by physiological levels of collagenases (e.g. of the matrix metalloproteinase variety). This feature of the polymeric compositions described herein provides an extended use and the potential for greater duration of therapeutic, cosmetic, or otherwise desired effect.

As an example of the usefulness of extended residence time of the polymer, the in situ synthesized interpenetrating hydrogel disclosed herein can provide long lasting relief of pain arising from mechanically damaged articular cartilage for patients with osteoarthritis. As another example of such usefulness, the ex situ synthesized polymer can be injected into a synovial joint of a patient to lubricate the patient's joint and thereby provide long lasting relief of pain arising from mechanically damaged articular cartilage for patients with osteoarthritis.

In other indications for which the compositions, polymers, and methods disclosed herein are used, there may exist a usefulness of short or moderate-length residence time, or a residence time that is intended to be of a certain target duration. To those skilled in the art it will be obvious that biodegradable polymers or polymeric compositions can be utilized in a manner similar to those described herein, to afford an interpenetrating polymer or non-interpenetrating polymer (e.g. lubricant or dermal filler) that degrades through natural biological processes in the body (e.g. hydrolysis, enzyme-mediated cleavage of ester, amide, or glycosidic bonds) or degrades through non-natural biological breakdown mechanisms (e.g. by application of an external stimulus such as light, heat, acoustic energy, a chemical or biological bond-cleaving reagent, a chemical or biological agent that disrupts polymer network or hydrogel structure through non-bond-cleaving means, or other polymer or hydrogel-degrading stimuli).

As an example of the usefulness of polymers of the type described herein that have finite, temporary, short, or moderate-length residence times, the disclosed in situ synthesized hydrogel can be used to supplement the compressive properties of a tissue that has capacity for self-repair or repair through another mechanism. In this example, the interpenetrating hydrogel would be desired for a certain duration before the tissue is repaired, but then as the tissue is repaired, the hydrogel may biodegrade. As another example of usefulness, the disclosed in situ synthesized hydrogel can be used to supplement the soft tissue surrounding a fractured bone, and then once the bone heals and the IPN is no longer therapeutically needed, it may biodegrade. Similarly, if a stiff device is to be temporarily implanted into a patient's soft tissue, the IPN can supplement the soft tissue's mechanical properties for the desired duration, and upon removal of the implanted stiff device, the IPN may biodegrade. As yet another example of usefulness, the disclosed non-interpenetrating polymer can be therapeutically desired as a lubricant or cosmetically desired as a space filler for a certain duration, and following said duration, the polymer may biodegrade.

In some embodiments, the polymers, compositions and methods disclosed herein can be used for repairing or augmenting a tissue in a subject. For example, the polymers, compositions and methods disclosed herein can be used for wound repair, soft tissue repair or augmentation, fillers for tissue space, or as templates for tissue reconstruction or regeneration. The polymers can serve as physical support and/or anti-adhesive, and/or lubricant.

In some embodiments, the compositions, polymers and methods disclosed herein can be used to fill, volumize, and/or regenerate a tissue in need thereof. In some embodiments, the compositions, polymers and methods disclosed herein can generally be used for tissue filling or volumizing, soft tissue augmentation, replacement, cosmetic enhancement and/or tissue repair in a subject. Additionally, the compositions, polymers and methods disclosed herein can be used for filling of any tissue void or indentation that are either naturally formed (e.g., aging) or created by surgical procedure for removal of tissue (e.g., a dermal cyst or a solid tumor), corticosteroid treatment, immunologic reaction resulting in lipoatrophy, tissue damage resulting from impact injuries or therapeutic treatment (e.g., radiotherapy or chemotherapy). The compositions, polymers and methods disclosed herein can also be used to raise scar depressions.

In certain embodiments, the compositions, polymers and methods disclosed herein can be used for soft tissue augmentation. As used herein, by the term "augmenting" or "augmentation" is meant increasing, filling in, restoring, enhancing or replacing a tissue. In some embodiments, the tissue can lose its elasticity, firmness, shape and/or volume. In some embodiments, the tissue can be partially or completely lost (e.g., removal of a tissue) or damaged. In those embodiments, the term "augmenting" or "augmentation" can also refer to decreasing, reducing or alleviating at least one symptom or defect in a tissue (for example, but not limited to, loss of elasticity, firmness, shape and/or volume in a tissue; presence of a void or an indentation in a tissue;

loss of function in a tissue) by injecting into the tissue with at least one injectable composition described herein. In such embodiments, at least one symptom or defect in a tissue can be decreased, reduced or alleviated by at least about 30%, at least about 40%, at least about 50%, at least about 60%, at least about 70%, at least about 80% or higher, as compared to no treatment. In some embodiments, at least one symptom or defect in a tissue can be decreased, reduced or alleviated by at least about 90%, at least about 95%, at least about 97%, or higher, as compared to no treatment. In some embodiments, at least one symptom or defect in a tissue can be decreased, reduced or alleviated by 100% (defect-free or the defect is undetectable by one of skill in the art), as compared to no treatment. In other embodiments, the tissue can be augmented to prevent or delay the onset of defect manifestation in a tissue, e.g., loss of elasticity, firmness, shape and/or volume in a tissue, or signs of wrinkles.

As used herein, the phrase "soft tissue augmentation" is generally used in reference to altering a soft tissue structure, including but not limited to, increasing, filling in, restoring, enhancing or replacing a tissue, e.g., to improve the cosmetic or aesthetic appearance of the soft tissue. Examples of soft tissue augmentation includes, but is not limited to, dermal tissue augmentation; filling of lines, folds, wrinkles, minor facial depressions, and cleft lips, especially in the face and neck; correction of minor deformities due to aging or disease, including in the hands and feet, fingers and toes; augmentation of the vocal cords or glottis to rehabilitate speech; dermal filling of sleep lines and expression lines; replacement of dermal and subcutaneous tissue lost due to aging; lip augmentation; filling of crow's feet and the orbital groove around the eye; breast augmentation; chin augmentation; augmentation of the cheek and/or nose; bulking agent for periurethral support, filling of indentations in the soft tissue, dermal or subcutaneous, due to, e.g., overzealous liposuction or other trauma; filling of acne or traumatic scars and rhytids; filling of nasolabial lines, nasoglabellar lines and intraoral lines.

In some embodiments, the compositions, polymers and methods disclosed herein can be used for soft tissue repair. The term "repair" or "repairing" as used herein, with respect to a tissue, refers to any correction, reinforcement, reconditioning, remedy, regenerating, filling of a tissue that restores volume, shape and/or function of the tissue. In some embodiments "repair" includes full repair and partial repair. For example, the volume, shape and/or function of a tissue to be repaired can be restored by at least about 30%, at least about 40%, at least about 50%, at least about 60%, at least about 70%, at least about 80% or higher, as compared to no treatment. In some embodiments, the volume, shape and/or function of a tissue to be repaired can be restored by at least about 90%, at least about 95%, at least about 97%, or higher, as compared to no treatment. In some embodiments, the volume, shape and/or function of a tissue to be repaired can be restored by 100% (defect-free or the defect is undetectable by one of skill in the art), as compared to no treatment. In various embodiments, the compositions, polymers and methods disclosed herein can be used to repair any soft tissues discussed earlier, e.g., breast, skin, and any soft tissues amenable for soft tissue augmentation. In some embodiments, the term "repair" or "repairing" are used herein interchangeably with the term "regeneration" or "regenerate" when used in reference to tissue treatment.

In some embodiments, the compositions, polymers and methods disclosed herein can be used for soft tissue reconstruction. As used herein, the phrase "soft tissue reconstruction" refers to rebuilding a soft tissue structure that was severely damaged or lost, e.g., by a dramatic accident or surgical removal.

The composition, polymers and methods described herein can also be used for filling a tissue located at or near a prosthetic implant. In some embodiments, the compositions, polymers and methods disclosed herein can be used to interface between a prosthetic implant and a tissue, e.g., to fill a void between the prosthetic implant and the tissue, and/or to prevent the tissue in direct contact with the prosthetic implant. By way of example only, after placing a prosthetic implant in a subject, a composition or polymer disclosed herein can be introduced at or adjacent to the implant to fill any void between the implant and the tissue and/or "sculpt" the tissue for a more natural look.

For administration to a subject, the polymer or the polymerizable composition can be formulated as a pharmaceutical composition. As used herein, the term "pharmaceutical composition" refers to a composition comprising an effective amount of at least one active ingredient (e.g., a polymer described herein or a polymerizable composition disclosed herein) and at least one pharmaceutically acceptable excipient or carrier. The pharmaceutical composition can be specially formulated for administration in solid (e.g., gel) or liquid form, including those adapted for the following: (1) topical application, for example, as a cream, ointment, or a controlled-release patch or spray applied to the skin; (2) intravaginally or intrarectally, for example, as a pessary, cream or foam; (3) sublingually; (4) ocularly; (5) transdermally; (6) transmucosally; (7) nasally; or (8) parenteral administration, for example, by subcutaneous, intramuscular, intravenous or epidural injection.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable carrier" refers to a carrier medium which does not interfere with the effectiveness of the biological activity of the active ingredient(s) and which is not excessively toxic to the host at the concentration at which it is administered. The term includes solvents, dispersion media, coatings, antibacterial and antifungal agents, isotonic agents, absorption delaying agents, and the like. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alchols, such as ethanol; and (23) other non-toxic compatible substances employed in pharmaceutical formulations. The use of such media and agents for pharmaceutically active substances is well known in the art (see for example, "Remington's Pharmaceutical Sciences", E. W. Martin, 18.sup.th Ed., 1990, Mack Publishing Co.: Easton, Pa., which is incorporated herein by reference in its entirety). Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

In a method of treatment of the present invention, an inventive polymer, a polymerizable composition or a pharmaceutical formulation thereof will generally be administered in such amounts and for such a time as is necessary or sufficient to achieve at least one desired result. As will be appreciated by one skilled in the art, the desired result can vary depending on the condition to be treated (e.g., osteoarthritis, cataract, dermal or subcutaneous tissue loss, urinary incontinence, or vocal cord disorder) and the purpose of the polymer (e.g., viscosupplementation, tissue augmentation, adhesion prevention, or soft tissue maintenance, support or protection). Thus, for example, in certain embodiments, a polymer or a polymerizable composition of the present invention can be administered to the knee joint of a patient suffering from osteoarthritis in such amounts and for such a time that it provides pain relief, prevents or reduces swelling, prevents or reduces loss of motion of the joint and/or or improves motion of the joint. In other embodiments, a polymer or a polymerizable composition of the present invention can be administered to the eye of a patient undergoing cataract surgery in such amounts that it allows maintenance and support of soft tissue, tissue manipulation, lubrication, tissue protection, or adhesion prevention. In yet other embodiments, a polymer or a polymerizable composition of the present invention can be administered to the skin of a patient undergoing a cosmetic procedure in such amounts and for such a time that lines, folds, wrinkles or minor facial depressions are filled.

A treatment according to the present invention can consist of a single dose or a plurality of doses over a period of time. Administration can be one or multiple times daily, weekly (or at some other multiple day interval) or on an intermittent schedule. The exact amount of an inventive polymer, polymerizable composition, or a pharmaceutical formulation thereof, to be administered will vary from subject to subject and will depend on several factors (see below).

As used herein, the term "administered" refers to the placement of a composition into a subject by a method or route which results in at least partial localization of the active ingredient at a desired site. The composition can be administered by any appropriate route which results in effective treatment in the subject, i.e. administration results in delivery to a desired location in the subject where at least a portion of the active ingredient is delivered. Exemplary modes of administration include, but are not limited to, topical, implant, injection, infusion, instillation, implantation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

In some embodiments, administration will generally be local rather than systemic. Methods of local administration include, but are not limited to, dermal, intradermal, intramuscular, intraperitoneal, subcutaneous, ocular, and intraarticular routes.

Depending on the route of administration, effective doses can be calculated according to the body weight, body surface area, or organ size of the subject to be treated. Optimization of the appropriate dosages can readily be made by one skilled in the art in light of pharmacokinetic data observed in human clinical trials. Alternatively or additionally, the dosage to be administered can be determined from studies using animal models for the particular type of condition to be treated, and/or from animal or human data obtained from agents which are known to exhibit similar pharmacological activities. The final dosage regimen will be determined by the attending surgeon or physician, considering various factors which modify the action of active agent, e.g., the agent's specific activity, the agent's specific half-life in vivo, the severity of the condition and the responsiveness of the patient, the age, condition, body weight, sex and diet of the patient, the severity of any present infection, time of administration, the use (or not) of other concomitant therapies, and other clinical factors.

It will be appreciated that methods of treatment of the present invention can be employed in combination with additional therapies (i.e., a treatment according to the present invention can be administered concurrently with, prior to, or subsequently to one or more desired therapeutics or medical procedures). The particular combination of therapies (therapeutics or procedures) to employ in such a combination regimen will take into account compatibility of the desired therapeutics and/or procedures and the desired therapeutic effect to be achieved.

Thus, for example, in methods where a polymer of the present invention is administered as a viscosupplement to a patient suffering from osteoarthritis, the patient can further receive a non-steroidal or steroidal anti-inflammatory drug and/or may undergo physical therapy. Alternatively or additionally, the inventive polymer can be administered in combination with another viscosupplement, e.g., hyaluronate, chitosan. Alternatively or additionally, the inventive polymer may be administered in combination with another aqueous soluble polymer, e.g., PEG, PEO, PAA. Thus, for example, in methods where a polymer of the present invention can be administered in combination with another aqueous soluble polymer, e.g., PEG, PEO, PAA.

In many methods of the present invention, an inventive polymer can be administered as part of a surgical or clinical procedure. For example, a polymer used as a viscoelastic agent may be administered during cataract surgery. An inventive polymer used as a tissue space filler may be administered during surgery for the treatment of urinary incontinence, during a tissue augmentation procedure for treatment of vocal cord problems, or during a cosmetic procedure, e.g., for wrinkle filling. An inventive polymer used as an anti-adhesive agent may be administered during abdominal or gynecologic surgery to prevent formation of adhesions following surgery.

As mentioned above, methods of treatment of the present invention include administration of an inventive polymer per se or in the form of a pharmaceutical composition. A pharmaceutical composition will generally comprise an effective amount of at least one inventive polymer and at least one pharmaceutically acceptable carrier or excipient.

Pharmaceutical compositions of the present invention can be formulated according to general pharmaceutical practice (see, for example, "Remington's Pharmaceutical Sciences" and "Encyclopedia of Pharmaceutical Technology", J. Swarbrick, and J. C. Boylan (Eds.), Marcel Dekker, Inc: New York, 1988). The optimal pharmaceutical formulation can be varied depending upon the route of administration and desired dosage. Such formulations can influence the physical state, stability, rate of in vivo release, and rate of in vivo clearance of the administered compounds. Formulation will preferably produce liquid or semi-liquid (e.g., gel) pharmaceutical compositions.

Pharmaceutical compositions can be formulated in dosage unit form for ease of administration and uniformity of dosage. The expression "unit dosage form", as used herein, refers to a physically discrete unit of the polymer for the patient to be treated. Each unit contains a predetermined quantity of active material calculated to produce the desired effect. It will be understood, however, that the total dosage of the composition will be decided by the attending physician within the scope of sound medical judgment.

Formulation of pharmaceutical compositions of the present invention will mainly depend on the form of administration chosen. In certain embodiments, injectable formulations (e.g., solutions, dispersions, suspensions, emulsions) will be preferred, for example, for administration to a joint (e.g., knee), an intervertebral disc, the urinary system, or the vocal cord. Injectable formulations can also be used for certain reconstruction or cosmetic procedures. Other procedures can alternatively use gels, lotions, creams, ointments, plasters, bandages, sheets, foams, films, sponges, dressings, or bioadsorbable patches that can be applied to the area in need of treatment.

Physiologically acceptable carriers, vehicles, and/or excipients for use with pharmaceutical compositions of the present invention can be routinely selected for a particular use by those skilled in the art. These include, but are not limited to, solvents, buffering agents, inert diluents or fillers, suspending agents, dispersing or wetting agents, preservatives, stabilizers, chelating agents, emulsifying agents, anti-foaming agents, ointment bases, penetration enhancers, humectants, emollients, and skin protecting agents.

Examples of solvents include water, Ringer's solution, U.S.P., isotonic sodium chloride solution, alcohols, vegetable, marine and mineral oils, polyethylene glycols, propylene glycols, glycerol, and liquid polyalkylsiloxanes. Inert diluents or fillers can be sucrose, sorbitol, sugar, mannitol, microcrystalline cellulose, starches, calcium carbonate, sodium chloride, lactose, calcium phosphate, calcium sulfate, or sodium phosphate. Examples of buffering agents include citric acid, acetic acid, lactic acid, hydrogenophosphoric acid, and diethylamine. Suitable suspending agents include, for example, naturally-occurring gums (e.g., acacia, arabic, xanthan, and tragacanth gum), celluloses (e.g., carboxymethyl-, hydroxyethyl-, hydroxypropyl-, and hydroxypropylmethylcellulose), alginates and chitosans. Examples of dispersing or wetting agents are naturally-occurring phosphatides (e.g., lecithin or soybean lecithin), condensation products of ethylene oxide with fatty acids or with long chain aliphatic alcohols (e.g., polyoxyethylene stearate, polyoxyethylene sorbitol monooleate, and polyoxyethylene sorbitan monooleate).

Preservatives can be added to a pharmaceutical composition of the present invention to prevent microbial contamination that can affect the stability of the formulation and cause infection in the patient. Suitable examples of preservatives include parabens (such as methyl-, ethyl-, propyl-, p-hydroxy-benzoate, butyl-, isobutyl- and isopropyl-paraben), potassium sorbate, sorbic acid, benzoic acid, methyl benzoate, phenoxyethanol, bronopol, bronidox, MDM hydantoin, iodopropylnyl butylcarbamate, benzalconium chloride, cetrimide, and benzylalcohol. Examples of chelating agents include sodium EDTA and citric acid.

Examples of emulsifying agents are naturally-occurring gums, naturally-occurring phosphatides (e.g., soybean lecithin, sorbitan mono-oleate derivatives), sorbitan esters, monoglycerides, fatty alcohols, and fatty acid esters (e.g., triglycerides of fatty acids). Anti-foaming agents usually facilitate manufacture, they dissipate foam by destabilizing the air-liquid interface and allow liquid to drain away from air pockets. Examples of anti-foaming agents include simethicone, dimethicone, ethanol, and ether.

Examples of gel bases or viscosity-increasing agents are liquid paraffin, polyethylene, fatty oils, colloidal silica or aluminum, glycerol, propylene glycol, carboxyvinyl polymers, magnesium-aluminum silicates, hydrophilic polymers (such as, for example, starch or cellulose derivatives), water-swellable hydrocolloids, carragenans, hyaluronates, and alginates. Ointment bases suitable for use in the pharmaceutical compositions of the present invention can be hydrophobic or hydrophilic; and specific examples include paraffin, lanolin, liquid polyalkylsiloxanes, cetanol, cetyl palmitate, vegetable oils, sorbitan esters of fatty acids, polyethylene glycols, and condensation products between sorbitan esters of fatty acids, ethylene oxide (e.g., polyoxyethylene sorbitan monooleate), and polysorbates.

Examples of humectants are ethanol, isopropanol glycerin, propylene glycol, sorbitol, lactic acid, and urea. Suitable emollients include cholesterol and glycerol. Examples of skin protectants include vitamin E, allatoin, glycerin, zinc oxide, vitamins, and sunscreen agents.

In certain embodiments, pharmaceutical compositions of the present invention can, alternatively or additionally, comprise other types of excipients including, thickening agents, bioadhesive polymers, and permeation enhancing agents. Thickening agents are generally used to increase viscosity and improve bioadhesive properties of pharmaceutical compositions. Examples of thickening agents include, but are not limited to, celluloses, polyethylene glycol, polyethylene oxide, naturally occurring gums, gelatin, karaya, pectin, alginic acid, and povidone. In certain embodiments, a thickening agent is selected for its thioxotropic properties (i.e., has a viscosity that is decreased by shaking or stirring). The presence of such as an agent in a pharmaceutical composition allows the viscosity of the composition to be reduced at the time of administration to facilitate its application, e.g., to a skin area to be repaired, and to increase after application so that the composition remains at the site of administration. Permeation enhancing agents are vehicles containing specific agents that affect the delivery of active components through the skin. Permeation enhancing agents are generally divided into two classes: solvents and surface active compounds (amphiphilic molecules). Examples of solvent permeation enhancing agents include alcohols (e.g., ethyl alcohol, isopropyl alcohol), dimethyl formamide, dimethyl sulfoxide, 1-dodecylazocyloheptan-2-one, N-decyl-methyl-sulfoxide, lactic acid, N,N-diethyl-m-toluamide, N-methyl pyrrolidone, nonane, oleic acid, petrolatum, polyethylene glycol, propylene glycol, salicylic acid, urea, terpenes, and trichloroethanol. The surfactant permeation enhancing agent in the present inventive pharmaceutical compositions can be nonionic, amphoteric, cationic, anionic, or zwitterionic. Suitable nonioinic surfactants include poly(oxyethylene)-poly(oxypropylene) block copolymers, commercially known as poloxamers; ethoxylated hydrogenated castor oils; polysorbates, such as Tween 20 or Tween 80. Amphoteric surfactants include quaternized imidazole derivatives, cationic surfactants include cetypyridinium chloride, cationic surfactants include "soap" (fatty acid), alkylsulfonic acid salts (the main component of synthetic detergent, such as linear alkyl benzene sulfonate (LAS)), fatty alcohol sulfate (the main component of shampoo or old neutral detergents), and zwitterionic surfactants include the betaines and sulfobetaines. Injectable formulations can be sterilized, for example, by filtration through a bacterial-retaining filter, GAMA irradiation sterilization, E-Beam irradiation sterilization or by incorporating sterilizing agents in the form of sterile solid compositions which can be dissolved or dispersed in sterile water or other sterile injectable medium prior to use.

In some embodiments, the method of treatment further comprises co-administering a bioactive agent to the subject. The polymer or the polymerizable composition can be administered before, concurrently, or after administration of the bioactive agent. Thus, as used herein, the term "co-administer" refers to administration of two or more agents (e.g., the polymer and the bioactive agent) within a 24 hour period of each other, for example, as part of a clinical treatment regimen. In other embodiments, "co-administer" refers to administration within 12 hours, within 6 hours, within 5 hours, within 4 hours, within 3 hours, within 2 hours, within 1 hour, within 45, within 30 minutes, within 20, within 15 minutes, within 10 minutes, or within 5 minutes of each other. In other embodiments, "co-administer" refers to administration at the same time, either as part of a single formulation or as multiple formulations that are administered by the same or different routes. When the polymer (or the polymerizable composition) and the bioactive agent are administered in different pharmaceutical compositions or at different times, routes of administration can be same or different.

In certain embodiments, the inventive polymer(s) is(are) the only active ingredient(s) in an inventive pharmaceutical composition. In other embodiments, the pharmaceutical composition further comprises one or more bioactive agents. As already mentioned above, a bioactive agent can be associated with the inventive polymer. Alternatively or additionally, a bioactive agent can be added to the composition of polymer and does not form any associations with the polymer. As will be appreciated by one skilled in the art, selection of one or more bioactive agents as component(s) of an inventive pharmaceutical composition will be based on the intended purpose of the pharmaceutical composition (e.g., use in viscosupplementation in the treatment of joints, use as viscoelastics in cataract surgery, use as tissue space fillers for cosmetic procedures, treatment of urinary incontinence or treatment of vocal cord problems, or use as anti-adhesives for wound care). In general, the amount of bioactive agent present in an inventive pharmaceutical composition will be the ordinary dosage required to obtain the desired result through local administration. Such dosages are either known or readily determined by the skilled practitioner in the pharmaceutical and/or medical arts. Examples of bioactive agents that can be present in a pharmaceutical composition of the present invention include, but are not limited to, analgesics, anesthetics, pain-relieving agents, antimicrobial agents, antibacterial agents, antiviral agents, antifungal agents, antibiotics, anti-inflammatory agents, antioxidants, antiseptic agents, antipruritic agents, immuno-stimulating agents, and dermatological agents. Specific examples of suitable bioactive agents are provided and discussed below.

A bioactive agent can be selected for its ability to prevent or alleviate pain, soreness or discomfort, to provide local numbness or anesthesia, and/or to prevent or reduce acute post-operative surgical pain. Thus, suitable pain relieving agents include, but are no limited to, compounds, molecules or drugs which, when applied locally, have a temporary analgesic, anesthetic, numbing, paralyzing, relaxing or calming effect.

Analgesics suitable for use in the present invention include non-steroidal, anti-inflammatory drugs (NSAIDs). NSAIDs have analgesic, antipyretic and anti-inflammatory activity. They act peripherally to provide their analgesic effect by interfering with the synthesis of prostaglandin, through cyclooxygenase (COX) inhibition. There are many different types of NSAIDs, including aspirin and other salicylates. Examples include, but are not limited to, ibuprofen, naproxen, sulindac, diclofenac, piroxicam, ketoprofen, diflunisal, nabumetone, etodolac, oxaprozin, and indomethacin. Aspirin is anti-inflammatory when administered in high doses, otherwise it is just a pain killer like acetaminophen. Acetaminophen has similar analgesic and antipyretic effects to the NSAIDs, but does not provide an anti-inflammatory effect. Several of the more potent NSAIDs have been developed into topical products for local administration to painful areas of the body.

Analgesics suitable for use in the present invention also include opioids. As used herein, the term "opioid" refers to any agonists or antagonists of opioid receptors such as the μ-, κ-, and δ-opioid receptors and different subtypes. Examples of opioids include, but are not limited to, alfentanil, allylprodine, alphaprodine, amiphenazole, anileridine, benzeneacetamine, benzoylhydrazone, benzylmorphine, benzitramide, nor-binaltorphimine, bremazocine, buprenorphine, butorphanol, clonitazene, codeine, cyclazocine, desomorphine, dextromoramide, dezocine, diampromide, dihydrocodeine, dihydrocodeine enol acetate, dihydromorphine, dimenoxadol, dimepheptanol, dimethyl-thiambutene, dioxaphetyl butyrate, dipipanone, diprenorphine, eptazocine, ethoheptazine, ethylketocyclazocine, ethylmethylthiambutene, etonitazene, etorphine, fentanyl, hydrocodone, hydromorphone, hydroxypethidine, isomethadone, ketobemidone, levallorphan, levorphanol, lofentanil, loperamide, meperidine, meptazinol, metazocaine, methadone, metopon, morphine, morphiceptin, myrophine, nalbuphine, nalmefene, nalorphine, naltrindole, naloxone, naltrexone, narceine, nicomorphine, norlevorphanol, normethadone, normorphine, norpipanone, opium, oxycodone, oxymorphone, papaveretum, papaverine, pentazocine, phenadoxone, phenazocine, phenoperidine, piminodine, piperidine, pirtramide, proheptazine, promedol, propiram, propoxyphene, remifentanil, spiradoline, sufentanil, tilidine, trifluadom, and active derivatives, prodrugs, analogs, pharmaceutically acceptable salts, or mixtures thereof. Examples of peptide opioids include, but are not limited to, [Leu$^5$]enkephalin, [Met$^5$]enkephalin, DynorphinA, Dynorphin B, α-Neoendorphin, β-Neoendorphin, $β_h$-Endorphin, Deltorphin II, Morphiceptin, and active derivatives, analogs, pharmaceutically acceptable salts, or mixtures thereof.

Tricyclic antidepressants can be useful as adjuvant analgesics. They are known to potentiate the analgesic effects of opioids (V. Ventafridda et al., Pain, 1990, 43: 155-162) and to have innate analgesic properties (M. B. Max et al., Neurology, 1987, 37: 589-596; B. M. Max et al., Neurology, 1988, 38: 1427-1432; R. Kishore-Kumar et al., Clin. Pharmacol. Ther., 1990, 47: 305-312). Tricyclic antidepressants include, but are not limited to, amitriptyline, amoxapine, clomipramine, desipramine, doxepin, imipramine, nortriptyline, protriptyline, and trimipramine.

Anesthetics that are suitable for use in the practice of the present invention include sodium-channel blockers. Examples of sodium-channel blockers include, but are not limited to, ambucaine, amolanone, amylcaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dyclonine, ecogonidine, ecogonine, etidocaine, euprocin, fenalcomine, formocaine, hexylcaine, hydroxyteteracaine, isobutyl p-aminobenzoate, leucinocaine, levoxadrol, lidocaine, mepivacaine, meprylcaine, metabutoxycaine, methyl chloride, myrtecaine, naepaine, octacaine, orthocaine, oxethazaine, parenthoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, and active derivatives, prodrugs, analogs, pharmaceutically acceptable salts, or mixtures thereof.

Local anesthetics with different pharmacodynamics and pharmacokinetics can be combined in an inventive pharmaceutical composition in order to improve the effectiveness and tolerance of the composition. For example, an inventive composition can comprise an euctectic mixture of lidocaine and prilocaine, or a mixture of lidocaine and tetracaine. It has been reported (see, for example, U.S. Pat. Nos. 5,922,340 and 6,046,187) that co-administration of a glucocorticosteroid and a local anesthetic can prolong or otherwise enhance the effect of local anesthetics. Examples of glucocorticosteroids include dexamethazone, cortisone, hydrocortisone, prednisone, prednisolone, beclomethasone, betamethasone, flunisolide, fluocinolone, acetonide, fluocinonide, triamcinolone, and the like.

Locally acting vasoconstrictive agents are also known to provide effective enhancement of local anesthesia, especially when administered through controlled release. Examples of vasoconstrictor agents include, but are not limited to, catechol amines (e.g., epinephrine, norepinephrine and dopamine); metaraminol, phenylephrine, sumatriptan and analogs, alpha-1 and alpha-2 adrenergic agonists, such as, for example, clonidine, guanfacine, guanabenz, and dopa (i.e., dihydroxyphenylalanine), methyldopa, ephedrine, amphetamine, methamphetamine, methylphenidate, ethylnorepinephrine ritalin, pemoline, and other sympathomimetic agents.

Anti-infective agents are compounds, molecules or drugs which, when administered locally, have an anti-infective activity (i.e., they can decrease the risk of infection; prevent infection; or inhibit, suppress, combat or otherwise treat infection). Anti-infective agents include, but are not limited to, antiseptics, antimicrobial agents, antibiotics, antibacterial agents, antiviral agents, antifungal agents, anti-protozoan agents, and immunostimulating gents.

Antiviral agents suitable for use in the present invention include RNA synthesis inhibitors, protein synthesis inhibitors, immunostimulating agents, and protease inhibitors. Antiviral agents can, for example, be selected from the group consisting of acyclovir, amantadine hydrochloride, foscarnet sodium, ganeiclovir sodium, phenol, ribavirin, vidarabine, and zidovudine.

Examples of suitable antifungal agents include lactic acid, sorbic acid, Amphotericin B, Ciclopirox, Clotrimazole, Enilconazole, Econazole, Fluconazole, Griseofulvin, Halogropin, Introconazole, Ketoconazole, Miconazole, Naftifine, Nystatin, Oxiconazole, Sulconazole, Thiabendazole, Terbinafine, Tolnaftate, Undecylenic acid, Mafenide, Silver Sulfadiazine, and Carbol-Fushsin.

Antibiotics and other antimicrobial agents can be selected from the group consisting of bacitracin; the cephalosporins (such as cefadroxil, cefazolin, cephalexin, cephalothin, cephapirin, cephradine, cefaclor, cefamandole, cefonicid, ceforanide, cefoxitin, cefuroxime, cefoperazone, cefotaxime, cefotetan, ceftazidime, ceftizoxime, ceftriaxone, and meropenem); cycloserine; fosfomycin, the penicillins (such as amdinocillin, ampicillin, amoxicillin, azlocillin, bacamipicillin, benzathine penicillin G, carbenicillin, cloxacillin, cyclacillin, dicloxacillin, methicillin, mezlocillin, nafcillin, oxacillin, penicillin G, penicillin V, piperacillin, and ticarcillin); ristocetin; vancomycin; colistin; novobiocin; the polymyxins (such as colistin, colistimathate, and polymyxin B); the aminoglycosides (such as amikacin, gentamicin, kanamycin, neomycin, netilmicin, paromomycin, spectinomycin, streptomycin, and tobramycin), the tetracyclines (such as demeclocycline, doxycycline, methacycline, minocycline, and oxytetracycline); carbapenems (such as imipenem); monobactams (such as aztreonam); chloramphenicol; clindamycin; cycloheximide; fucidin; lincomycin; puromycin; rifampicin; other streptomycins; the macrolides (such as erythromycin and oleandomycin); the fluoroquinolones; actinomycin; ethambutol; 5-fluorocytosine; griseofulvin; rifamycins; the sulfonamides (such as sulfacytine, sulfadiazine, sulfisoxazole, sulfamethoxazole, sulfamethizole, and sulfapyridine); and trimethoprim.

Other antibacterial agents include, but are not limited to, bismuth containing compounds (such as bismuth aluminate, bismuth subcitrate, bismuth subgalate, and bismuth subsalicylate); nitrofurans (such as nitrofurazone, nitrofurantoin, and furozolidone); metronidazole; tinidazole; nimorazole; and benzoic acid.

Antiseptic agents can be selected from the group consisting of benzalkonium chloride, chlorhexidine, benzoyl peroxide, hydrogen peroxide, hexachlorophene, phenol, resorcinol, and cetylpyridinium chloride.

The risk of infection is directly influenced by a suppressed immune system due to disease or medication. Immunostimulating agents are compounds, molecules or drugs that stimulate the immune system of a patient to respond to the presence of a foreign body, for example, by sending macrophages to the infected site(s). Immunostimulating agents suitable for use in the present invention can be selected from a wide range of therapeutic agents, such as interleukin 1 agonists, interleukin 2 agonists, interferon agonists, RNA synthesis inhibitors, and T cell stimulating agents.

Anti-inflammatory agents are compounds, molecules or drugs which, when administered locally, have an anti-inflammatory activity (i.e., they can prevent or reduce the duration and/or severity of inflammation; prevent or reduce injury to cells at the injured/damaged site; prevent or reduce damage or deterioration of surrounding tissue due to inflammation; and/or provide relief from at least one of the manifestations of inflammation such as erythema, swelling, tissue ischemia, itching, fever, scarring, and the like).

Anti-inflammatory agents include NSAIDs and steroidal anti-inflammatory agents. Examples of NSAIDs can be found above. Examples of steroidal anti-inflammatory agents include, but are not limited to, aclomethasone dipropionate, flunisolide, fluticasone, budesonide, triamcinolone, triamcinoline acetonide, beclomethasone diproprionate, betamethasone valerate, betamethasone diproprionate, hydrocortisone, cortisone, dexamethason, mometasone furoate, prednisone, methylprednisolone aceponate, and prednisolone.

Anti-inflammatory agents can, alternatively or additionally, be selected from the wide variety of compounds, molecules, and drugs exhibiting antioxidant activity. Antioxidants are agents that can prevent or reduce oxidative damage to tissue. Examples of antioxidants can include, but are not limited to, vitamin A (retinal), vitamin B (3,4-didehydroretinol), vitamin C (D-ascorbic acid, L-ascorbic acid), α-carotene, β-carotene, γ-carotene, δ-carotene, vitamin E (α-tocopherol), β-tocopherol, γ-tocopherol, δ-tocopherol, tocoquinone, tocotrienol, butylated hydroxy anisole, cysteine, and active derivatives, analogs, precursors, prodrugs, pharmaceutically acceptable salts or mixtures thereof.

In certain embodiments, the bioactive agent is a biomolecule that is naturally present in the body and/or that is naturally secreted at an injured or damaged site (i.e., body area) and plays a role in the natural healing process. As will be apparent to those of ordinary skill in the art, variants, synthetic analogs, derivatives, and active portions of these biomolecules can, alternatively, be used in the inventive compositions as long as they exhibit substantially the same type of property/activity as the native biomolecule. Such variants, synthetic analogs, derivatives or active portions are intended to be within the scope of the term "bioactive agents". Bioactive biomolecules can be extracted from mammalian tissues and used in inventive pharmaceutical compositions either crude or after purification. Alternatively, they can be prepared chemically or by conventional genetic engineering techniques, such as via expression of synthetic genes or of genes altered by site-specific mutagenesis.

Examples of suitable bioactive biomolecules include cytokines and growth factors. Cytokines and growth factors are polypeptide molecules that regulate migration, proliferation, differentiation and metabolism of mammalian cells. A diverse range of these biomolecules have been identified as potentially playing an important role in regulating healing. Examples of cytokines include, but are not limited to, interleukins (ILs) (e.g., IL-1, IL-2, IL-4 and IL-8), interferons (IFNs) (e.g., IFN-α, IFN-β, and IFN-γ), and tumor necrosis factors (e.g., TNF-α), or any variants, synthetic analogs, active portions or combinations thereof. Examples of growth factors include, but are not limited to, epidermal growth factors (EGFs), platelet-derived growth factors (PDGFs), heparin binding growth factor (HBGFs), fibroblast growth factors (FGFs), vascular endothelial growth factors (VEGFs), insulin-like growth factors (IGFs), connective tissue activating peptides (CTAPs), transforming growth factors alpha (TGF-α) and beta (TGF-β), nerve growth factor (NGFs), colony stimulating factors (G-CSF and GM-CSF), and the like, or any variants, synthetic analogs, active portions or combinations thereof.

Other examples of suitable bioactive biomolecules include proteoglycans, or portions thereof. Proteoglycans are protein-carbohydrate complexes characterized by their glycosaminoglycan (GAG) component. GAGs are highly charged sulfated and carboxylated polyanionic polysaccharides. Examples of GAGs suitable for use in pharmaceutical compositions of the present invention include, but are not limited to, hyaluronan, chondroitin sulfate, dermatan sulfate, heparan sulfate, and keratan sulfate.

Still other examples of suitable bioactive biomolecules include adhesion molecules. Adhesion molecules constitute a diverse family of extracellular and cell surface glycoproteins involved in cell-cell and cell-extracellular matrix adhesion, recognition, activation, and migration. Adhesion molecules are essential to the structural integrity and homeostatic functioning of most tissues, and are involved in a wide range of biological processes, including embryogenesis, inflammation, thrombogenesis, and tissue repair. Adhesion molecules include matricellular proteins (e.g., thrombospondins and tenascins), and cell surface adhesion molecules (e.g., integrins, selectins, cadherins, and immunoglobulins).

Exemplary Uses of the Polymers, Compositions and Methods Disclosed Herein

As noted above, the compositions, polymers and methods disclosed herein can be used for a variety of indications, with various dosages and routes of administration, and in conjunction with other therapies to yield a combination therapy.

A variety of indications exist for humans and other non-human animals. The human medical need for injectable biomaterials to augment tissue mechanical properties is widespread, and many of the same indications apply to non-human animals in veterinary settings, for example in the treatment of domestic animals, farm animals, entertainment animals, and the like.

In some embodiments, the compositions, polymers and methods disclosed herein can be used as a mechanical supplement to the native components of tissues that confer non-optimal mechanical properties. For example, mechanical properties of cartilage can be improved following treatment of diseased, damaged, or otherwise non-optimal cartilage in a variety of animal joints. As examples, intervertebral discs, and articular cartilage in synovial joints such as the knee, hip, and metacarpophalangeal joint, can be treated.

Polymers of the present invention, without interpenetrating the animal's tissue, can be used as viscosupplements. As already mentioned above, viscosupplementation is a procedure involving injection of gel-like substances (generally hyaluronates, HAs) into a joint to supplement the viscous properties of synovial fluid. HA injections have been found to relieve pain in many osteoarthritis patients, with HAs of higher molecular weights (i.e., higher viscosity) showing better efficacy than those with lower molecular weights (i.e., lower viscosity). However, due to their short lifetime within the joint (about a couple of days), hyaluronate preparations currently available have only limited long-term benefit to the patient and require injection of large quantities of preparation and/or repeated injections.

In some embodiments, the compositions, polymers and methods disclosed herein can be used for viscoelastics useful in surgery. Viscoelastic agents used in surgery can perform a number of different functions, including, without limitation, maintenance and support of soft tissue, tissue manipulation, lubrication, tissue protection, and adhesion prevention. As will be appreciated by one skilled in the art, the rheological properties of the polymers will necessarily affect their ability to perform these functions, and, as a result, their suitability for certain surgical procedures.

Viscoelastics are, for example, used in opthhalmic surgery, such as cataract surgery. Cataracts, which are opacities of the natural ocular lens, can strike people in their 40s and 50s, but they occur most commonly in those over age 60—with a rapid increase in prevalence after that. More than 50% of all Americans 65 and older have cataracts, increasing to 70% among those over 75. In order to improve eyesight, the cataractous lens is surgically removed from the eye and an artificial intraocular lens is inserted in its place. Viscoelastics were introduced in the early 1980s in response to the observation that, during cataract surgery, the underside of the cornea was often damaged due to contact with instruments, devices, fluid bubbles, and intraocular lenses. Because the cells in this region cannot regrow, there was a need to protect them. Thus, during these surgical procedures, viscoelastic materials are typically injected into the anterior chamber of the eye to prevent collapse of the anterior chamber and to protect the delicate eye tissues from damage resulting from physical manipulation. Viscoelastics also gently inflate spaces inside the eye, making it easier to maneuver various tools inside the eye.

Other examples of ocular surgery procedures that employ viscoelastics include trabeculectomy (i.e., glaucoma filtration surgery), and vitrectomy (i.e., replacement of the vitrous, a normally clear, gel-like substance that fills the center of the eye), which may be performed to clear blood and debris from the eye, to remove scar tissue, or to alleviate traction on the retina.

In some embodiments, the compositions, polymers and methods disclosed herein can be used for tissue space fillers in any of a wide variety of soft tissue augmentation procedures, including, but not limited to, reconstruction or cosmetic enhancement, treatment for stress urinary incontinence, and treatment of vocal cord problems (e.g., paralysis, atrophy or paresis).

Tissue space fillers are used to correct deformities or to reconstruct areas that are missing or defective due to surgical intervention, trauma, disease, aging, or congenital condition. Examples of reconstruction or cosmetic enhancement procedures include, but are not limited to, dermal tissue augmentation; filling of lines, folds, wrinkles, minor facial depressions, cleft lips and the like, especially in the face and neck; correction of minor deformities due to aging or disease, including in the hands and feet, fingers and toes; dermal filling of sleep lines and expression lines; replacement of dermal and subcutaneous tissue lost due to aging; lip augmentation; filling of crow's feet and the orbital groove around the eye; breast augmentation; chin augmentation; augmentation of the cheek and/or nose; filling of indentations in the soft tissue, dermal or subcutaneous, due to, e.g., overzealous liposuction or other trauma; filling of acne or traumatic scars and rhytids; filling of nasolabial lines, nasoglabellar lines and infraoral lines.

Urinary incontinence is an underserved market: there are approximately 40 million people in the U.S. that suffer from urinary incontinence, yet there are only about 250,000 procedures performed each year. Collagen bulking agents are generally used to treat urinary incontinence. They are injected into tissue surrounding the urethra to tighten the urethral sphincter and stop urine from leaking. However, these agents require several injections across multiple appointments. They also have a poor cure rate of approximately 27% to 36%. If the procedure is successful, the success is only temporary as the collagen reabsorbs into the surrounding tissue. A carbon-bead based product (Durasphere, Advanced UroScience, Inc., Saint Paul, Minn.) entered the market in 1999 with the promise of permanence (due to less degradation of the material) but clinical data have not supported those claims and the product appears to have similar performance to collagen. Q-Med AB (Uppsala, Sweden) recently introduced Zuidex$^T$, an HA gel which is reinforced by the addition of dextranomer, that promises immediate effects and ease of administration. New biomaterials, such as the inventive dendritic polymers, could impact the market if they require less material, fewer injections and had better longevity.

In vocal cord disorders such as paralysis, atrophy and paresis, one or both vocal cords are weakened and lack the ability to close and thus vibrate properly, resulting in a soft, breathy or weak voice. The affected cord may also allow food and liquids into the trachea or lungs causing difficulty with swallowing and coughing. Vocal cord paralysis may be caused by chest and neck surgery, brain injury, neck injury, lung or thyroid cancer, certain neurologic conditions, or a viral infection. In older people, vocal cord atrophy is a common problem affecting voice production. Standard treatments of vocal cord disorders include voice therapy and surgery. In surgery, doctors attempt to add bulk to the injured vocal cord by injecting a substance (e.g., fat or collagen) into the cord. This moves the injured cord closer to the non-injured cord, allowing for better contact and improved speech and swallowing. Other substances are being studied for vocal cord augmentation including silicone paste, Teflon paste, calcium hydroxylapatite, and hyaluronic acid.

In some embodiments, the compositions, polymers and methods disclosed herein can be used as anti-adhesives. Anti-adhesives are devices that keep tissues from abnormally joining together following surgery. These abnormal unions, called adhesions, may form between an incision in the abdominal wall and the small bowel after abdominal surgery, leading to chronic pain or even bowel obstruction. Adhesions also occur following gynecological surgery, resulting in fibrous scarring that may involve the uterus, bladder, bowel or ovaries and fallopian tubes, and that can, in the worst case, lead to infertility. A wide variety of approaches, including use of steroids, non-steroidal anti-inflammatory drugs and minimally invasive surgical techniques, have been used in an attempt to prevent adhesions. However, biodegradable barriers appear to be the most promising tools available for keeping adjacent organs separate following surgery (P. B. Arnold et al., Fertil. Steril., 2000, 73: 157-161). Examples of such barriers include, but are not limited to, anti-adhesive membranes that may be laid on localized areas of the peritoneum, such as Interceed Absorbable Adhesion Barrier (Johnson & Johnson Patient Care Inc., New Brunswick, N.J.); Preclude Surgical Membrane (E. L. Gore Co., Flagstaff, Ariz.) and Seprafilm Surgical Membrane (Genzyme, Cambridge, Mass.); and viscous gels, such as Hyskon (Pharmacia, Piscataway, N.J.); Sepracoat (Genzyme) and Intergel (Lifecore Biomedical, Inc., Chaska, Minn.). Additional uses and applications of the inventive polymers will be immediately apparent to those skilled in the art.

Without wishing to be bound by a theory, the compositions, polymers and methods disclosed herein can enhance or increase the compressive strength of the treated tissue. For example, the compressive strength can be an increase in the equilibrium compressive modulus of the tissue, and/or an increase in the peak force modulus of the tissue, and/or an increase in the dynamic modulus of the tissue, and/or an increase in the magnitude of peak force resisted of the tissue. Generally, the peak force resisted is usually compared when a compression is applied to a tissue at a certain strain rate and a certain total strain is achieved. In other words, the peak force resisted is the force the tissue exerts when one compress it to a certain percentage of its original length, at a certain compression speed; a greater magnitude of peak force resisted indicates a stronger, less compressible material.

In some embodiments, the compressive strength of a tissue treated with the compositions, polymers, and methods disclosed herein is at least 5%, 10%, 15%, 20%, 25%, 30%, 35%, 40%, 45%, 50%, 55%, 60%, 65%, 70%, 75%, 80%, 85%, 90%, 95%, 1-fold, 1.5-folds, 2-folds, 5-folds, 10-folds or higher than a untreated tissue. In some embodiments, the compressive strength of a diseased or damaged tissue treated with the compositions, polymers, and methods disclosed herein is within 20%, 15%, 10%, 7.5%, 5%, 2.5%, 1%, 0.5% or less of the compressive strength of the healthy or normal tissue.

In some embodiments, the compositions, polymers and methods disclosed herein can decrease or inhibit exudation of physiological fluid from the treated tissue. For example, the compositions, polymers and methods disclosed herein can decrease exudation of physiological fluid from the treated tissue by at least 5%, 10%, 15%, 20%, 25%, 30%, 35%, 40%, 45%, 50%, 55%, 60%, 65%, 70%, 75%, 80%, 85%, 90%, 95%, or up to and including a 100% decrease (e.g. absent level as compared to a reference sample), or any decrease between 5-99% as compared to the untreated tissue.

In some embodiments, the compositions, polymers and methods disclosed herein can enhance or increase affinity of the treated tissue to imbibe physiological fluid. For example, the compositions, polymers and methods disclosed herein can enhance affinity of the treated tissue to imbibe physiological fluid by at least 5%, 10%, 15%, 20%, 25%, 30%, 35%, 40%, 45%, 50%, 55%, 60%, 65%, 70%, 75%, 80%, 85%, 90%, 95%, 1-fold, 1.5-folds, 2-folds or higher relative to the untreated tissue.

In some embodiments, the compositions, polymers and methods disclosed herein can decrease or inhibit the treated tissue's tendency to wear, deteriorate, or degenerate under compressive or shear loading. For example, the compositions, polymers and methods disclosed herein can decrease the treated tissue's tendency to wear, deteriorate, or degenerate under compressive or shear loading by at least 5%, 10%, 15%, 20%, 25%, 30%, 35%, 40%, 45%, 50%, 55%, 60%, 65%, 70%, 75%, 80%, 85%, 90%, 95%, or up to and including a 100% decrease (e.g. absent level as compared to a reference sample), or any decrease between 5-99% as compared to the untreated tissue.

In some embodiments, the compositions, polymers and methods disclosed herein can decrease or inhibit the treated tissue's coefficient of friction. For example, the compositions, polymers and methods disclosed herein can decrease the treated tissue's coefficient of friction by at least 5%, 10%, 15%, 20%, 25%, 30%, 35%, 40%, 45%, 50%, 55%, 60%, 65%, 70%, 75%, 80%, 85%, 90%, 95%, or up to and including a 100% decrease (e.g. absent level as compared to a reference sample), or any decrease between 5-99% as compared to the untreated tissue.

In some embodiments, the compositions, polymers and methods disclosed herein can enhance or increase lubricity of the treated tissue. For example, the compositions, polymers and methods disclosed herein can increase lubricity of the treated tissue to imbibe physiological fluid by at least 5%, 10%, 15%, 20%, 25%, 30%, 35%, 40%, 45%, 50%, 55%, 60%, 65%, 70%, 75%, 80%, 85%, 90%, 95%, 1-fold, 1.5-folds, 2-folds or higher relative to the untreated tissue.

Some embodiments of the invention are listed in the following numbered paragraphs: paragraph 1. A polymer synthesized in situ, wherein the polymer comprises one or more monomers selected from sugar molecules and polyethylene glycols comprising an ethylenically unsaturated group, compounds of Formula I-XIV, compounds of Formula XVII-XXXVII, or any combinations thereof, wherein compounds of Formulas I-XIV are:

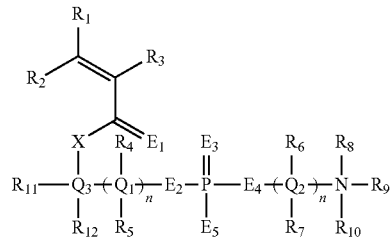

Formula I

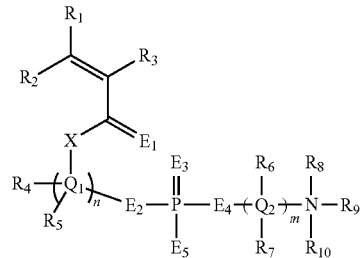

Formula II

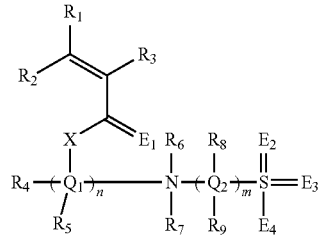

Formula III

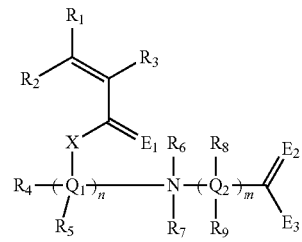

Formula IV

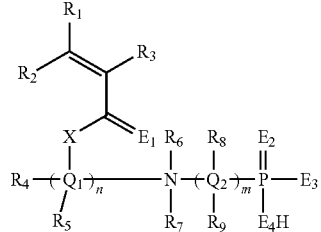

Formula V

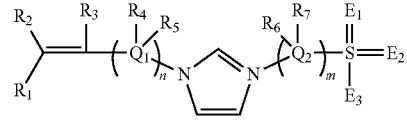

Formula VI

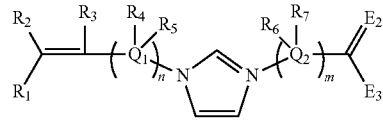

Formula VII

-continued
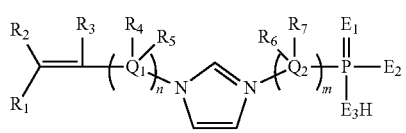
Formula VIII
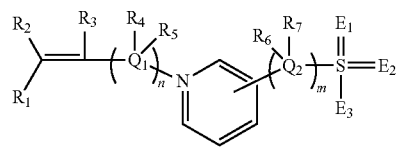
Formula IX
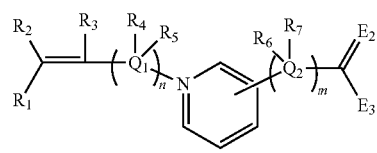
Formula X
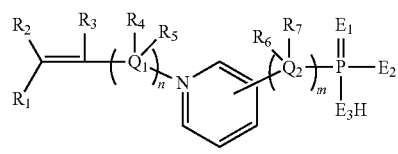
Formula XI
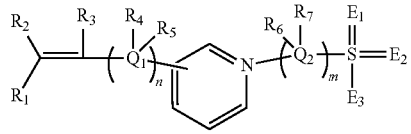
Formula XII
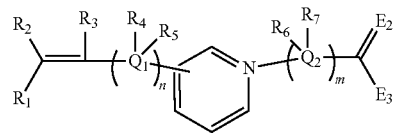
Formual XIII
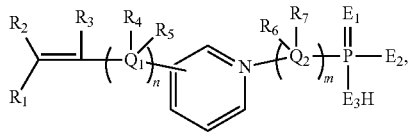
Formula XIV
compounds of Formulas XVII-XXXVII are:
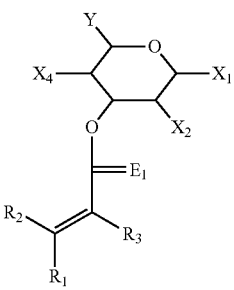
XVII
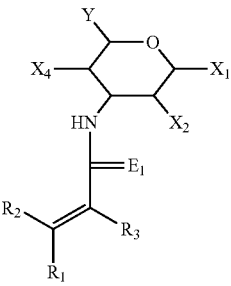
XVIII
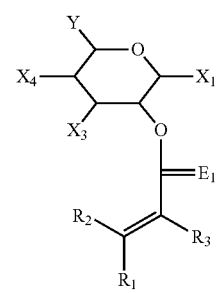
XIX
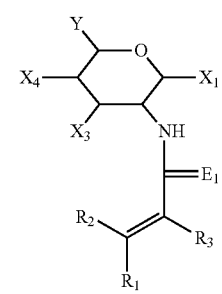
XX
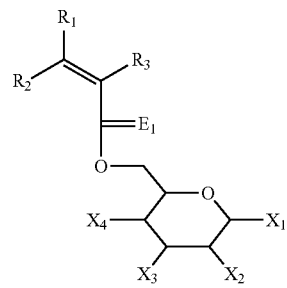
XXI
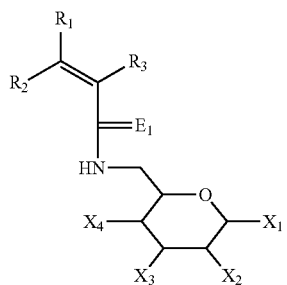
XXII XXIII
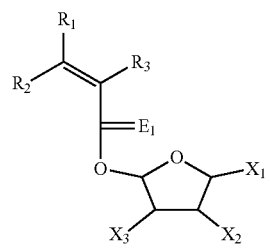
XXIV
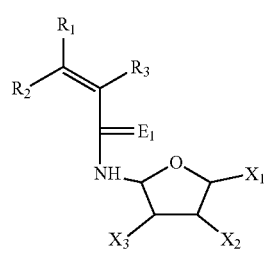
XXV
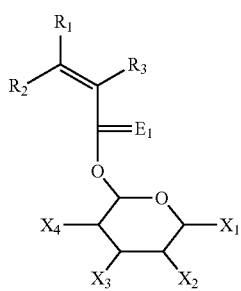
XXVI
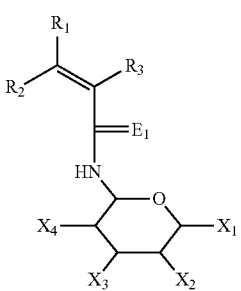
XXVII
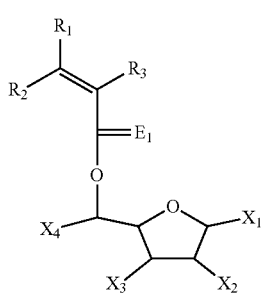
XXVIII
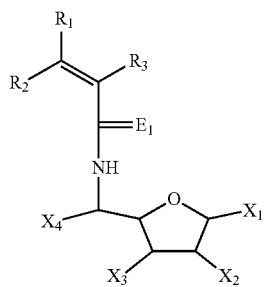
XXIX
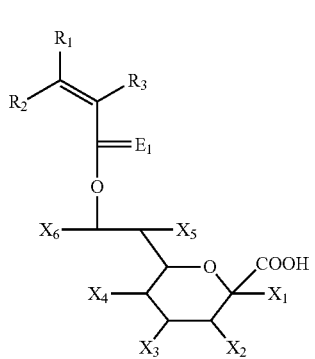
XXX
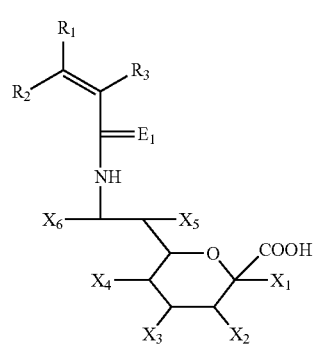
XXXI
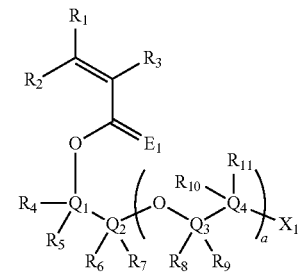
XXXII
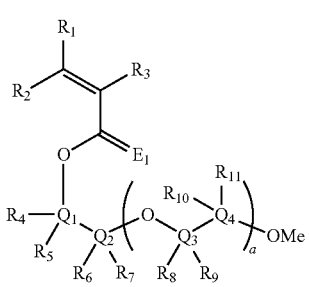

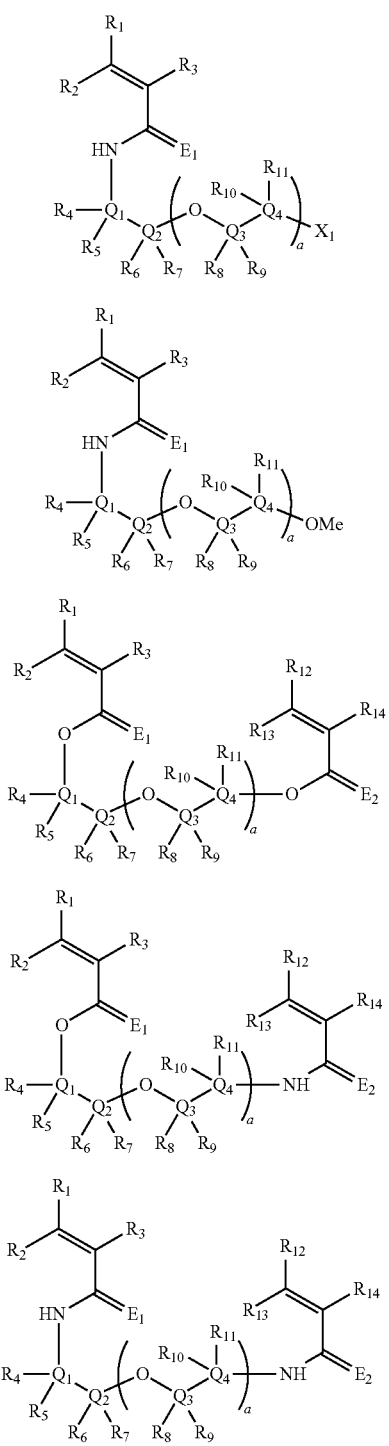

XXXIII

XXXIV

XXXV

XXXVI

XXXVII wherein:
$R_1$, $R_2$, $R_4$, $R_5$, $R_6$, $R_7$, $R_8$, $R_9$, $R_{10}$, $R_{11}$, $R_{12}$, $R_{13}$, and $R_{14}$ are each independently selected from the group consisting of alkyl, alkenyl, alkynyl, H, halide, ether-linked alkyl, ether-linked alkenyl, ether-linked alkynyl;

$R_3$ is selected from the group consisting of hydrogen, a straight or branched alkyl, cycloalkyl, aryl, olefin, silyl, alkylsilyl, arylsilyl, alkylaryl, arylalkyl, methoxy, ethoxy, amino, or fluorocarbon chain of 1-50 carbons, wherein each alkyl, cycloalkyl, aryl, olefin, silyl, alkylsilyl, arylsilyl, alkylaryl, arylalkyl, or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents;

X is O, S, Se, or NH;

$X_1$, $X_2$, $X_3$, $X_4$, $X_5$, and $X_6$ are independently selected from the group consisting of OH, $OSO_3H$, $OSO_3^-J^+$, $OPO_3H_2$, $OPO_3H^-J^+$, $OPO_3^{2-}2J^+$, $OPO_3^{2-}Z^{2+}$, $NH_2$, and $NC(O)CH_3$;

Y is independently for each occurrence H, $CH_2OH$, COOH, $COO^-J^+$, $CH_2OSO_3H$, $CH_2OSO_3^-J^+$, $CH_2OPO_3H_2$, $CH_2OPO_3H^-J^+$, $CH_2OPO_3^{2-}2J^+$, or $CH_2OPO_3^{2-}Z^{2+}$;

$J^+$ is a monovalent cation;

$Z^{2+}$ is a divalent cation;

$Q_1$, $Q_2$ and $Q_3$ are each independently selected from the group consisting of C, Si, or ethylene glycol, or a hydrophilic monomer;

$E_1$, $E_2$, $E_3$, $E_4$, $E_5$ are each independently selected from the group consisting of O, S, Se, or NH;

n and m can each independently range from 0-14; and a is an integer from 0-1200.

paragraph 2. The polymer of paragraph 1, wherein the monomer comprises a functional group selected from the group consisting of carboxylic acid, carboxylate, sulfate, sulfonate, sulfuric acid, phosphate, phosphonate, phosphoric acid, amine, ammonium, phosphine, phosphonium, and ether.

paragraph 3. The polymer of paragraph 1 or 2, wherein the monomer is charged.

paragraph 4. The polymer of any of paragraphs 1-3, wherein the monomer is zwitterionic.

paragraph 5. The polymer of any of paragraphs 1-4, wherein the monomer comprises a betaine.

paragraph 6. The polymer of any of paragraphs 1-5, wherein the monomer comprises a phosphorylcholine.

paragraph 7. The polymer of any of paragraphs 1-6, wherein the monomer is hydrophilic.

paragraph 8. The polymer of any of paragraphs 1-7, wherein the monomer is selected from the group consisting of N,N-dimethyl-N-acryloyloxyethyl-N-(3-sulfopropyl)-ammonium betaine, N,N-dimethyl-N-acrylamidopropyl-N-(2-carboxymethyl)-ammonium betaine, N,N-dimethyl-N-acrylamidopropyl-N-(3-sulfopropyl)-ammonium betaine, N,N-dimethyl-N-acrylamidopropyl-N-(2-carboxymethyl)-ammonium betaine, 2-(methylthio)ethyl methacryloyl-S-(sulfopropyl)-sulfonium betaine, 2-[(2-acryloylethyl) dimethylammonio]ethyl 2-methyl phosphate, 2-(acryloyloxyethyl)-2'-(trimethylammonium)ethyl phosphate, [(2-acryloylethyl)dimethylammonio]methyl phosphonic acid, 2-methacryloyloxyethyl phosphorylcholine (MPC), 2-[(3-acrylamidopropyl)dimethylammonio]ethyl 2'-isopropyl phosphate (AAPI), 1-vinyl-3-(3-sulfopropyl) imidazolium hydroxide, (2-acryloxyethyl)carboxymethyl methylsulfonium chloride, 1-(3-sulfopropyl)-2-vinylpyridinium betaine, N-(4-sulfobutyl)-N-methyl-N,N-diallylamine ammonium betaine (MDABS), and N,N-diallyl-N-methyl-N-(2-sulfoethyl)ammonium betaine, and any combination thereof.

paragraph 9. The polymer of any of paragraphs 1-8, further comprising one or more crosslinkers.

paragraph 10. The polymer of paragraph 9, wherein the cross-linker is selected from a compound of Formula XV or XVI:

Formula XV

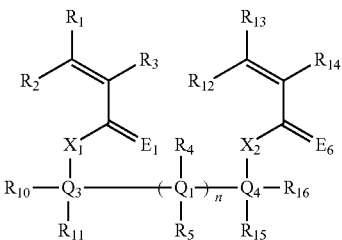

Formula XVI

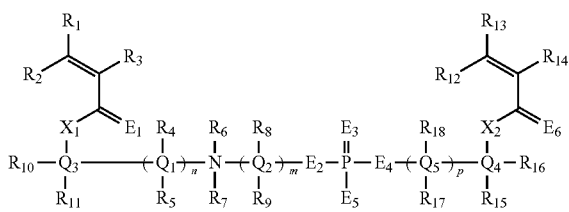

and any combination thereof, wherein:

$R_1$, $R_2$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ are each independently selected from the group consisting of alkyl, alkenyl, alkynyl, H, halide, ether-linked alkyl, ether-linked alkenyl, ether-linked alkynyl;

$R_3$ is selected from the group consisting of hydrogen, a straight or branched alkyl, cycloalkyl, aryl, olefin, silyl, alkylsilyl, arylsilyl, alkylaryl, arylalkyl, methoxy, ethoxy, amino, or fluorocarbon chain of 1-50 carbons, wherein each alkyl, cycloalkyl, aryl, olefin, silyl, alkylsilyl, arylsilyl, alkylaryl, arylalkyl, or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents;

$X_1$ and $X_2$ are each independently selected from O, S, Se, and NH;

$Q_1$, $Q_2$, $Q_3$, $Q_4$, and $Q_5$ are each independently C, Si, ethylene glycol, or a hydrophilic monomer;

$E_1$, $E_2$, $E_3$, $E_4$, $E_5$, and $E_6$ are each independently selected from the group consisting of O, S, Se, or NH;

n, m, and p are integers, each independently ranging from 0-15.

paragraph 11. The polymer of paragraph 10, wherein the cross-linker is ethylene glycol dimethacrylate (EGDMA) or methacryloyloxyethyl-N-(2-methacryloyloxyethyl phosphorylcholine).

paragraph 12. The polymer of any of paragraphs 1-11, wherein the polymer is a gel or hydrogel.

paragraph 13. The polymer of any of paragraphs 1-12, wherein the polymer is in solution.

paragraph 14. The polymer of paragraph 13, wherein the solution is viscous.

paragraph 15. The polymer of paragraph 13, wherein the solution is non-viscous.

paragraph 16. The polymer of any of paragraphs 1-15, wherein the site of in situ polymer formation includes cartilage tissue.

paragraph 17. A composition comprising an interpenetrating network comprising a first network and a second network, wherein the first network comprises cartilage tissue, and wherein the second network comprises a polymer of any of paragraphs 1 to 16.

paragraph 18. A polymer synthesized ex situ, wherein the polymer comprises one or more monomers selected from sugar molecules and polyethylene glycols comprising an ethylenically unsaturated group, compounds of Formula I-XIV, compounds of Formula XVII-XXXVII, or any combinations thereof.

paragraph 19. The polymer of paragraph 18, wherein the monomer comprises a functional group selected from the group consisting of carboxylic acid, carboxylate, sulfate, sulfonate, sulfuric acid, phosphate, phosphonate, phosphoric acid, amine, ammonium, phosphine, phosphonium, and ether.

paragraph 20. The polymer of paragraph 18 or 19, wherein the monomer is charged.

paragraph 21. The polymer of any of paragraphs 18-20, wherein the monomer is zwitterionic.

paragraph 22. The polymer of any of paragraphs 18-21, wherein the monomer comprises a betaine.

paragraph 23. The polymer of any of paragraphs 18-22, wherein the monomer comprises a phosphorylcholine.

paragraph 24. The polymer of any of paragraphs 18-23, wherein the monomer is hydrophilic.

paragraph 25. The polymer of any of paragraphs 18-24, wherein the monomer is selected from the group consisting of N,N-dimethyl-N-acryloyloxyethyl-N-(3-sulfopropyl)-ammonium betaine, N,N-dimethyl-N-acrylamidopropyl-N-(2-carboxymethyl)-ammonium betaine, N,N-dimethyl-N-acrylamidopropyl-N-(3-sulfopropyl)-ammonium betaine, N,N-dimethyl-N-acrylamidopropyl-N-(2-carboxymethyl)-ammonium betaine, 2-(methylthio)ethyl methacryloyl-S-(sulfopropyl)-sulfonium betaine, 2-[(2-acryloylethyl)dimethylammonio]ethyl 2-methyl phosphate, 2-(acryloyloxyethyl)-2'-(trimethylammonium)ethyl phosphate, [(2-acryloylethyl)dimethylammonio]methyl phosphonic acid, 2-methacryloyloxyethyl phosphorylcholine (MPC), 2-[(3-acrylamidopropyl)dimethylammonio]ethyl 2'-isopropyl phosphate (AAPI), 1-vinyl-3-(3-sulfopropyl)imidazolium hydroxide, (2-acryloxyethyl)carboxymethyl methylsulfonium chloride, 1-(3-sulfopropyl)-2-vinylpyridinium betaine, N-(4-sulfobutyl)-N-methyl-N,N-diallylamine ammonium betaine (MDABS), and N,N-diallyl-N-methyl-N-(2-sulfoethyl)ammonium betaine, and any combination thereof.

paragraph 26. The polymer of any of paragraphs 18-25, further comprising one or more crosslinkers.

paragraph 27. The polymer of paragraph 26, wherein the cross-linker is selected from a compound of Formula XV or XVI, and any combination thereof.

paragraph 28. The polymer of paragraph 27, wherein the cross-linker is ethylene glycol dimethacrylate (EGDMA) or methacryloyloxyethyl-N-(2-methacryloyloxyethyl phosphorylcholine).

paragraph 29. The polymer of any of paragraphs 18-28, wherein the polymer is a gel or hydrogel.

paragraph 30. The polymer of any of paragraphs 18-29, wherein the polymer is in solution.

paragraph 31. The polymer of paragraph 30, wherein the polymer concentration is dilute.

paragraph 32. A method of treating a tissue in a subject, the method comprises (i) administering to the tissue a composition comprising monomers for polymerization in situ;

(ii) allowing the composition to permeate the tissue; and (iii) polymerizing the monomers in situ.

paragraph 33. The method of paragraph 32, wherein the monomers are selected from sugar molecules and polyethylene glycols comprising an ethylenically unsaturated group, compounds of Formula I-XIV, compounds of Formula XVII-XXXVII, or any combinations thereof.

paragraph 34. The method of paragraph 32 or 33, wherein the monomer is selected from the group consisting of N,N-dimethyl-N-acryloyloxyethyl-N-(3-sulfopropyl)-ammonium betaine, N,N-dimethyl-N-acrylamidopropyl-N-(2-carboxymethyl)-ammonium betaine, N,N-dimethyl-N-acrylamidopropyl-N-(3-sulfopropyl)-ammonium betaine, N,N-dimethyl-N-acrylamidopropyl-N-(2-carboxymethyl)-ammonium betaine, 2-(methylthio)ethyl methacryloyl-S-(sulfopropyl)-sulfonium betaine, 2-[(2-acryloylethyl)dimethylammonio]ethyl 2-methyl phosphate, 2-(acryloyloxyethyl)-2'-(trimethylammonium)ethyl phosphate, [(2-acryloylethyl)dimethylammonio]methyl phosphonic acid, 2-methacryloyloxyethyl phosphorylcholine (MPC), 2-[(3-acrylamidopropyl)dimethylammonio]ethyl 2'-isopropyl phosphate (AAPI), 1-vinyl-3-(3-sulfopropyl) imidazolium hydroxide, (2-acryloxyethyl)carboxymethyl methylsulfonium chloride, 1-(3-sulfopropyl)-2-vinylpyridinium betaine, N-(4-sulfobutyl)-N-methyl-N,N-diallylamine ammonium betaine (MDABS), and N,N-diallyl-N-methyl-N-(2-sulfoethyl)ammonium betaine, and any combination thereof, paragraph 35. The method of any of paragraphs 32-34, wherein the monomer comprises a functional group selected from the group consisting of carboxylic acid, carboxylate, sulfate, sulfonate, sulfuric acid, phosphate, phosphonate, phosphoric acid, amine, ammonium, phosphine, phosphonium, and ether.

paragraph 36. The method of any of paragraphs 32-35, wherein the monomer is charged.

paragraph 37. The method of any of paragraphs 32-36, wherein the monomer is zwitterionic.

paragraph 38. The method of any of paragraphs 32-37, wherein the monomer comprises a betaine.

paragraph 39. The method of any of paragraphs 32-38, wherein the monomer comprises a phosphorylcholine.

paragraph 40. The method of any of paragraphs 32-39, wherein the monomer is hydrophilic.

paragraph 41. The method of any of paragraphs 32-40, wherein said permeation is by passive diffusion.

paragraph 42. The method of any of paragraphs 32-41, wherein said permeation is by a physician-controlled diffusion.

paragraph 43. The method of paragraph 42, wherein the physician-controlled diffusion is selected from the group consisting of ultrasound stimulation, application of heat, application of cold, application of relative high pressure, application of relative low pressure, and mechanical tissue convection.

paragraph 44. The method of any of paragraphs 32-43, wherein the composition further comprises one or more cross-linkers.

paragraph 45. The method of paragraph 44, wherein the cross-linker is selected from a compound of Formula XV or XVI, and any combination thereof.

paragraph 46. The polymer of paragraph 45, wherein the cross-linker is ethylene glycol dimethacrylate (EGDMA) or methacryloyloxyethyl-N-(2-methacryloyloxyethyl phosphorylcholine).

paragraph 47. The method of any of paragraphs 32-46, wherein the tissue is diseased, injured, suboptimal, or defective.

paragraph 48. The method of any of paragraphs 32-47, wherein the tissue is elected from group consisting of synovial joint, cartilage, tendon, ligament, vocal cord, urinary system, dermal tissue, epidermal tissue, intervertebral disc, abdominal tissue, ophthalmic tissue, gynecological tissue, epithelial tissue, and any combination thereof.

paragraph 49. The method of paragraph 48, wherein the synovial joint is selected from the group consisting of knee joint, hip joint, elbow joint, ankle joint, and wrist joint.

paragraph 50. The method of any of paragraphs 32-49, wherein the polymer is a viscoelastic agent or an anti-adhesive agent.

paragraph 51. The method of any of paragraphs 32-50, wherein the subject is undergoing soft tissue surgery.

paragraph 52. The method of paragraph 51, wherein said surgery is ophthalmic surgery and the polymer is a viscoelastic agent.

paragraph 53. The method of paragraph 51, wherein said surgery is abdominal or gynecological surgery and the polymer is an anti-adhesive agent.

paragraph 54. The method of any of paragraphs 32-53, wherein the method further comprises administering an effective amount of at least one bioactive agent to the subject.

paragraph 55. The method of paragraph 54, wherein the bioactive agent is selected from the group consisting of small or large organic or inorganic molecules, monosaccharides, disaccharides, trisaccharides, oligosaccharides, polysaccharides, glycosaminoglycans, peptides, proteins, peptide analogs and derivatives thereof, peptidomimetics, polyclonal antibodies and antigen binding fragments thereof, monoclonal antibodies and antigen binding fragments thereof, lipids, nucleic acids, nucleic acid analogs and derivatives, an extract made from biological materials, naturally occurring or synthetic compositions, and any combination thereof.

paragraph 56. The method of paragraph 54 or 55, wherein the bioactive agent is selected from the group consisting of a growth factor, a cytokine, an analgesic, an anesthetic, an antimicrobial agent, an antibacterial agent, an antiviral agent, an antifungal agent, an antibiotic, an anti-inflammatory agent, an antioxidant, an antiseptic agent, and any combination thereof.

paragraph 57. The method of any of paragraphs 54-56, wherein the bioactive agent is selected from the group consisting of collagen, fat, silicone paste, TEFLON paste, calcium hydroxyapatite, hyaluronic acid, hyaluronates, and any combination thereof.

paragraph 58. The method of any of paragraphs 32-57, wherein the polymer is present throughout the tissue's bulk.

paragraph 59. The method of any of paragraphs 32-58, wherein the polymerization is selected from the group consisting of radical polymerization, cationic polymerization, anionic polymerization, reversible addition-fragmentation chain transfer (RAFT) polymerization, atom-transfer radical (ATR) polymerization, and any combinations thereof.

paragraph 60. The method of any of paragraphs 32-59, wherein the polymerization occurs spontaneously after said administration.

paragraph 61. The method of any of paragraphs 32-60, wherein the polymerization is initiated by a light source.

paragraph 62. The method of any of paragraphs 32-61, wherein the polymerization is initiated by a minimally invasive light source.

paragraph 63. The method of paragraph 61 or 62, wherein the light source emits radially.

paragraph 64. The method of any of paragraphs 61-63, wherein the light source is part of device for administering the composition.

paragraph 65. The method of any of paragraphs 61-64, wherein the light source is a laser.

paragraph 66. The method of any of paragraphs 61-65, wherein the polymerization comprises a photo-initiator.
paragraph 67. The method of paragraph 66, wherein the photo-initiator is selected from the group consisting of a peroxide, a ketone, an azo compound, an acylphosphineoxide, a sulfur-containing compound, a quinone, and any combination thereof.
paragraph 68. The method of paragraph 66 or 67, wherein the photo-initiator is selected from the group consisting of eosin, eosin B, eosin Y, an eosin derivative, 1-[4-(2-Hydroxyethoxy)-phenyl]-2-hydroxy-2-methyl-1-propane-1-one, a 1-[4-(2-Hydroxyethoxy)-phenyl]-2-hydroxy-2-methyl-1-propane-1-one derivative, and any combination thereof.
paragraph 69. The method of any of paragraphs 66-68, wherein the polymerization further comprises a co-initiator.
paragraph 70. The method of paragraph 69, wherein the co-initiator is an amine selected from the group consisting of triethanolamine, N-methyl-N,N-diethanolamine, N-ethyl-N,N-diethanolamine, an ester of dimethylaminobenzoic acid.
paragraph 71. The method of any of paragraphs 32-70, wherein the polymerization comprises an accelerant.
paragraph 72. The method of paragraph 71, wherein the accelerant is N-vinyl pyrrolidone.
paragraph 73. The method of any of paragraphs 32-72, further comprising washing the tissue after said polymerization., thereby removing at least a portion of unpolymerized monomers.
paragraph 74. The method of paragraph 73, wherein said washing is by water or saline.
paragraph 75. The method of any of paragraphs 32-74, wherein the polymer increases the compressive strength of the tissue.
paragraph 76. The method of paragraph 75, wherein the increase in compressive strength is an increase in the equilibrium compressive modulus of the tissue, and/or an increase in the peak force modulus of the tissue, and/or an increase in the dynamic modulus of the tissue, and/or an increase in the magnitude of peak force resisted of the tissue.
paragraph 77. The method of any of paragraphs 32-76, wherein the polymer reduces or inhibits exudation of physiological fluid from the tissue while the tissue is under loading.
paragraph 78. The method of any of paragraphs 32-77, wherein the polymer increases affinity of the tissue to imbibe physiological fluid.
paragraph 79. The method of any of paragraphs 32-78, wherein the polymer reduces or inhibits the tissue's tendency to wear, deteriorate, or degenerate under compressive or shear loading paragraph 80. The method of any of paragraphs 32-79, wherein the polymer decreases coefficient of friction of the tissue.
paragraph 81. The method of any of paragraphs 32-80, wherein the polymer increases the lubricity of the tissue.
paragraph 82. The method of any of paragraphs 32-81, wherein the polymer decreases the diffusion or transport of an undesired agent into the treated tissue.
paragraph 83. The method of paragraph 82, wherein the undesired agent is a degradative enzyme selected from the group consisting of a proteolytic enzyme, a saccharolytic enzyme, and a lipolytic enzyme.
paragraph 84. The method of paragraph 82, wherein the undesired agent is an inflammatory agent selected from the group consisting of an interleukin, a leukocyte, an eicosanoid, a cytokine, reactive oxygen species, a granulocyte, and a lymphocyte.
paragraph 85. The method of paragraph 82, wherein the undesired agent is a foreign organism, a non-foreign organism, or a non-organism.
paragraph 86. The method of paragraph 85, wherein the undesired agent is selected from the group consisting of a bacteria, a virus, a fungus, a mutagenic agent, a toxic agent, a cancer cell, and a prion.
paragraph 87. The method of any of paragraphs 32-86, wherein the in situ polymerization produces an interpenetrating network located near, adjacent to, or surrounding a material of increased stiffness, toughness, or hardness.
paragraph 88. The method of paragraph 87, wherein the material of increased stiffness, toughness, or hardness is a tissue of the subject, selected from the group consisting of bone, cartilage, ligament, and tendon.
paragraph 89. The method of paragraph 87, wherein the material of increased stiffness, toughness, or hardness is an implanted device.
paragraph 90. The method of paragraph 89, wherein the implanted device is comprised of a material selected from the group consisting of a metal, a metallic alloy, a plastic material, a polymer, a ceramic material, and any combination thereof.
paragraph 91. The method of paragraph 89 or 90, wherein the implanted device is selected from the group consisting of a micro-electromechanical system (MEMS), a circuit board, a computer chip, a sensor, and a medical device.
paragraph 92. The method of any of paragraphs 87-91, wherein the method is used to lessen the abruptness of disparity in mechanical properties between a soft tissue penetrated by the monomers and the material of increased stiffness, toughness, or hardness.
paragraph 93. The method of any of paragraphs 32-92, wherein the polymer exhibits a long residence time in the tissue. As used herein, the term "long residence time" refers to a half-life of 30 days or more. Stated another way, 50% or more by mass of the polymer remain in the region of interest after 30 days.
paragraph 94. The method of paragraph 93, wherein the long residence time results from a lack of polymer degradability or low or minimal polymer degradability. As used herein, the term "low degrability" refers to a degradation rate of less than or equal to 2% of the bonds in the polymer backbone being degraded per day. As used herein, the term "polymer backbone" refers to the covalently bonded chain of repeating monomer units along the direction of polymerization that form the polymer. In some embodiments, the polymer backbone can also include the bonds in the cross-linkers.
paragraph 95. The method of any of paragraphs 32-92, wherein the polymer exhibits a short or moderate residence time in the tissue. As used herein, the term "short residence time" means a half-life less than 5 days. As used herein, the term "moderate residence time" means a half-life 5 days or more but fewer than 30 days.
paragraph 96. The method of paragraph 95, wherein the residence time is a function of polymer degradability or biodegradability.
paragraph 97. The method of paragraph 95 or 96, wherein the degradability or biodegradability occurs via one or more natural breakdown processes selected from the group consisting of hydrolysis, enzyme-mediate cleavage of an ester bond, enzyme-mediate cleavage of an amide bond, and enzyme-mediate cleavage of a glycosidic bond.
paragraph 98. The method of paragraph 95 or 96, wherein the degradability or biodegradability occurs via one or more non-natural breakdown processes initiable by an external stimulus selected from the group consisting of light, heat, acoustic energy, a chemical agent, and a biological agent.

paragraph 99. The method of paragraph 98, wherein the external stimulus can cleave a covalent bond or disrupt a non-covalent network.

paragraph 100. The method of any of paragraphs 32-99, wherein the subject is a mammal.

paragraph 101. The method of paragraph 100, wherein the subject is human.

paragraph 102. The method of any of paragraphs 32-100, wherein the subject is a non-human animal.

paragraph 103. The method of any of paragraphs 32-102, wherein the composition further comprises a pharmaceutically acceptable excipient or carrier.

paragraph 104. A method of treating a tissue in a subject, the method comprising administering to the subject a composition comprising the polymer of any of paragraphs 18-31.

paragraph 105. The method of paragraph 104, wherein the tissue is diseased, injured, suboptimal, or defective.

paragraph 106. The method of paragraph 104 or 105, wherein the tissue is selected from group consisting of synovial joint, cartilage, tendon, ligament, vocal cord, urinary system, dermal tissue, epidermal tissue, intervertebral disc, abdominal tissue, ophthalmic tissue, gynecological tissue, epithelial tissue, and any combination thereof.

paragraph 107. The method of paragraph 106, wherein the synovial joint is selected from the group consisting of knee joint, hip joint, elbow joint, ankle joint, and wrist joint.

paragraph 108. The method of any of paragraphs 104-107, further comprising administering an effective amount of at least one bioactive agent to the subject.

paragraph 109. The method of paragraph 108, wherein the bioactive agent is selected from the group consisting of small or large organic or inorganic molecules, monosaccharides, disaccharides, trisaccharides, oligosaccharides, polysaccharides, glycosaminoglycans, peptides, proteins, peptide analogs and derivatives thereof, peptidomimetics, polyclonal antibodies and antigen binding fragments thereof, monoclonal antibodies and antigen binding fragments thereof, lipids, nucleic acids, nucleic acid analogs and derivatives, an extract made from biological materials, naturally occurring or synthetic compositions, and any combination thereof.

paragraph 110. The method of paragraph 108 or 109, wherein the bioactive agent is selected from the group consisting of a growth factor, a cytokine, an analgesic, an anesthetic, an antimicrobial agent, an antibacterial agent, an antiviral agent, an antifungal agent, an antibiotic, an anti-inflammatory agent, an antioxidant, an antiseptic agent, and any combination thereof.

paragraph 111. The method of any of paragraphs 108-110, wherein the bioactive agent is selected from the group consisting of collagen, fat, silicone paste, TEFLON paste, calcium hydroxyapatite, hyaluronic acid, hyaluronates, and any combination thereof.

paragraph 112. The method of any of paragraphs 104-111, wherein said administering is by injection.

paragraph 113. The method of any of paragraphs 104-112, wherein the polymer is administered at least once.

paragraph 114. The method of any of paragraphs 104-113, wherein the polymer is administered at least twice.

paragraph 115. The method of paragraph 114, wherein the polymer is administered at least twice and wherein said administrations are at least six months apart.

paragraph 116. The method of any of paragraphs 104-115, wherein the polymer increases the compressive strength of the tissue.

paragraph 117. The method of paragraph 116, wherein the increase in compressive strength is an increase in the equilibrium compressive modulus of the tissue, and/or an increase in the peak force modulus of the tissue, and/or an increase in the dynamic modulus of the tissue, and/or an increase in the magnitude of peak force resisted of the tissue.

paragraph 118. The method of any of paragraphs 104-117, wherein the polymer reduces or inhibits exudation of physiological fluid from the tissue while the tissue is under loading.

paragraph 119. The method of any of paragraphs 104-118, wherein the polymer increases affinity of the tissue to imbibe physiological fluid.

paragraph 120. The method of any of paragraphs 104-119, wherein the polymer reduces or inhibits the tissue's tendency to wear, deteriorate, or degenerate under compressive or shear loading paragraph 121. The method of any of paragraphs 104-120, wherein the polymer decreases coefficient of friction of the tissue.

paragraph 122. The method of any of paragraphs 104-121, wherein the polymer increases lubricity of the tissue.

paragraph 123. The method of any of paragraphs 104-122, wherein the polymer exhibits a long residence time in the tissue.

paragraph 124. The method of paragraph 123, wherein the long residence time results from a lack of polymer degradability or low or minimal polymer degradability.

paragraph 125. The method of any of paragraphs 104-122, wherein the polymer exhibits a short or moderate residence time in the tissue.

paragraph 126. The method of paragraph 125, wherein the residence time is a function of polymer degradability or biodegradability.

paragraph 127. The method of paragraph 125 or 126, wherein the degradability or biodegradability occurs via one or more natural breakdown processes selected from the group consisting of hydrolysis, enzyme-mediate cleavage of an ester bond, enzyme-mediate cleavage of an amide bond, and enzyme-mediate cleavage of a glycosidic bond.

paragraph 128. The method of paragraph 125 or 126, wherein the degradability or biodegradability occurs via one or more non-natural breakdown processes initiable by an external stimulus selected from the group consisting of light, heat, acoustic energy, a chemical agent, and a biological agent.

paragraph 129. The method of paragraph 128, wherein the external stimulus can cleave a covalent bond or disrupt a non-covalent network.

paragraph 130. The method of any of paragraphs 104-129, wherein the subject is a mammal.

paragraph 131. The method of paragraph 130, wherein the subject is human.

paragraph 132. The method of any of paragraphs 104-130, wherein the subject is a non-human animal.

paragraph 133. The method of any of paragraphs 104-132, wherein polymer is in a pharmaceutical composition comprising the polymer and a pharmaceutically acceptable excipient or carrier.

paragraph 134. A method of synthesizing a polymer in a tissue, comprising (i) administering to the tissue a composition comprising monomers for polymerization in situ;
(ii) allowing the composition to permeate the tissue; and
(iii) polymerizing the monomers in situ.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular. Thus, as used herein and in the claims, the singular forms include the plural reference and vice versa unless the context clearly indicates otherwise.

As used herein the term "comprising" or "comprises" is used in reference to compositions, methods, and respective component(s) thereof, that are useful to an embodiment, yet open to the inclusion of unspecified elements, whether useful or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages can mean 5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

As used herein, the term "biodegradable" describes a material which can decompose partially or fully under physiological conditions into breakdown products. The material under physiological conditions can undergo reactions or interactions such as hydrolysis (decomposition via hydrolytic cleavage), enzymatic catalysis (enzymatic degradation), and mechanical interactions. As used herein, the term "biodegradable" also encompasses the term "bioresorbable", which describes a substance that decomposes under physiological conditions to break down to products that undergo bioresorption into the host-organism, namely, become metabolites of the biochemical systems of the host organism. For example, a material is biodegradable if at least 10%, at least 20%, at least 30%, at least 40%, or more preferably, at least 50%, at least 60%, at least 70%, at least 80%, at least 90% of the material can decompose under physiological conditions within a desired period of time, such as on the order of minutes, hours, days, weeks, or months, depending on the exact material.

As used herein, the term "physiological conditions" refer to conditions of temperature, pH, osmotic pressure, osmolality, oxidation and electrolyte concentration in vivo in a patient or subject at the site of administration, or the site of action. For example, physiological conditions generally mean pH at about 6 to 8 and temperature of about 37° C. in the presence of serum or other body fluids.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviations (2SD) away from a reference level. The term refers to statistical evidence that there is a difference. It is defined as the probability of making a decision to reject the null hypothesis when the null hypothesis is actually true.

As used interchangeably herein, the terms "essentially" and "substantially" means a proportion of at least about 60%, or preferably at least about 70% or at least about 80%, or at least about 90%, at least about 95%, at least about 97% or at least about 99% or more, or any integer between 70% and 100%. In some embodiments, the term "essentially" means a proportion of at least about 90%, at least about 95%, at least about 98%, at least about 99% or more, or any integer between 90% and 100%. In some embodiments, the term "essentially" can include 100%.

The term "MPC" means 2-methacryloyloxyethyl phosphorylcholine. The term "pMPC" means poly(2-methacryloyloxyethyl phosphorylcholine).]

The term "PEG" means poly(ethylene glycol).

The term "PEGMA" means poly(ethylene glycol) methacrylate.

The term "pPEGMA" means poly(poly(ethylene glycol) methacrylate).

The term "PEGDA" means poly(ethylene glycol) diacrylate.

The term "pPEGDA" means poly(poly(ethylene glycol) diacrylate).

The term "BSF" means bovine synovial fluid.

The term "MRI" means magnetic resonance imaging.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, rabbits, deer, bison, buffalo, goats, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "individual", "patient", "subject", and the like are used interchangeably herein. The terms do not denote a particular age, and thus encompass adults, children, and newborn. A subject can be a male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with autoimmune disease or inflammation. In addition, the methods and compositions described herein can be used for domesticated animals and/or pets. A human subject can be of any age, gender, race or ethnic group, e.g., Caucasian (white), Asian, African, black, African American, African European, Hispanic, Mideastern, etc. . . . In some embodiments, the subject can be a patient or other subject in a clinical setting. In some embodiments, the subject can already be undergoing treatment.

As used herein, the terms "treat," "treatment," "treating," or "amelioration" are used herein to characterize a method or process that is aimed at (1) delaying or preventing the onset of a disease or condition; (2) slowing down or stopping the progression, aggravation, or deterioration of the symptoms of the disease or condition; (3) bringing about ameliorations of the symptoms of the disease or condition; or (4) curing the disease or condition. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased morbidity or mortality. The term "treatment" of a disease also includes providing relief from the symptoms or side-effects of the disease (including palliative treatment). A treatment can be administered prior to the onset of the disease, for a prophylactic or preventive action. Alternatively or additionally, the treatment can be administered after initiation of the disease or condition, for a therapeutic action.

The term "local", when used herein to characterize the delivery, administration or application of a polymer of the present invention, or a pharmaceutical composition thereof, is meant to specify that the polymer or composition, is delivered, administered or applied directly to the site to be treated or in the vicinity of the site to be treated for a localized effect. For example, an inventive polysaccharide mimic used as a viscosupplement will generally be injected directly to an osteoarthritic knee joint; an inventive polysaccharide mimic used as tissue space filler will generally be injected directly to a diseased or damaged vocal cord, or to a skin area displaying lines or wrinkles. Preferably, local administration is effected without any significant absorption of components of the polysaccharide mimic into the patient's blood stream (to avoid a systemic effect).

As used herein, the term "effective amount" refers to any amount of a molecule, compound or composition that is sufficient to fulfill its intended purpose(s), i.e., to elicit a desired biological or medicinal response in a tissue or subject. Examples of intended purposes of an inventive polymer include, but are not limited to, to provide viscosupplementation to a joint, to allow soft tissue augmentation, to prevent or reduce adhesion formation, to facilitate tissue manipulation, and/or to maintain, support or protect soft tissue.

As used herein, the term "soft tissue" includes all tissue of the body except bone. Examples of soft tissue include, but are not limited to, muscles, tendons, fibrous tissues, fat, blood vessels, nerves, and synovial tissues.

As used herein, the term "wound" is used to describe skin wounds as well as tissue wounds. A skin wound is defined herein as a break in the continuity of skin tissue that is caused by direct injury to the skin. Several classes including punctures, incisions, excisions, lacerations, abrasions, atrophic skin, or necrotic wounds and burns generally characterize skin wounds. The compositions and methods of the invention are useful for enhancing the healing of all wounds of the skin.

A "tissue wound" as used herein is a wound to an internal organ, such as a blood vessel, intestine, colon, etc. The materials of the invention are useful for enhancing the wound healing process in tissue wounds whether they arise naturally or as the result of surgery. For instance, during the repair of arteries the vessel needs to be sealed and wound healing must be promoted as quickly as possible. The compositions of the invention can speed up that process. The compositions of the invention are also particularly useful for the treatment of damaged tissue.

The terms "bioactive agent" and "biologically active agent" are used herein interchangeably. They refer to compounds or entities that alter, inhibit, activate or otherwise affect biological or chemical events.

Without limitations, a bioactive agent can be selected from small organic or inorganic molecules; saccharines; oligosaccharides; polysaccharides; biological macromolecules, e.g., peptides, proteins, and peptide analogs and derivatives, polyclonal antibodies and antigen binding fragments thereof, monoclonal antibodies and antigen binding fragments thereof; peptidomimetics; nucleic acids and nucleic acid analogs and derivatives (including but not limited to siRNAs, shRNAs, antisense oligonucleotides, ribozymes, and aptamers); an extract made from biological materials such as bacteria, plants, fungi, or animal cells; animal tissues; naturally occurring or synthetic compositions; and any combinations thereof.

Exemplary bioactive agents include, but are not limited to, vitamins, anti-cancer substances, antibiotics, immunosuppressants, anti-viral substances, enzyme inhibitors, opioids, hypnotics, lubricants, tranquilizers, anti-convulsants, muscle relaxants, anti-spasmodics and muscle contractants, anti-glaucoma compounds, modulators of cell-extracellular matrix interactions including cell growth inhibitors and anti-adhesion molecules, vasodilating agents, analgesics, anti-pyretics, steroidal and non-steroidal anti-inflammatory agents, anti-angiogenic factors, anti-secretory factors, anti-coagulants and/or antithrombotic agents, local anesthetics, ophthalmics, prostaglandins, anti-depressants, anti-psychotic substances, anti-emetics, imaging agents. A more complete, although not exhaustive, listing of classes and specific drugs suitable for use in the present invention can be found in "Pharmaceutical Substances: Synthesis, Patents, Applications" by A. Kleeman and J. Engel, Thieme Medical Publishing, 1999; Harrison's Principles of Internal Medicine, 13th Edition, Eds. T. R. Harrison et al. McGraw-Hill N.Y., NY; Physicians' Desk Reference, 50th Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's The Pharmacological Basis of Therapeutics; and the current edition of "Merck Index: An Encyclopedia of Chemicals, Drugs, and Biologicals", S. Budavari et al. (Eds), CRC Press, contents of all of which are incorporated herein by reference in their entireties.

The term "small molecule" refers to molecules, whether naturally-occurring or artificially created (e.g., via chemical synthesis) that have a relatively low molecular weight, e.g., less than 1 kDa. Preferred small molecules are biologically active in that they produce a local or systemic effect in animals, preferably mammals, more preferably humans. Typically, small molecules have a molecular weight of less than about 1,500 Da. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§ 330.5, 331 through 361, and 440 through 460; drugs for veterinary use listed by the FDA under 21 C.F.R. §§ 500 through 589, incorporated herein by reference, are all considered suitable for use with the present polysaccharide mimic polymers.

The terms "polysaccharide", "carbohydrate", and "oligosaccharide" are used herein interchangeably. They refer to a compound that comprises at least two sugar units, or derivatives thereof. Polysaccharides may be purified from natural sources such as plants or may be synthesized de novo in the laboratory. Polysaccharides isolated from natural sources may be modified chemically to change their chemical or physical properties (e.g., reduced, oxidized, phosphorylated, cross-linked). Carbohydrate polymers or oligomers may include natural sugars (e.g., glucose, fructose, galactose, mannose, arabinose, ribose, xylose, etc.) and/or modified sugars (e.g., 2'-fluororibose, 2'-deoxyribose, etc.). Polysaccharides may also be either straight or branched. They may contain both natural and/or unnatural carbohydrate residues. The linkage between the residues may be the typical ether linkage found in nature or may be a linkage only available to synthetic chemists. Examples of polysaccharides include cellulose, maltin, maltose, starch, modified starch, dextran, poly(dextrose), and fructose. Glycosaminoglycans are also considered polysaccharides. Sugar alcohol, as used herein, refers to any polyol such as sorbitol, mannitol, xylitol, galactitol, erythritol, inositol, ribitol, dulcitol, adonitol, arabitol, dithioerythritol, dithiothreitol, glycerol, isomalt, and hydrogenated starch hydrolysates.

An entity is herein said to be "associated with" another entity if they are linked by a direct or indirect, covalent or non-covalent interaction. In certain embodiments, the association is covalent. Exemplary non-covalent interactions include hydrogen bonding, van der Walls interactions, hydrophobic interactions, magnetic interactions, electrostatic interactions, or combinations thereof.

As used herein, the term "permeate" refers to the dispersion, infiltration, and/or diffusion of a composition, e.g., a composition comprising the monomers described herein, in a target tissue such as a degenerative or defective tissue. In some embodiments, the composition permeates at least 30%, at least 40%, at least 50%, at least 60%, at least 70%, at least 80%, or at least 90% of the target tissue.

In general, the term "aliphatic", as used herein, includes both saturated and unsaturated, straight chain (i.e., unbranched) or branched aliphatic hydrocarbons, which are optionally substituted with one or more functional groups, as defined below. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having 1-6 carbon atoms. In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms.

Illustrative aliphatic groups thus include, but are not limited to, for example, methyl, ethyl, n-propyl, isopropyl, allyl, n-butyl, sec-butyl, isobutyl, tert-butyl, n-pentyl; sec-pentyl, isopentyl, tert-pentyl, n-hexyl, sec-hexyl, moieties and the like, which again, may bear one or more substituents, as previously defined. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups, as defined below. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —$CH_2$-cyclopropyl, cyclobutyl, —$CH_2$-cyclobutyl, cyclopentyl, —$CH_2$-cyclopentyl-n, cyclohexyl, —$CH_2$-cyclohexyl, cyclohexenylethyl, cyclohexanylethyl, norborbyl moieties and the like, which again, may bear one or more substituents.

The term "heteroaliphatic", as used herein, refers to aliphatic moieties in which one or more carbon atoms in the main chain have been substituted with an heteroatom. Thus, a heteroaliphatic group refers to an aliphatic chain which contains one or more oxygen sulfur, nitrogen, phosphorus or silicon atoms, e.g., in place of carbon atoms. Heteroaliphatic moieties may be saturated or unsaturated, branched or linear (i.e., unbranched), and substituted or unsubstituted. Substituents include, but are not limited to, any of the substituents mentioned below, i.e., the substituents recited below resulting in the formation of a stable compound.

The term "heteroalicyclic", as used herein, refers to compounds which combine the properties of heteroaliphatic and the cyclic compounds and include but are not limited to saturated and unsaturated mono- or polycyclic heterocycles such as morpholino, pyrrolidinyl, furanyl, thiofuranyl, pyrrolyl, etc, which are optionally substituted with one or more functional groups. Substituents include, but are not limited to, any of the substituents mentioned below, i.e., the substituents recited below resulting in the formation of a stable compound.

The term "alkyl", as used herein, refers to saturated, straight- or branched-chain hydrocarbon radicals derived from a hydrocarbon moiety containing between one and twenty carbon atoms by removal of a single hydrogen atom, which alkyl groups are optionally substituted with one or more functional groups. Substituents include, but are not limited to, any of the substituents mentioned below, i.e., the substituents recited below resulting in the formation of a stable compound. Examples of alkyl radicals include, but are not limited to, methyl, ethyl, propyl, isopropyl, n-butyl, tert-butyl, n-pentyl, neopentyl, n-hexyl, n-heptyl, n-octyl, n-decyl, n-undecyl, and dodecyl.

The term "alkoxy", as used herein, refers to an alkyl group, as previously defined, attached to the parent molecular moiety through an oxygen atom. Examples include, but are not limited to, methoxy, ethoxy, propoxy, isopropoxy, n-butoxy, tert-butoxy, neopentoxy, and n-hexoxy.

The term "alkenyl" denotes a monovalent group derived from a hydrocarbon moiety having at least one carbon-carbon double bond, which alkenyl group is optionally substituted with one or more functional groups. In certain embodiments, an alkenyl group contains between one and twenty carbon atoms. Substituents include, but are not limited to, any of the substituents mentioned below, i.e., the substituents recited below resulting in the formation of a stable compound. Alkenyl groups include, for example, ethenyl, propenyl, butenyl, 1-methyl-2-buten-1-yl, and the like. The term "alkynyl", as used herein, refers to a monovalent group derived from a hydrocarbon having at least one carbon-carbon triple bond, which alkynyl group is optionally substituted. In certain embodiments, an alkynyl group contains between one and twenty carbon atoms. Substituents include, but are not limited to, any of the substituents mentioned below, i.e., the substituents recited below resulting in the formation of a stable compound. Representative alkynyl groups include ethynyl, 2-propynyl (propargyl), 1-propynyl, and the like. The term "amine", as used herein, refers to one, two, or three alkyl groups, as previously defined, attached to the parent molecular moiety through a nitrogen atom. The term "alkylamino" refers to a group having the structure —NHR' wherein R' is an alkyl group, as previously defined; and the term "dialkylamino" refers to a group having the structure —NR'R", wherein R' and R" are each independently selected from the group consisting of alkyl groups. The term "trialkylamino" refers to a group having the structure —NR'R"R'", wherein R', R", and R'" are each independently selected from the group consisting of alkyl groups. Additionally, R', R", and/or R'" taken together may optionally be —$CH_2$).sub.k—where k is an integer from 2 to 6. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "aryl", as used herein, refers to stable mono- or polycyclic, unsaturated moieties having preferably 3-14 carbon atoms, each of which may be substituted or unsubstituted. Substituents include, but are not limited to, any of the substituents mentioned below, i.e., the substituents recited below resulting in the formation of a stable compound. The term aryl may refer to a mono- or bicyclic carbocyclic ring system having one or two aromatic rings including, but not limited to, phenyl, naphthyl, tetrahydronaphthyl, indanyl, indenyl and the like.

The term "heteroaryl", as used herein refers to a stable heterocyclic or polyheterocyclic, unsaturated radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms. Heteroaryl moieties may be substituted or unsubstituted. Substituents include, but are not limited to, any of the substituents mentioned below, i.e., the substituents recited below resulting in the formation of a stable compound. Examples of heteroaryl nuclei include pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will also be appreciated that aryl and heteroaryl moieties, as defined herein, may be attached via an aliphatic, alicyclic, heteroaliphatic, heteroalicyclic, alkyl or heteroalkyl moiety and thus also include -aliphatic)aryl, -(heteroaliphatic)aryl, -(aliphatic)heteroaryl, -(heteroaliphatic) heteroaryl, -alkyl)aryl, -(heteroalkyl)aryl, -(heteroalkyl)aryl, and -heteroalkyl)-heteroaryl moieties. Thus, as used herein, the phrases "aryl or heteroaryl" and "aryl, heteroaryl, -(aliphatic)aryl, -(heteroaliphatic)aryl, -(aliphatic)heteroaryl, -(heteroaliphatic)heteroaryl, -(alkyl)aryl, -(heteroalkyl)aryl, -(heteroalkyl)aryl, and -(heteroalkyl)heteroaryl" are interchangeable.

The term "carboxylic acid", as used herein, refers to a group of formula —$CO_2H$.

The terms "halo", "halide", and "halogen", as used herein, refers to an atom selected from fluorine, chlorine, bromine, and iodine.

The term "methylol", as used herein, refers to an alcohol group of structure —$CH_2OH$.

The term "hydroxyalkyl" refers to an alkyl group, as defined above, bearing at least one OH group.

The term "mercaptoalkyl", a used herein, refers to an alkyl group, as defined above, bearing at least one SH group.

The term "heterocyclic", as used herein, refers to a non-aromatic partially unsaturated or fully saturated 3- to 10-membered ring system, which includes single rings of 3 to 8 atoms in size and bi- and tri-cyclic ring systems which may include aromatic six-membered aryl or aromatic heterocyclic groups fused to a non-aromatic ring. Heterocyclic moieties may be substituted or unsubstituted. Substituents include, but are not limited to, any of the substituents mentioned below, i.e., the substituents recited below resulting in the formation of a stable compound. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized.

The term "acyl", as used herein, refers to a group comprising a carbonyl group of the formula C=O. Examples of acyl groups include aldehydes, ketones, carboxylic acids, acyl halides, anhydrides, thioesters, amides, urea, carbamate, and carboxylic esters.

The term "hydrocarbon", as used herein, refers to any chemical group comprising hydrogen and carbon. The hydrocarbon may be substituted or unsubstituted. The hydrocarbon may be unsaturated, saturated, branched, unbranched, cyclic, polycyclic, or heterocyclic. Illustrative hydrocarbons include, for example, methyl, ethyl, n-propyl, iso-propyl, cyclopropyl, allyl, vinyl, n-butyl, tert-butyl, ethynyl, cyclohexyl, methoxy, diethylamino, and the like. As would be known to one skilled in this art, all valencies must be satisfied in making any substitutions. Likewise, the term "fluorocarbon", as used herein, refers to any chemical group comprising more fluorine atoms than hydrogen atoms attached to carbons. The fluorocarbon may be substituted or unsubstituted. A fluorocarbon may be saturated, unsaturated, branched, unbranched, cyclic, polycyclic or heterocyclic.

The term "substituted", whether preceded by the term "optionally" or not, refers to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Heteroatoms such as nitrogen may have hydrogen substituents and/or any permissible substituents of organic compounds described herein which satisfy the valencies of the heteroatoms. Examples of substituents include, but are not limited to aliphatic; alicyclic; heteroaliphatic; heteroalicyclic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —NCO; —CF$_3$; —CH$_2$CF$_3$; —CHCl$_2$; —CH$_2$OR$_x$; —CH$_2$CH$_2$OR.sub.x; —CH$_2$N(R$_x$)$_2$; —CH$_2$SO$_2$CH$_3$; —C(O)R$_x$; —CO$_2$(R$_x$); —CON(R$_x$)$_2$; —OC(O)R$_x$; —C(O)OC(O)R$_x$; —OCO$_2$R$_x$; —OCON(R$_x$)$_2$; —N(R$_x$)$_2$; —S(O)$_2$R$_x$; —OCO$_2$R$_x$; —NR$_x$(CO)R$_x$; —NR$_x$(CO)N(R$_x$)$_2$, wherein each occurrence of R.sub.x independently includes, but is not limited to, H, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted.

As used herein, the terms "proteins" and "peptides" are used interchangeably herein to designate a series of amino acid residues connected to the other by peptide bonds between the alpha-amino and carboxy groups of adjacent residues. The terms "protein", and "peptide", which are used interchangeably herein, refer to a polymer of protein amino acids, including modified amino acids (e.g., phosphorylated, glycated, etc.) and amino acid analogs, regardless of its size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins and fragments of proteins, unless otherwise noted. The terms "protein" and "peptide" are used interchangeably herein when referring to a gene product and fragments thereof. Thus, exemplary peptides or proteins include gene products, naturally occurring proteins, homologs, orthologs, paralogs, fragments and other equivalents, variants, fragments, and analogs of the foregoing.

As used herein, the term "nucleic acid" or "oligonucleotide" or grammatical equivalents herein means at least two nucleotides, including analogs or derivatives thereof, that are covalently linked together. Exemplary oligonucleotides include, but are not limited to, single-stranded and double-stranded siRNAs and other RNA interference reagents (RNAi agents or iRNA agents), shRNA (short hairpin RNAs), antisense oligonucleotides, aptamers, ribozymes, and microRNAs (miRNAs). The nucleic acids can be single stranded or double stranded. The nucleic acid can be DNA, RNA or a hybrid, where the nucleic acid contains any combination of deoxyribo- and ribo-nucleotides, and any combination of uracil, adenine, thymine, cytosine and guanine. The nucleic acids can comprise one or more backbone modifications, e.g., phosphoramide (Beaucage et al., Tetrahedron 49(10):1925 (1993) and references therein; Letsinger, J. Org. Chem. 35:3800 (1970)), phosphorothioate, phosphorodithioate, O-methylphophoroamidite linkages (see Eckstein, Oligonucleotides and Analogues: A Practical Approach, Oxford University Press), or peptide nucleic acid linkages (see Egholm, J. Am. Chem. Soc. 114:1895 (1992); Meier et al., Chem. Int. Ed. Engl. 31:1008 (1992); and Nielsen, Nature, 365:566 (1993), content of all of which is herein incorporated by reference. The nucleic acids can also include modifications to nucleobase and/or sugar moietites of nucleotides. Examplary sugar modifications at the sugar moiety include replacement of 2'-OH with halogens (e.g., fluoro), O-mehtyl, O-methoxyethyl, NH$_2$, SH and S-methyl.

The term "short interfering RNA" (siRNA), also referred to herein as "small interfering RNA" is defined as an agent which functions to inhibit expression of a target gene, e.g., by RNAi. An siRNA can be chemically synthesized, it can be produced by in vitro transcription, or it can be produced within a host cell. siRNA molecules can also be generated by cleavage of double stranded RNA, where one strand is identical to the message to be inactivated. The term "siRNA" refers to small inhibitory RNA duplexes that induce the RNA interference (RNAi) pathway. These molecules can vary in length (generally 18-30 base pairs) and contain varying degrees of complementarity to their target mRNA in the antisense strand. Some, but not all, siRNA have unpaired overhanging bases on the 5' or 3' end of the sense 60 strand and/or the antisense strand. The term "siRNA" includes duplexes of two separate strands, as well as single strands that can form hairpin structures comprising a duplex region.

The term "shRNA" as used herein refers to short hairpin RNA which functions as RNAi and/or siRNA species but differs in that shRNA species are double stranded hairpin-like structure for increased stability. The term "RNAi" as used herein refers to interfering RNA, or RNA interference molecules are nucleic acid molecules or analogues thereof for example RNA-based molecules that inhibit gene expression. RNAi refers to a means of selective post-transcriptional gene silencing. RNAi can result in the destruction of specific mRNA, or prevents the processing or translation of RNA, such as mRNA.

As used herein, the term "antibody" or "antibodies" refers to an intact immunoglobulin or to a monoclonal or polyclonal antigen-binding fragment with the Fc (crystallizable fragment) region or FcRn binding fragment of the Fc region. The term "antibodies" also includes "antibody-like molecules", such as fragments of the antibodies, e.g., antigen-binding fragments. Antigen-binding fragments can be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies, and polypeptides that contain at least a portion of an immunoglobulin that is sufficient to confer specific antigen binding to the polypeptide. Linear antibodies are also included for the purposes described herein. The terms Fab, Fc, pFc', F(ab') 2 and Fv are employed with standard immunological meanings (Klein, Immunology (John Wiley, New York, N.Y., 1982); Clark, W. R. (1986) The Experimental Foundations of Modern Immunology (Wiley & Sons, Inc., New York); and Roitt, I. (1991) Essential Immunology, 7th Ed., (Blackwell Scientific Publications, Oxford)). Antibodies or antigen-binding fragments specific for various antigens are available commercially from vendors such as R&D Systems, BD Biosciences, e-Biosciences and Miltenyi, or can be raised against these cell-surface markers by methods known to those skilled in the art.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1. Synthesis of Cartilage-Hydrogel Inter-Penetrating Network (IPN) Containing Polymerized MPC (pMPC) in an Explant Bovine osteochondral explants were incubated for 24 hours in the dark in an aqueous solution containing 2-methacryloyloxyethyl phosphorylcholine (MPC) (20 w/v %), ethylene glycol dimethacrylate (1 mol % of MPC), eosin y (0.1 mM), triethanolamine (115 mM), and N-vinyl pyrrolidone (75 mM). The explants were removed from solution, irradiated with a 514 nm argon ion laser (500 mW/cm$^2$, 7.5 min), and rinsed for 2 days in saline to wash out residual non-reacted monomer.

Figure 3A:
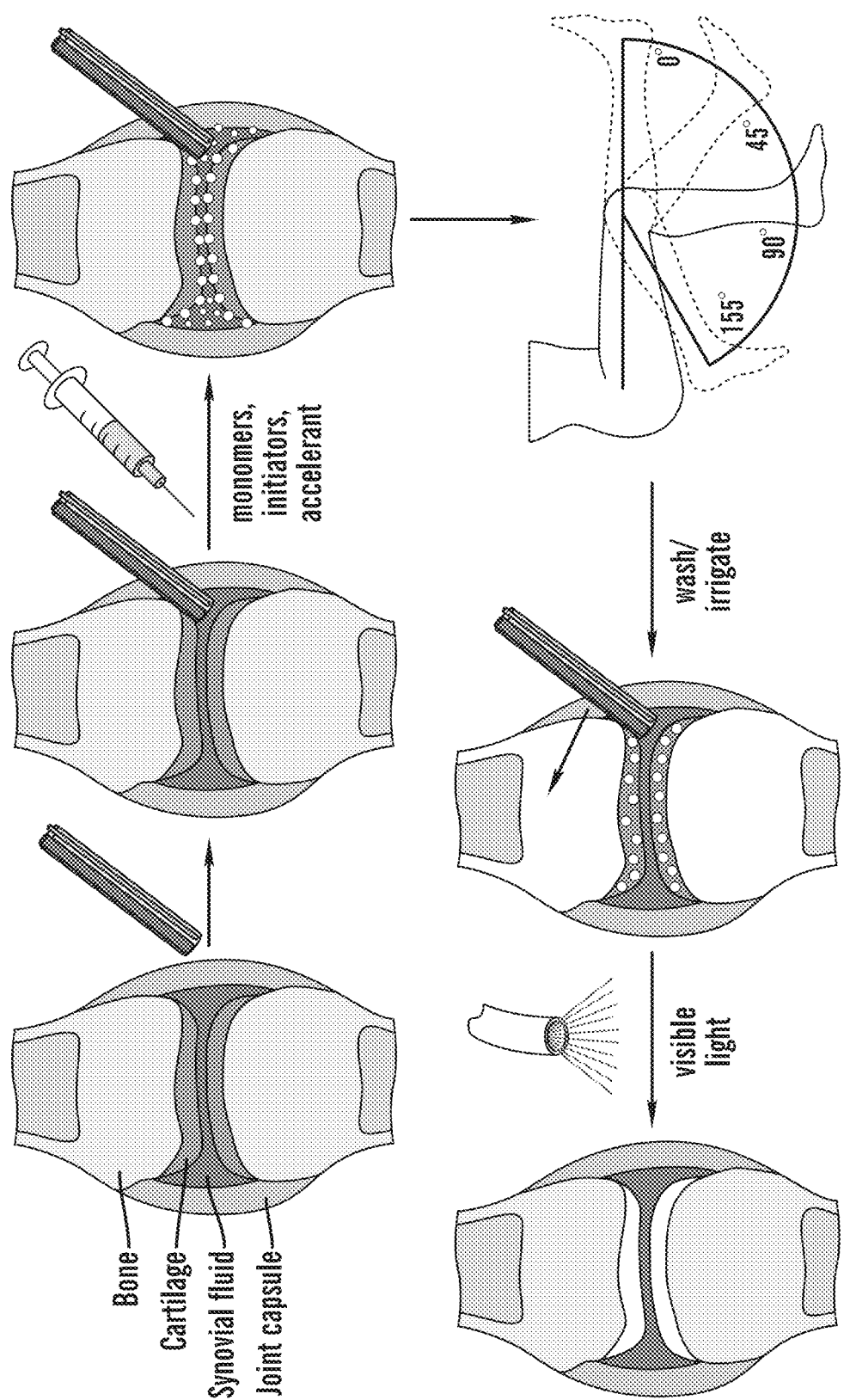
FIG. 3A is a schematic showing a procedure for the synthesis of cartilage-hydrogel IPN containing polymerized 2-methacryloyloxyethyl phosphorylcholine (pMPC) in a whole knee joint.
Figure 3B:
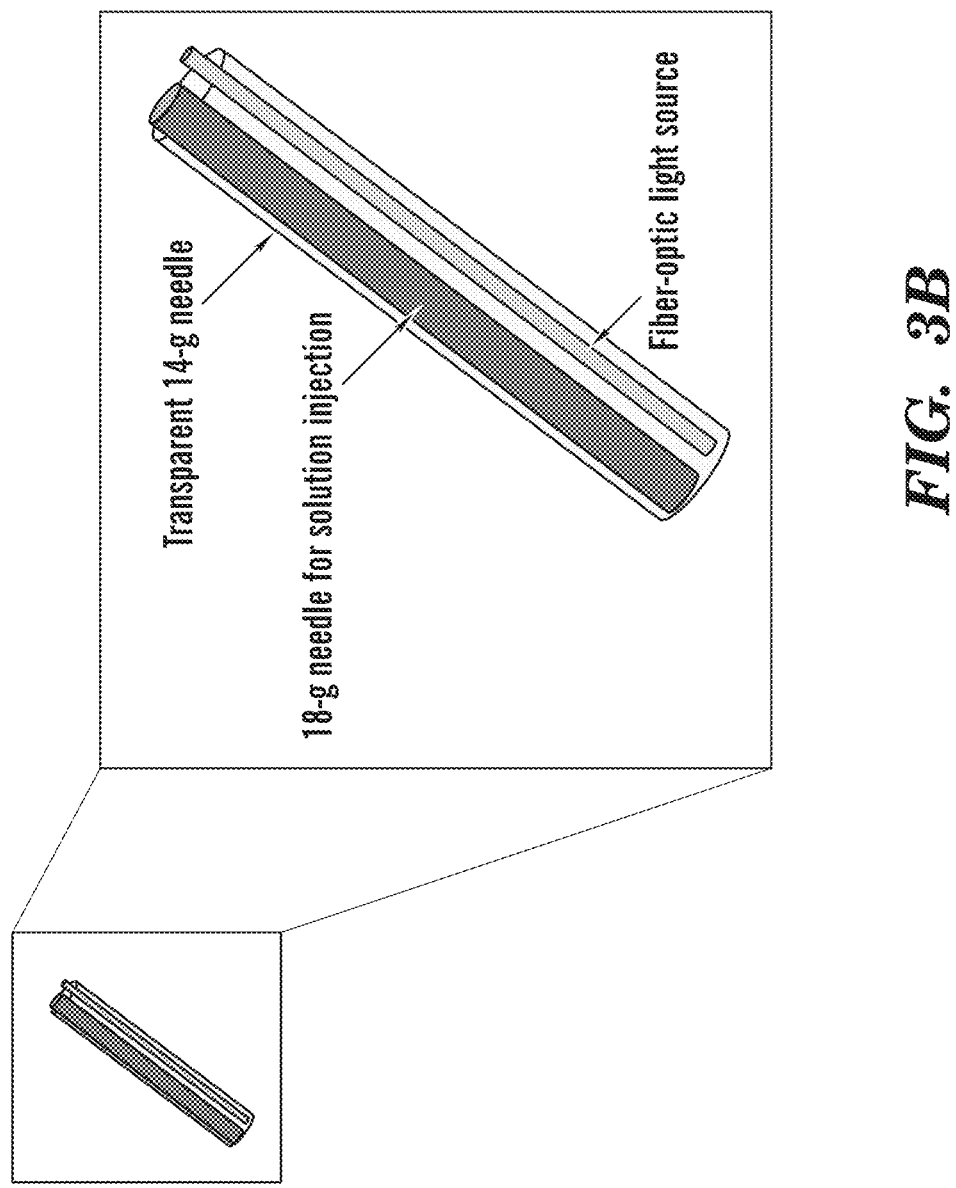
FIG. 3B is a schematic showing that the laser fiber-optic cable can be bundled together with the needle for monomer solution injection.

Example 2. Synthesis of Cartilage-Hydrogel IPN Containing pMPC in a Whole Knee Joint FIG. 3A is a schematic showing a procedure for the synthesis of cartilage-hydrogel IPN containing pMPC in a whole knee joint. Lapine hindlimb knee joints were exposed to an aqueous solution containing 2-methacryloyloxyethyl phosphorylcholine (MPC) (20 w/v %), ethylene glycol dimethacrylate (1 mol % of MPC), eosin y (0.1 mM), triethanolamine (115 mM), and N-vinyl pyrrolidone (75 mM), and incubated for 24 hours. Exposure of the solution to the joint was performed either by direct injection of the solution into the intraarticular space with a 25 gauge needle under fluoroscopic guidance or by a single microsurgical incision to directly visualize the cartilaginous surfaces and menisci. While the joints were still articulated, microsurgical incisions on both the lateral and medial sides were made to allow the irrigation of the synovial space with saline for no more than 10 seconds. A laser fiber-optic cable was inserted. FIG. 3B is a schematic showing that the laser fiber-optic cable can be bundled together with the needle for monomer solution injection. The knee joint was irradiated with 514 nm light using the fiber optic cable, and then rinsed for 2 days in saline to wash out residual non-reacted monomer.

Example 3. Synthesis of Cartilage-Hydrogel IPN Containing MPC in a Lapine Tibial Plateau A lapine tibial plateau was exposed to an aqueous solution containing 2-methacryloyloxyethyl phosphorylcholine (MPC) (60 w/v %), ethylene glycol dimethacrylate (1 mol % of MPC), eosin y (0.1 mM), triethanolamine (115 mM), and N-vinyl pyrrolidone (75 mM), and incubated for 24 hours. The tibia was removed from solution, irradiated with a 514 nm argon ion laser (500 mW/cm$^2$, 7.5 min), and rinsed for 2 days in saline to wash out residual non-reacted monomer.

Figure 4:
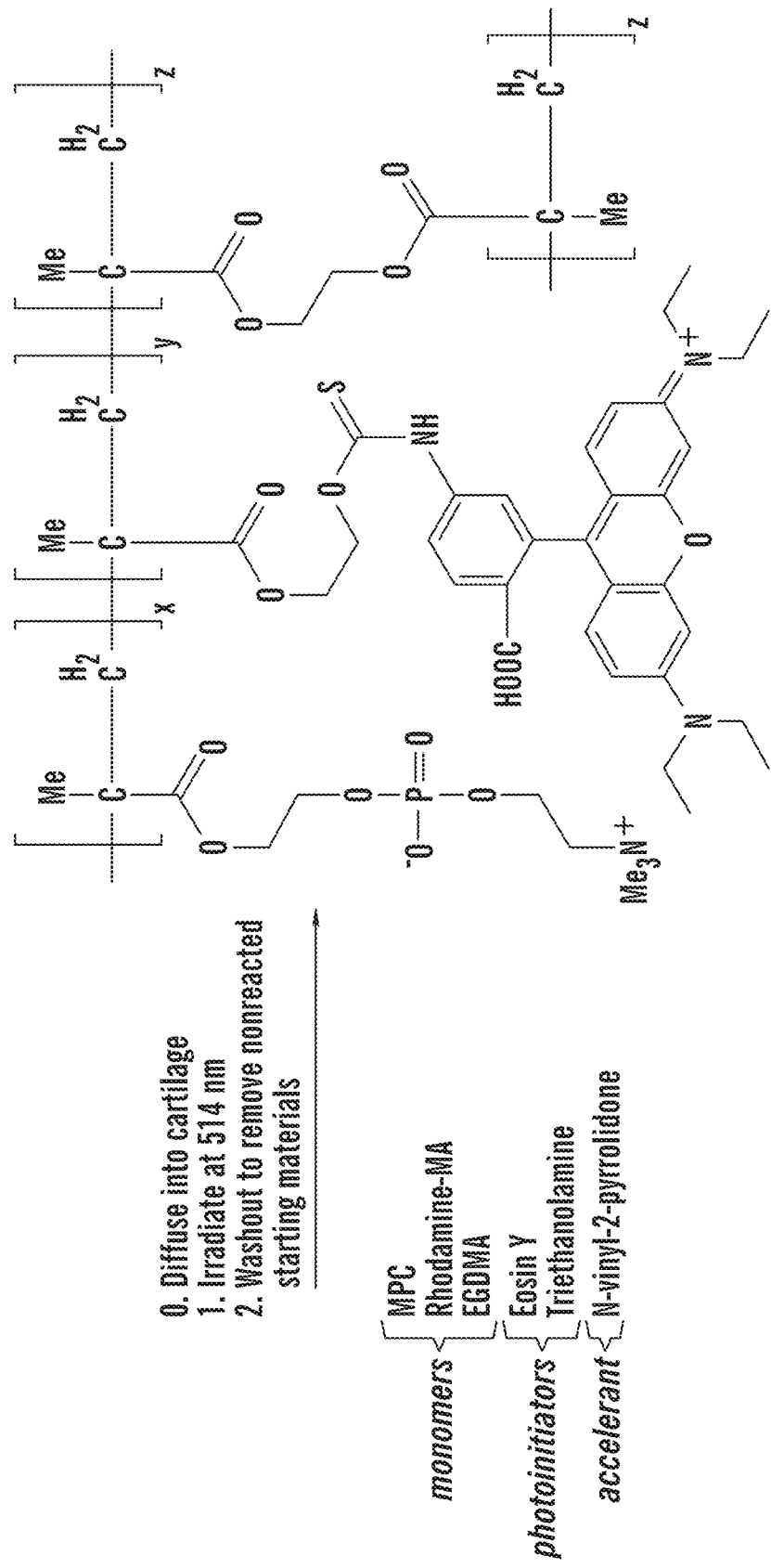
FIG. 4 shows the chemical structure of the hydrogel formed from the starting materials.

Example 4. Synthesis of Cartilage-Hydrogel IPN Containing pMPC and a Covalently Incorporated Rhodamine Derivative Bovine osteochondral explants were incubated for 24 hours in the dark in an aqueous solution containing 2-methacryloyloxyethyl phosphorylcholine (MPC) (20 w/v %), ethylene glycol dimethacrylate (1 mol % of MPC), methacryloyloxyethyl thiocarbamoyl Rhodamine B (100 μM) eosin y (0.1 mM), triethanolamine (115 mM), and N-vinyl pyrrolidone (75 mM). The explants were removed from solution, irradiated with a 514 nm argon ion laser (500 mW/cm$^2$, 7.5 min), and rinsed for 2 days in saline to wash out residual non-reacted monomer. FIG. 4 shows the chemical structure of the hydrogel formed from the starting materials.

Example 5. Synthesis of Cartilage-Hydrogel IPN Containing pPEGMA

Bovine osteochondral explants were incubated for 24 hours in the dark in an aqueous solution containing PEGMA, average $M_n$ 360 Da (20 w/v %), ethylene glycol dimethacrylate (1 mol % of PEGMA), eosin y (0.1 mM), triethanolamine (115 mM), and N-vinyl pyrrolidone (75 mM). The explants were removed from solution, irradiated with a 514 nm argon ion laser (500 mW/cm$^2$, 7.5 min), and rinsed for 2 days in saline to wash out residual non-reacted monomer.

Example 6. Synthesis of Cartilage-Hydrogel IPN Containing Both pMPC and pPEGMA

Bovine osteochondral explants were incubated for 24 hours in the dark in an aqueous solution containing MPC (10 w/v %) PEGMA, average $M_n$ 360 Da (10 w/v %), ethylene glycol dimethacrylate (1 mol % of combined MPC and PEGMA), eosin y (0.1 mM), triethanolamine (115 mM), and N-vinyl pyrrolidone (75 mM). The explants were removed from solution, irradiated with a 514 nm argon ion laser (500 mW/cm$^2$, 7.5 min), and rinsed for 2 days in saline to wash out residual non-reacted monomer.

Example 7. Synthesis of Cartilage-Hydrogel IPN Containing pPEGDA

Bovine osteochondral explants were incubated for 24 hours in the dark in an aqueous solution containing PEGDA, average $M_n$ 20,000 Da (20 w/v %), ethylene glycol dimethacrylate (1 mol % of PEGDA), eosin y (0.1 mM), triethanolamine (115 mM), and N-vinyl pyrrolidone (75 mM). The explants were removed from solution, irradiated with a 514 nm argon ion laser (500 mW/cm$^2$, 7.5 min), and rinsed for 2 days in saline to wash out residual non-reacted monomer.

Example 8. Synthesis of Crosslinked MPC Polymer

An aqueous solution of MPC (5 w/v %), ethylene glycol dimethacrylate (1 mol % of MPC), ammonium persulfate (0.1 mol % of MPC), and tetramethylethylenediamine (0.2 mol % of MPC) was allowed to incubate for 24 hours. The resulting solution was viscous and lubricious.

Example 9. Physical Properties of Crosslinked MPC Polymer

Figure 5A:
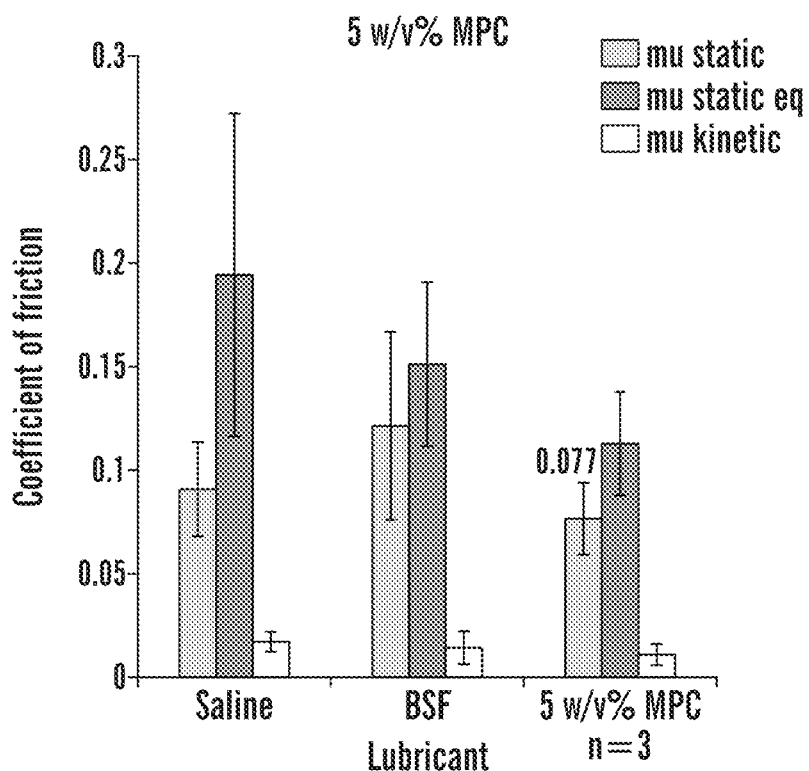
FIG. 5A shows coefficients of friction for saline, BSF, and a 5 w/v % solution of MPC-based crosslinked polymer as boundary lubricants for cartilage-on-cartilage torsional friction testing. For each group of columns, from left to right: mu static, mu static eq, mu kinetic.
Figure 5B:
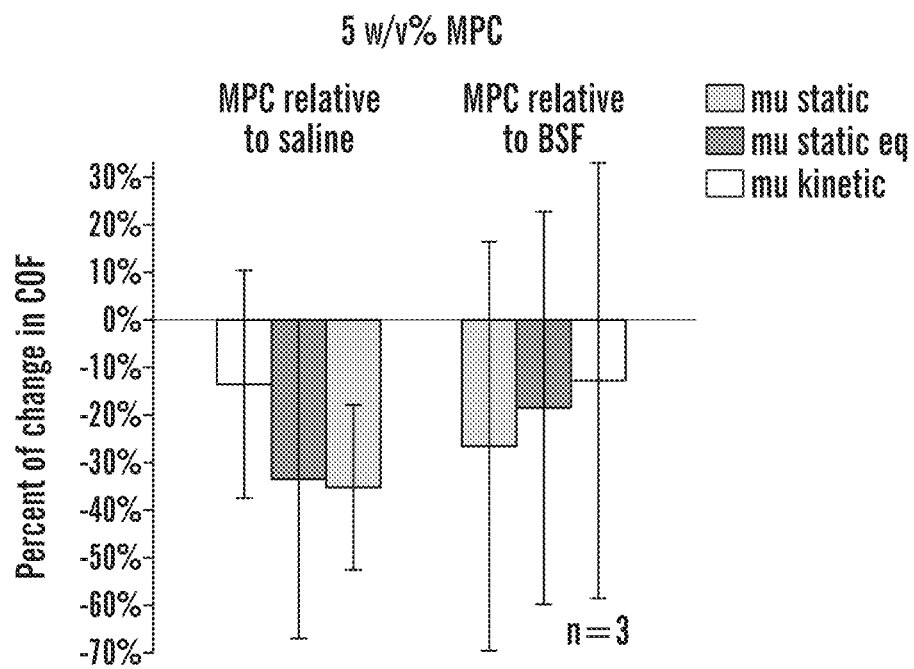
FIG. 5B shows the percent difference in coefficient of friction of the MPC-based polymer solution compared to saline and compared to BSF. For each group of columns, from left to right: mu static, mu static eq, mu kinetic.

Cartilage-on-cartilage torsional coefficient of friction with crosslinked MPC polymer as lubricant was determined by the following procedure: (a) Bovine osteochondral explants were incubated with the inventive polymer for 24 hours, then mounted in a dynamic mechanical testing apparatus with their cartilage surfaces in contact with one another. (b) A surrounding bath of the inventive polymer solution was exposed to the cartilage interface. (c) After application of a 5 N pre-load to ensure full contact between the surfaces, the cartilage was compressed to 18% strain and allowed to dwell for 45 minutes. (d) The explants were then subjected to 720° rotation at 5°/sec. (e) Coefficients of friction were calculated from the collected force, torque, and displacement data (FIGS. 5A and 5B).

Figure 6A:
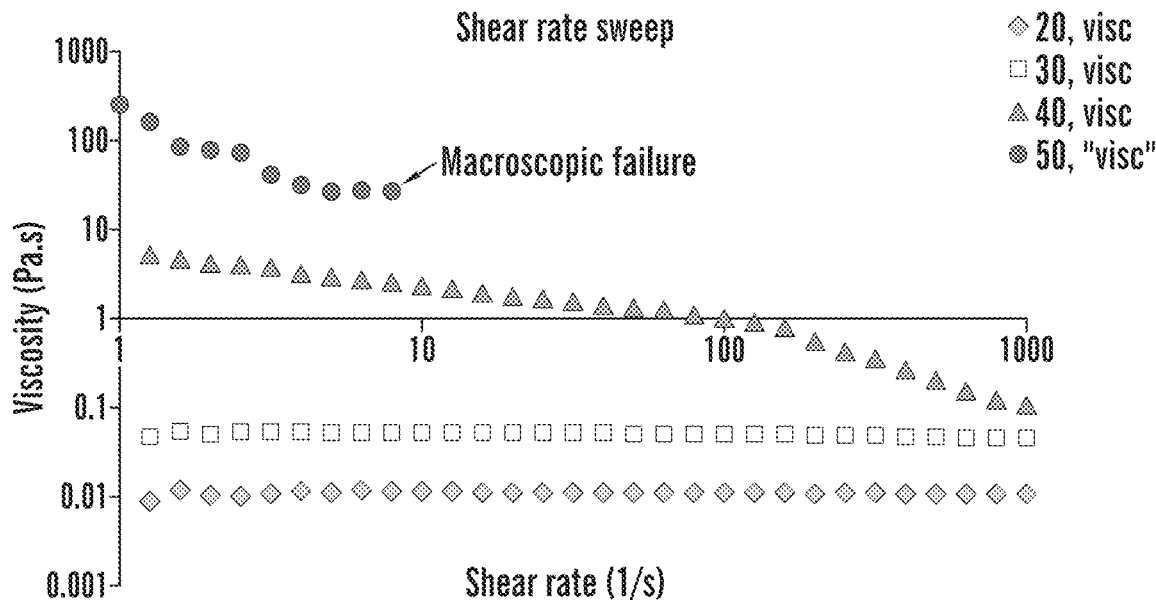
FIG. 6A shows viscosity data for 20, 30, 40, and 50 w/v % solutions of MPC-based polymers.
Figure 6B:
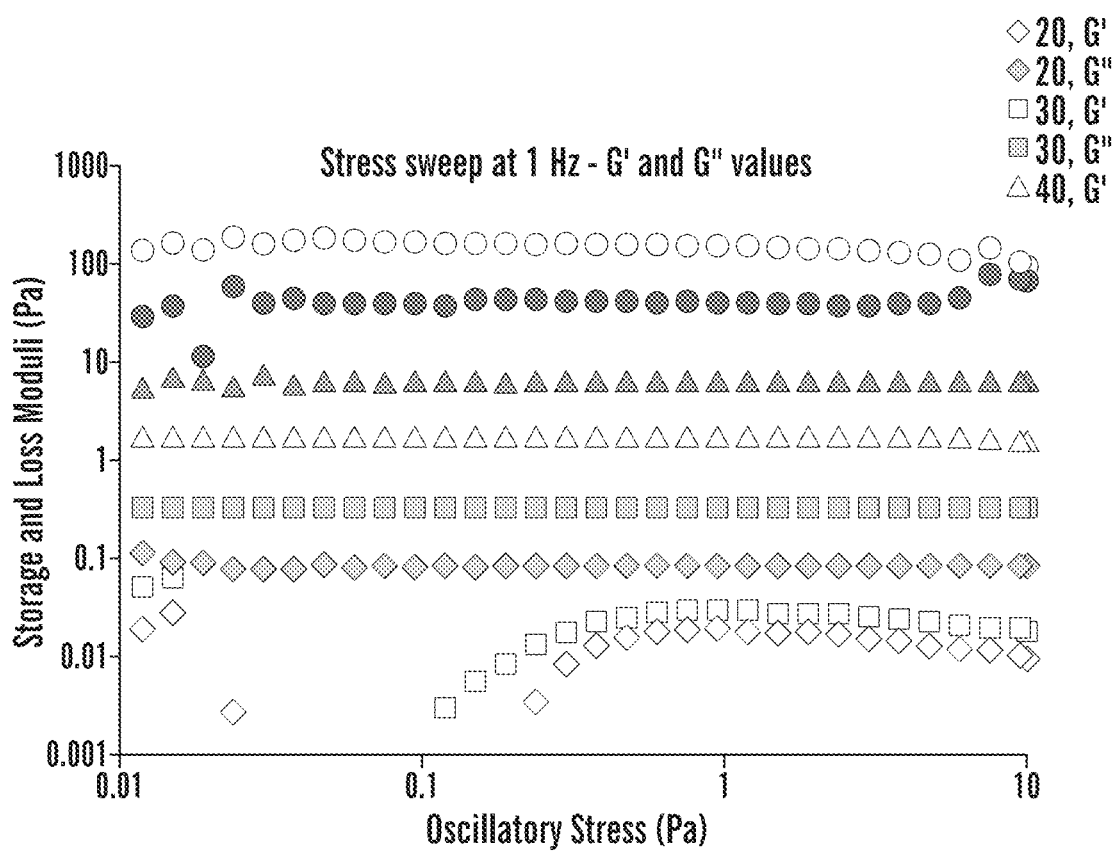
FIG. 6B shows storage and loss moduli for 20, 30, 40, and 50 w/v % solutions of MPC-based polymers.

Viscosity and storage and loss moduli of crosslinked MPC polymer were determined by the following procedure: (a) Measurements were performed on a RA 1000 controlled strain rheometer from TA Instrument equipped with a peltier temperature control. A 40 mm diameter steel plate with a 20 angle with a gap of 47 µm was used. (b) A continuous flow shear rate sweep (from 1 to 1000/sec) with a controlled strain for a linear response was performed at 25° C. (FIG. 6A). This measures the viscosity of the material. (c) An oscillatory stress sweep (from 0.01 to 10 Pa) at a frequency of 1 Hz was also performed to measure the storage and loss moduli of the material (FIG. 6B).

Figure 21A:
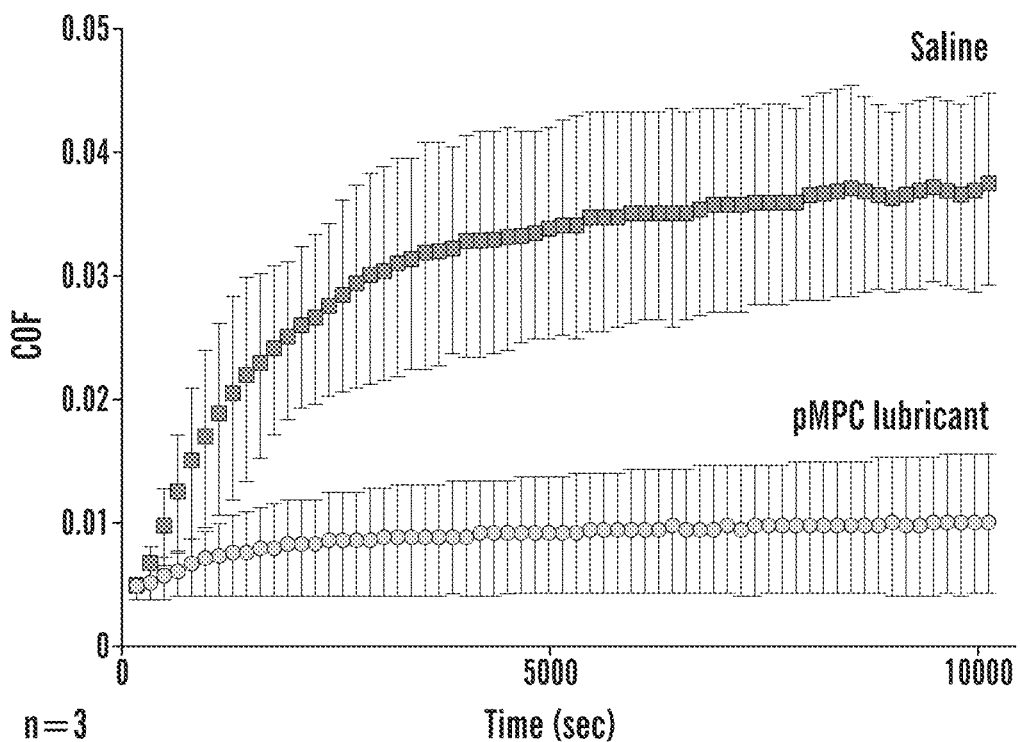
FIG. 21A displays the average coefficients of friction (COFs) over the course of a long-duration friction test under constant load, for two groups of osteochondral plug pairs lubricated by either saline or pMPC lubricant.
Figure 21B:
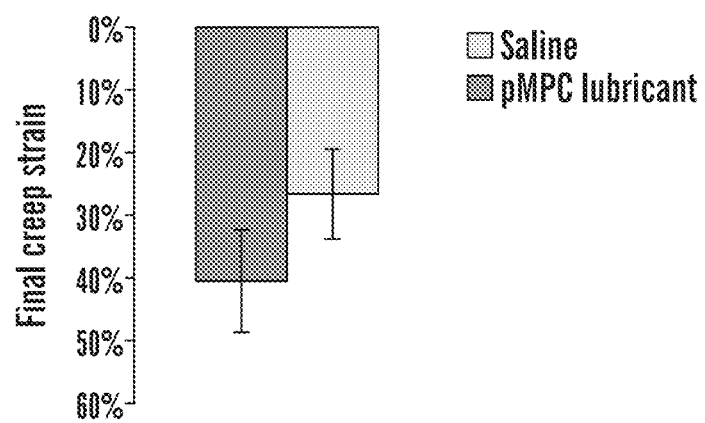
FIG. 21B displays the average final equilibrium creep strain upon completion of a long-duration friction test under constant load, for two groups of osteochondral plug pairs lubricated by either saline or pMPC lubricant.
Figure 22A:
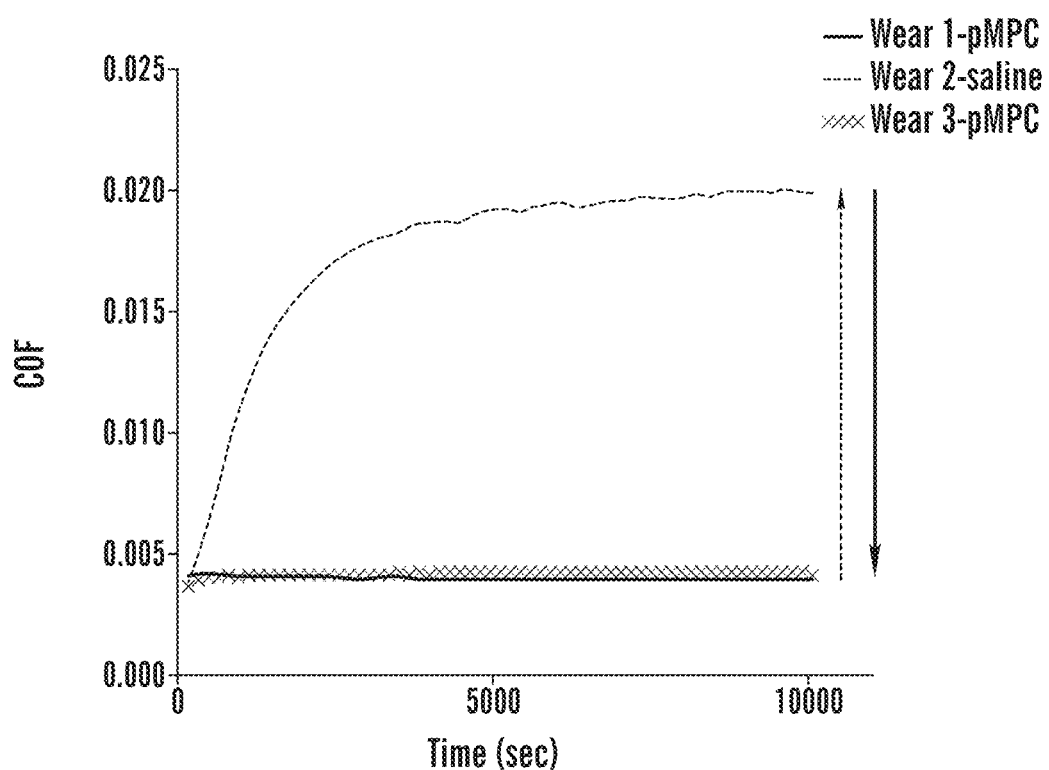
FIG. 22A displays a single plug pair's COF under lubrication, in succession, by pMPC lubricant, then by saline, then by pMPC lubricant again. Note that increase in COF (left arrow) from wear 1 (pMPC lubricant) to wear 2 (saline) is similar in magnitude to decrease in COF (right arrow) from wear 2 (saline) to wear 3 (pMPC lubricant), indicating a near-100% "recovery" of initial COF.
Figure 22B:
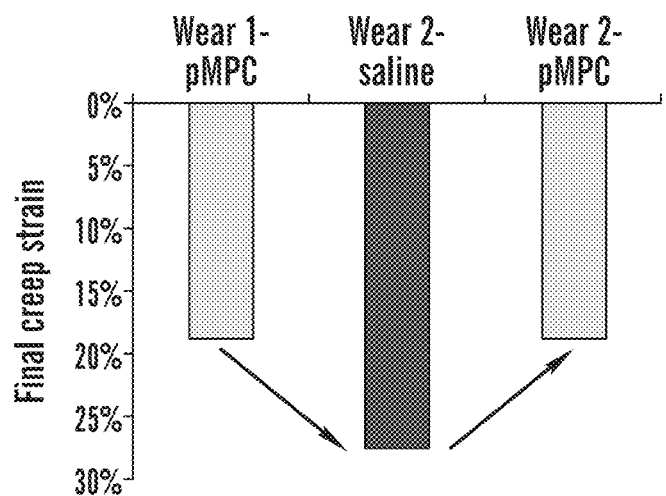
FIG. 22B displays a single plug pair's final equilibrium creep strain under lubrication, in succession, by pMPC lubricant, then by saline, then by pMPC lubricant again. Note that increase in final equilibrium creep strain (left arrow) from wear 1 (pMPC lubricant) to wear 2 (saline) is similar in magnitude to decrease in final equilibrium creep strain (right arrow) from wear 2 (saline) to wear 3 (pMPC lubricant), indicating a near-100% "recovery" of final equilibrium creep strain.

Long-duration cartilage-on-cartilage torsional coefficients of friction with crosslinked pMPC as the lubricant were determined by the following procedure: Bovine osteochondral explants were incubated with the inventive polymer for 24 hours, then mounted in a dynamic mechanical testing apparatus with their cartilage surfaces in contact with one another. A surrounding bath of the inventive polymer solution was exposed to the cartilage interface. After application of a 5 N pre-load to ensure full contact between the surfaces, the cartilage was quickly loaded to 0.78 MPa of compressive stress. This compressive stress was maintained over 10,080 rotations at an angular velocity of 360°/sec with 10-second lift-offs every 160 sec to allow reintroduction of lubricant solution to the cartilage surfaces. The effective velocity of the rotation speed used was 22 mm/sec around the perimeter of the osteochondral plugs. Coefficients of friction were calculated from the collected force and torque data and tissue strain was calculated from the collected displacement data. In one set of experiments, the COFs and final creep strains of two groups of explants, each incubated in a different lubricant (either saline or pMPC lubricant), were compared (FIGS. 21A-21B). In another set of experiments, the COFs and final creep strains of a single set of explants were compared as the set of explants was lubricated first by pMPC lubricant, then by saline, then by pMPC lubricant once again. (FIGS. 22A-22B)

Example 10. Physical Properties of Cartilage-Hydrogel IPN

IPN-on-stainless-steel torsional coefficient of friction under boundary mode lubrication was determined by the following procedure: (a) An osteochondral explant treated with the inventive method was mounted in a dynamic mechanical testing apparatus. (b) After application of a 5 N pre-load to ensure full contact between the cartilaginous and steel surfaces, the sample was compressed to 18% strain and allowed to dwell for 45 minutes. (c) The sample was then subjected to 720° rotation at 5°/sec. (d) Coefficients of friction were calculated from the collected force, torque, and displacement data.

IPN-on-stainless-steel torsional coefficient of friction under elastohydrodynamic mode lubrication was determined by the following procedure: (a) An osteochondral explant treated with the inventive method was mounted in a dynamic mechanical testing apparatus. (b) After application of a 5 N pre-load to ensure full contact between the cartilaginous and steel surfaces, the sample endured a simultaneous creep regimen under constant load and torsional articulation regimen at 360°/sec. (c) Coefficients of friction were calculated from the collected force, torque, and displacement data.

IPN-on-IPN rate and magnitude of wear under boundary mode lubrication was determined by the following procedure: (a) Osteochondral explants treated with the inventive method were mounted in a dynamic mechanical testing apparatus. (b) After application of a 5 N pre-load to ensure full contact between the cartilaginous surfaces, the samples were compressed to 18% strain and allowed to dwell for 45 minutes. (c) The samples were then subjected to a torsional articulation regimen at 90°/sec. (d) Coefficients of friction were calculated from the collected force, torque, and displacement data, wear debris was analyzed gravimetrically and biochemically, and the worn sample surfaces were analyzed by microscopy.

IPN-on-IPN rate and magnitude of wear under elastohydrodynamic mode lubrication was determined by the following procedure: (a) Osteochondral explants treated with the inventive method were mounted in a dynamic mechanical testing apparatus. (b) After application of a 5 N pre-load to ensure full contact between the cartilaginous surfaces, the samples endured a simultaneous creep regimen under constant load and a torsional articulation regimen at 360°/sec. (c) Coefficients of friction were calculated from the collected force, torque, and displacement data, wear debris was analyzed gravimetrically and biochemically, and the worn sample surfaces were analyzed by microscopy.

Figure 7A:
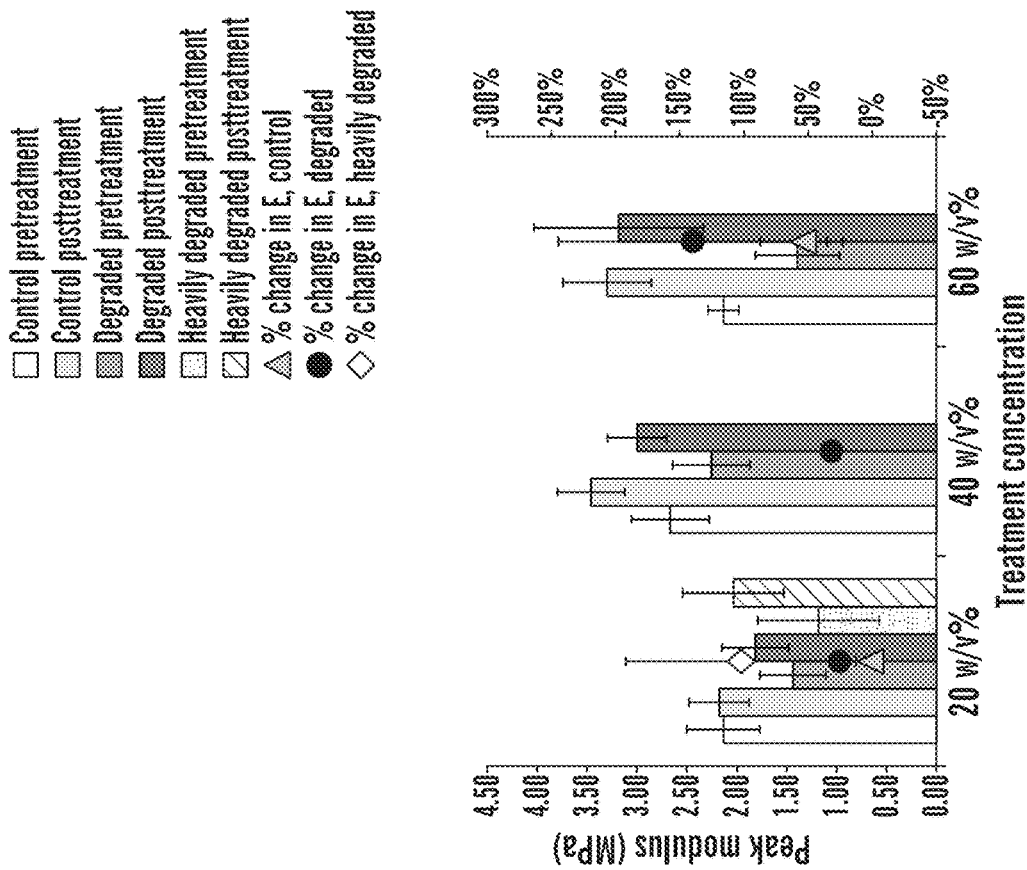
FIG. 7A shows equilibrium compressive modulus data for tissue (pretreatment) and tissue-polymer IPNs (posttreatment) following treatment with monomer solutions of 20, 40, and 60 w/v %.
Figure 7B:
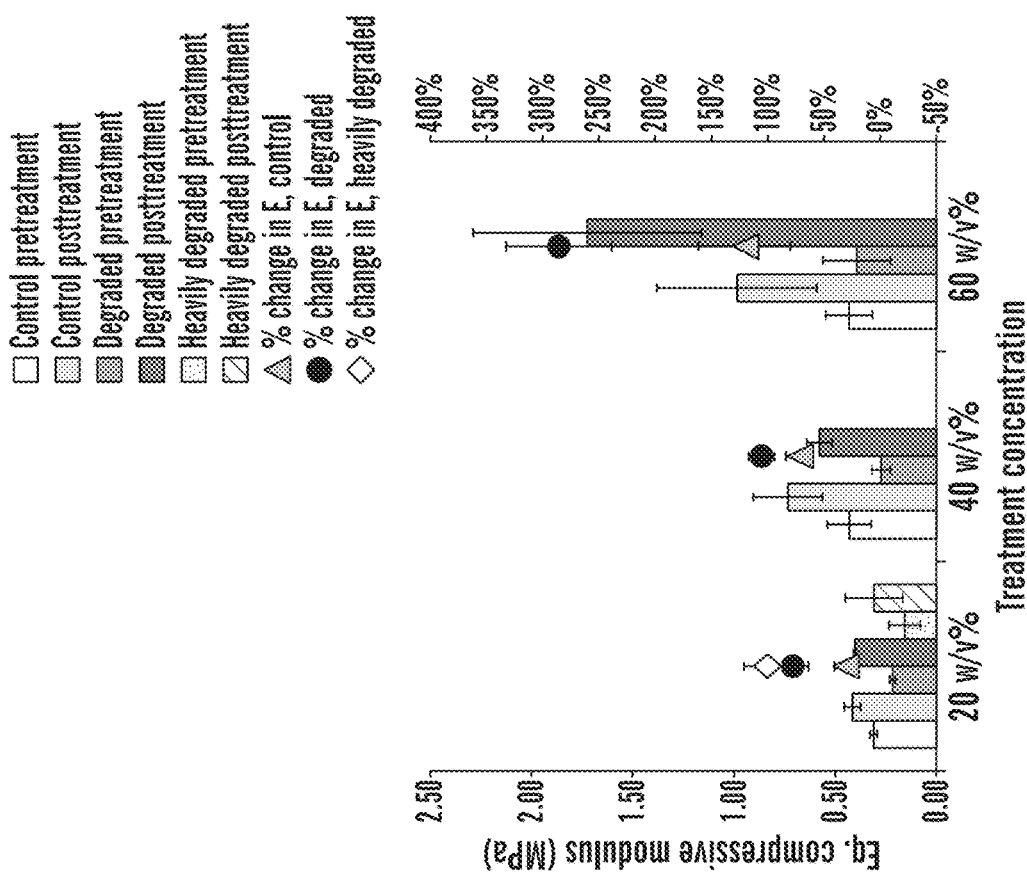
FIG. 7B shows peak modulus data for tissue (pretreatment) and tissue-polymer IPNs (posttreatment) following treatment with monomer solutions of 20, 40, and 60 w/v %. The legends in FIG. 7B are the same as the ones in FIG. 7A.
Figure 7C:
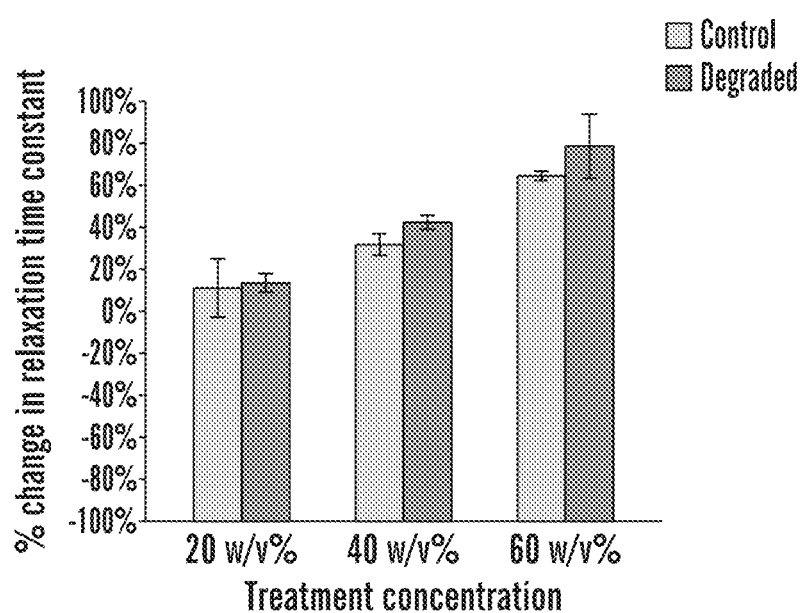
FIG. 7C shows the percentage of change in relaxation time constant for tissue (pretreatment) and tissue-polymer IPNs (posttreatment) following treatment with monomer solutions of 20, 40, and 60 w/v %. For each group of columns, from left to right: control, degraded.
Figure 12:
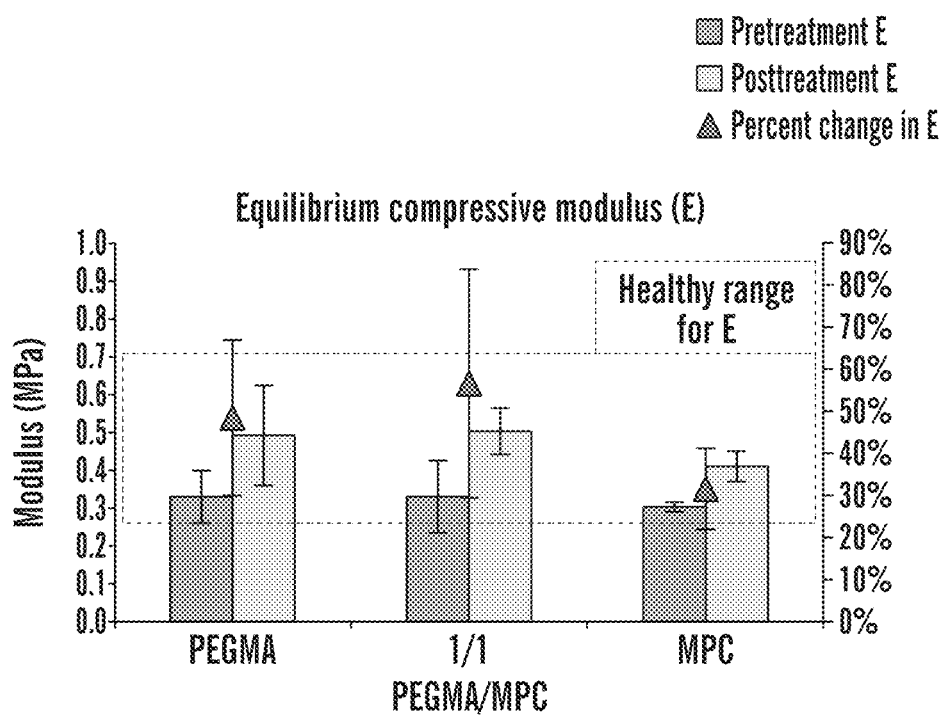
FIG. 12 shows the equilibrium compressive modulus measured from samples treated by MPC, PEGMA, or a combination of MPC and PEGMA. For each group of columns, from left to right: pretreatment E, posttreatment E.
Figure 13A:
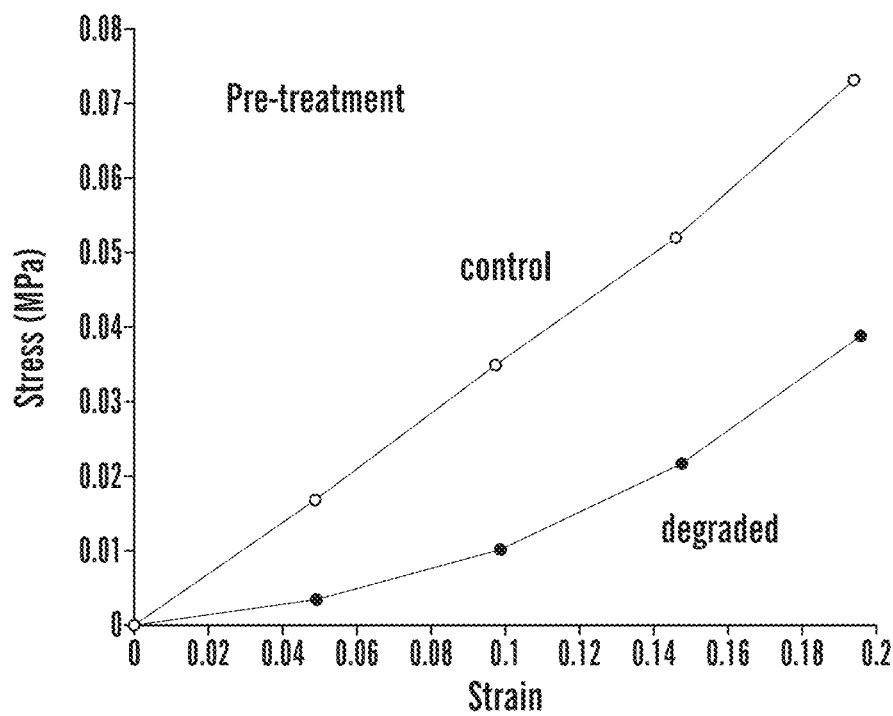
FIGS. 13A and 13B display equilibrium stress values with corresponding strain values obtained during 4-step stress relaxation compressive regimen, before (FIG. 13A) and following (FIG. 13B) IPN treatment at a monomer concentration of 20 w/v %.
Figure 13B:
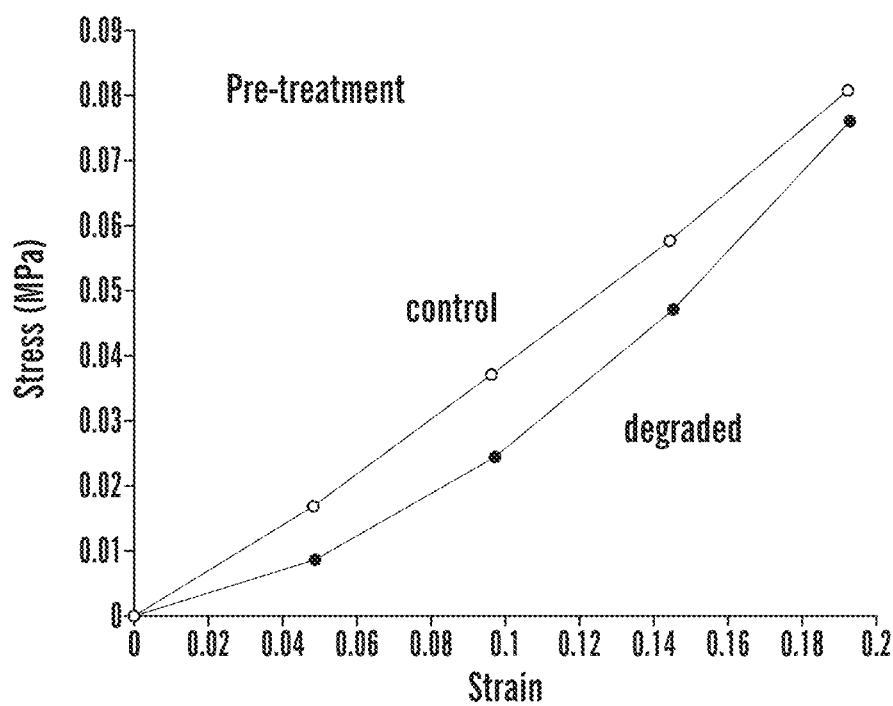
Figure 14:
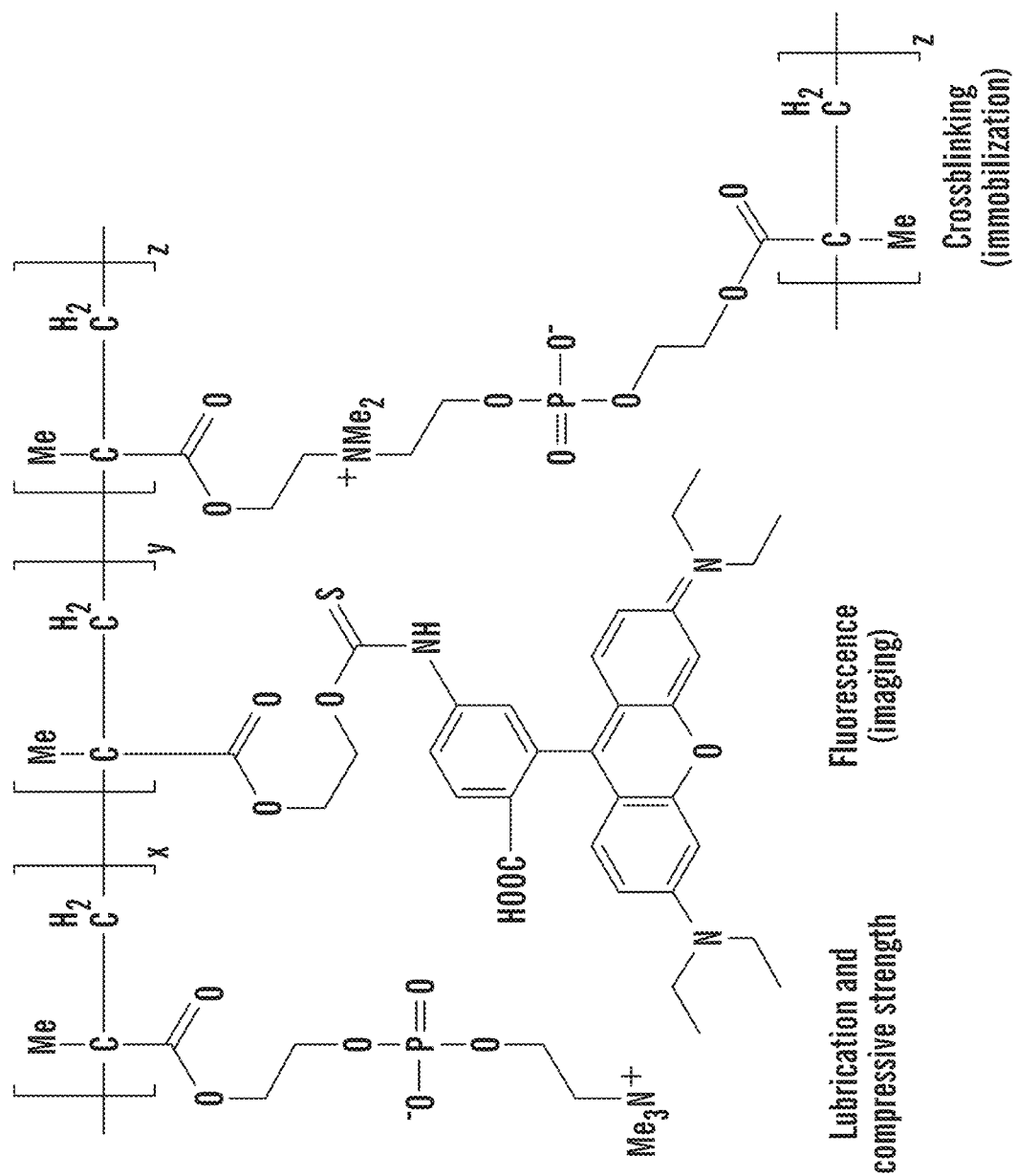
FIG. 14 shows the chemical structure of the polymer prepared according to an embodiment of the invention.
Figure 16:
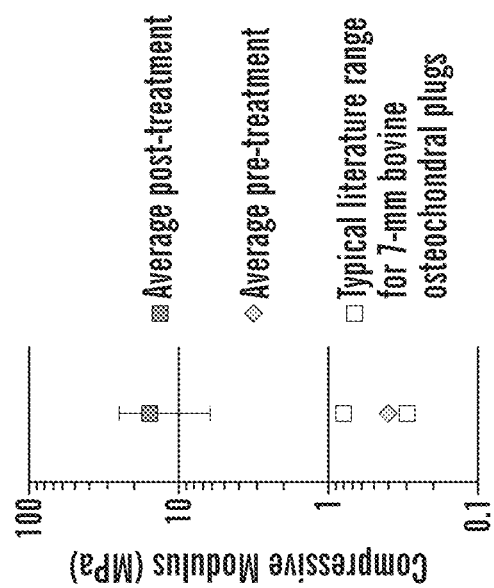
FIG. 16 shows change in equilibrium compressive modulus due to IPN treatment with monomer concentration of 75 w/v %.
Figure 15A:
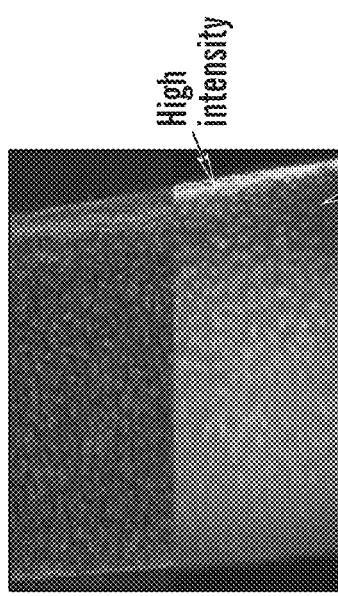
FIG. 15A shows a view along the lateral-medial axis of a sagittal slice (100 μm thick) of hydrogel-supplemented cartilage (top=phase contrast micrograph at full light spectrum, bottom=false-colored, at 580 nm detection; 10× magnification, Nikon TS100-F inverted microscope).
Figure 15B:
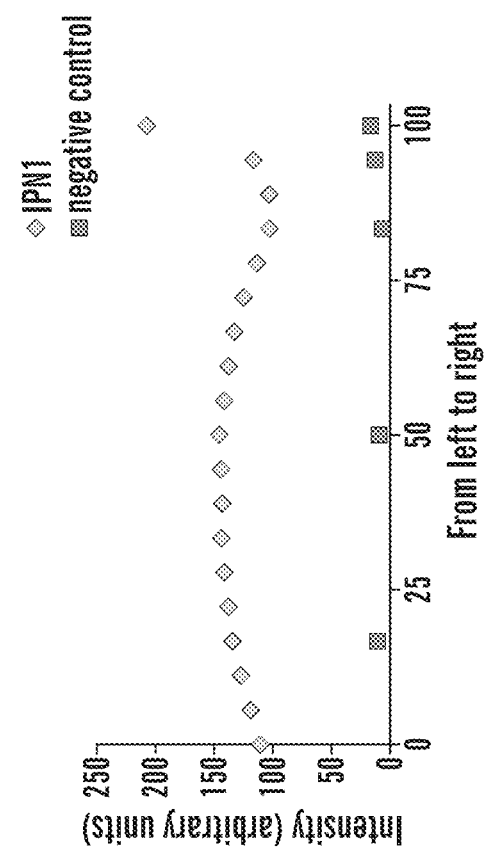
FIG. 15B is a plot of the fluorescence intensity at 580 nm detection of the polymer shown in FIG. 14 and of a slice of native, untreated cartilage ("negative control") of equal dimensions and orientation are also shown. Polymer shown in FIG. 14 fluoresces at 580 nm with ca. 12 times the intensity of the negative control.

IPN compressive properties, namely, equilibrium compressive modulus, peak force modulus, dynamic modulus, and stress relaxation time constants were determined by the following procedure depending on the sample:

For an osteochondral explant: (a) An osteochondral explant treated with the inventive method was mounted in a dynamic mechanical testing apparatus. (b) After application of a 5 N pre-load to ensure full contact between the cartilaginous surface and the opposing platen, a four-step unconfined stress-relaxation regimen was performed, compressing the sample by 5% strain at each step with a strain rate of 0.333%/sec, with 75 minute relaxation periods between each compression step. (c) Equilibrium compressive modulus was obtained by plotting equilibrium stress values against strain (FIG. 7A), peak force modulus by plotting peak stress values against strain (FIG. 7B), dynamic modulus at a given compression step by plotting stress immediately before and immediately after compression against the strain before and after compression, and stress relaxation time constants for a given compression step by fitting the stress relaxation curve to an exponential equation using curve-fitting software (FIG. 7C). Using a similar procedure, the equilibrium compressive modulus was measured from samples treated by MPC, PEGMA, or a combination of MPC and PEGMA (FIG. 12). Note: the data shown in FIGS. 7A-7C is for osteochondral explants.

Figure 8:
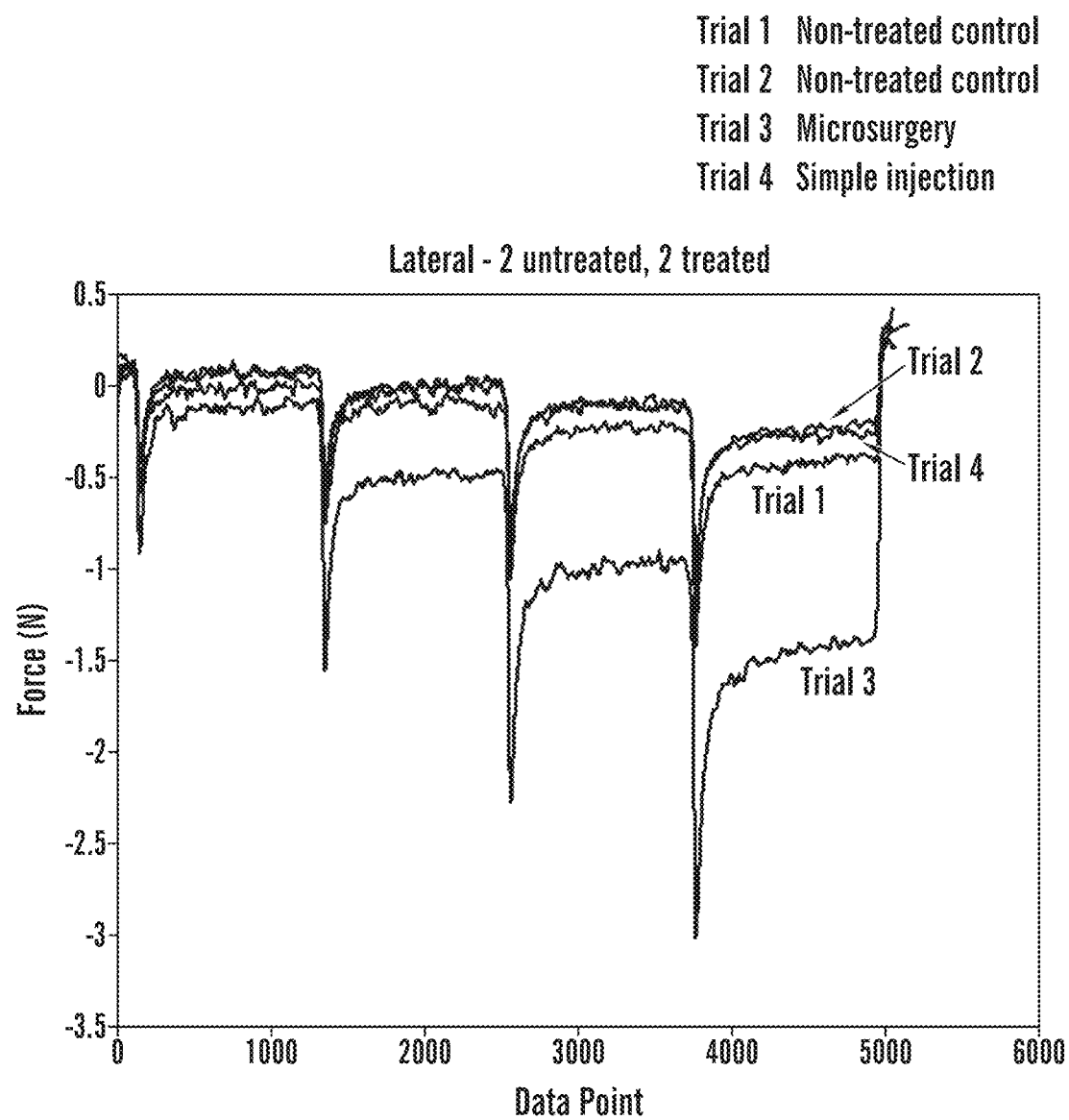
FIG. 8 displays the resulting force during a 4-step stress relaxation compressive regimen using a 1-mm diameter stainless steel indenter tip on lapine tibias. Trials 1 and 2 are non-treated tibias from the same rabbit. Trial 3 is a knee treated by microsurgery from lateral side (removed lateral meniscus and could see where we were getting the monomer solution). Trial 4 is a knee treated by 1 injection from lateral side and 1 injection from medial side; joint ballooned up as expected. For photopolymerization, removed tissue on both sides of joint, leaving patellar tendon and fat pad, and leaving tissue at back of knee.

For a lapine tibia treated before disarticulation: (a) A lapine tibia was excised from a whole joint that was treated as described in Example 2. (b) The tibia was potted in polymethylmethacrylate and mounted in a dynamic mechanical testing apparatus. (c) After application of a 3 N pre-load to ensure full contact between the cartilaginous surface and the opposing platen, a four-step unconfined stress-relaxation regimen was performed, compressing the sample by 5% strain at each step with a strain rate of 20%/sec, with 2 minute relaxation periods between each compression step (FIG. 8). (d) Equilibrium compressive modulus was obtained by plotting equilibrium stress values against strain, peak force modulus by plotting peak stress values against strain, dynamic modulus at a given compression step by plotting stress immediately before and immediately after compression against the strain before and after compression, and stress relaxation time constants for a given compression step by fitting the stress relaxation curve to an exponential equation using curve-fitting software.

Figure 17:
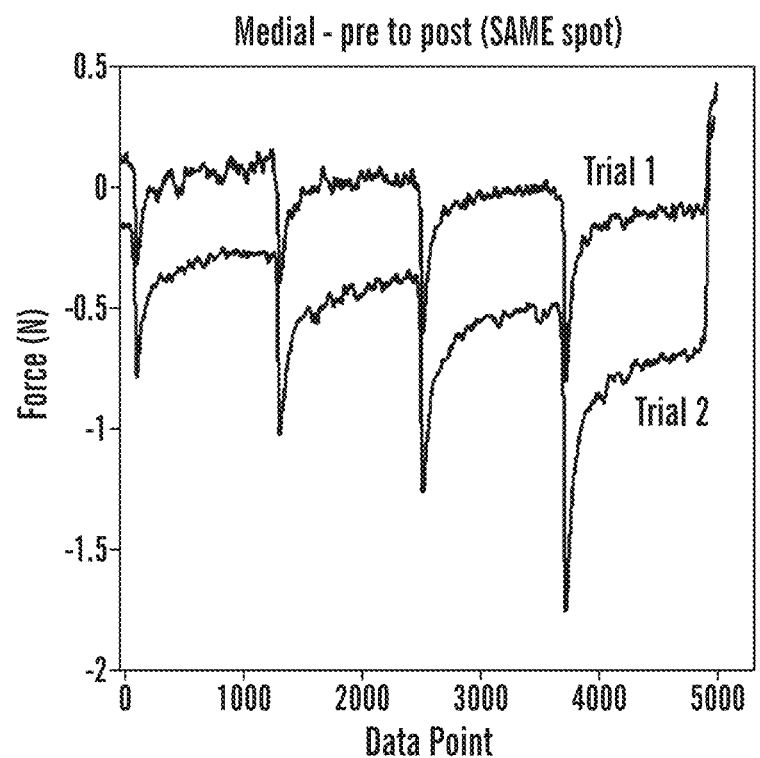
FIG. 17 shows the resulting force during a 4-step stress relaxation compressive regimen using a 1-mm diameter stainless steel indenter tip on the same lapine tibia, in the same location on said tibia, prior to and following IPN treatment. Trial 1 corresponds to the force data prior to treatment; Trial 2 corresponds to the force data following treatment. A marked increased in the force withheld was observed following treatment.

For a Lapine Tibia Treated after Disarticulation:

(a) A lapine tibia was excised from a whole joint. (b) The tibia was potted in polymethylmethacrylate and mounted in a dynamic mechanical testing apparatus. (c) After application of a 3 N pre-load to ensure full contact between the cartilaginous surface and the opposing platen, a four-step unconfined stress-relaxation regimen was performed, compressing the sample by 5% strain at each step with a strain rate of 20%/sec, with 2 minute relaxtion periods between each compression step (FIG. 17). (d) The cartilaginous surface (proximal end) of the tibia was treated as described in Example 3, and the aforementioned compressive regimen was repeated on the same region of the tibial surface as was tested before treatment. Testing of the same location on the tibial plateau was achieved by leaving the osteochondral sample in the mechanical testing apparatus while the treatment procedure occurred. (e) Equilibrium compressive modulus was obtained by plotting equilibrium stress values against strain, peak force modulus by plotting peak stress values against strain, dynamic modulus at a given compression step by plotting stress immediately before and immediately after compression against the strain before and after compression, and stress relaxation time constants for a given compression step by fitting the stress relaxation curve to an exponential equation using curve-fitting software.

Example 11. Biochemical Properties of Cartilage-Hydrogel IPN

Figure 9A:
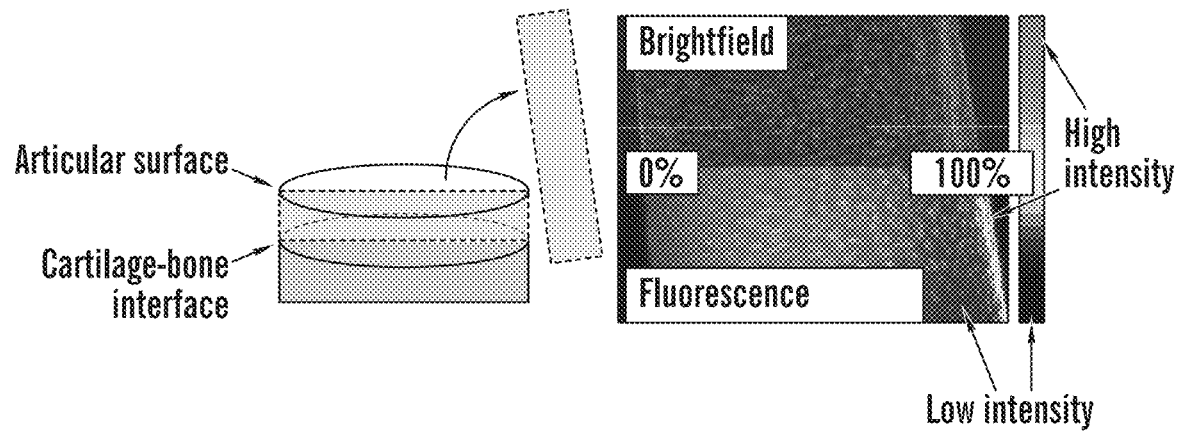
FIG. 9A is a view along the lateral-medial axis of a sagittal slice (100 μm thick) of hydrogel-supplemented cartilage. The bright field image is a phase contrast micrograph at full light spectrum. The fluorescence image is false-colored, at 580 nm detection (10× magnification, Nikon TS100-F inverted microscope).
Figure 9B:
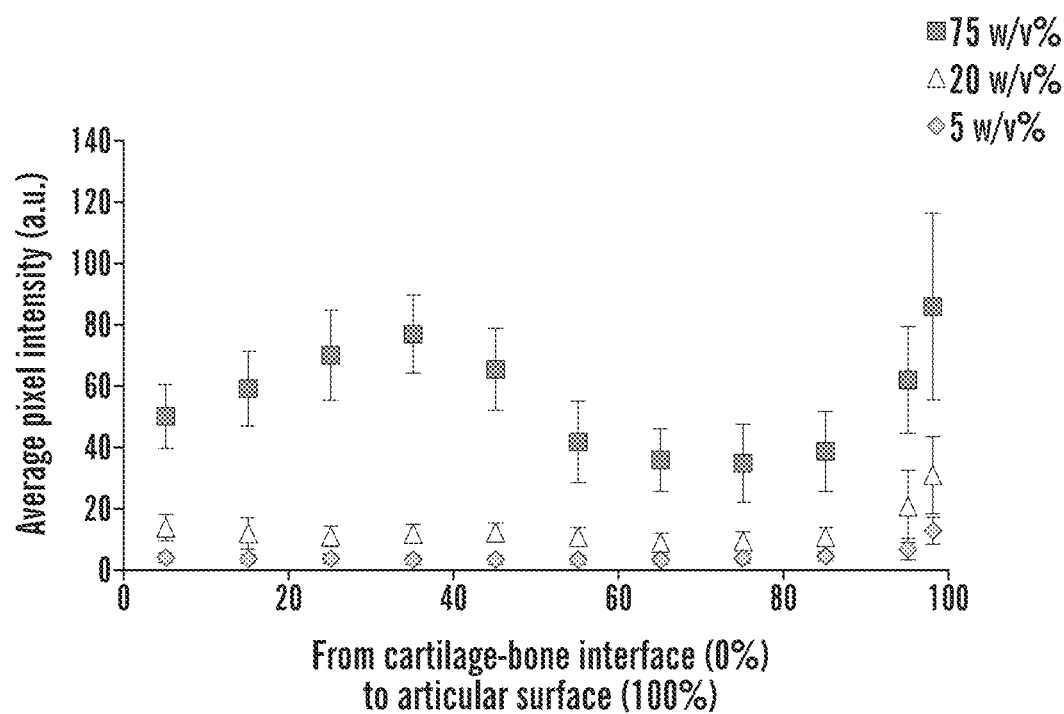
FIG. 9B displays fluorescence intensity over the region of cartilage progressing from the cartilage-bone interface to the articular surface.
Figure 18:
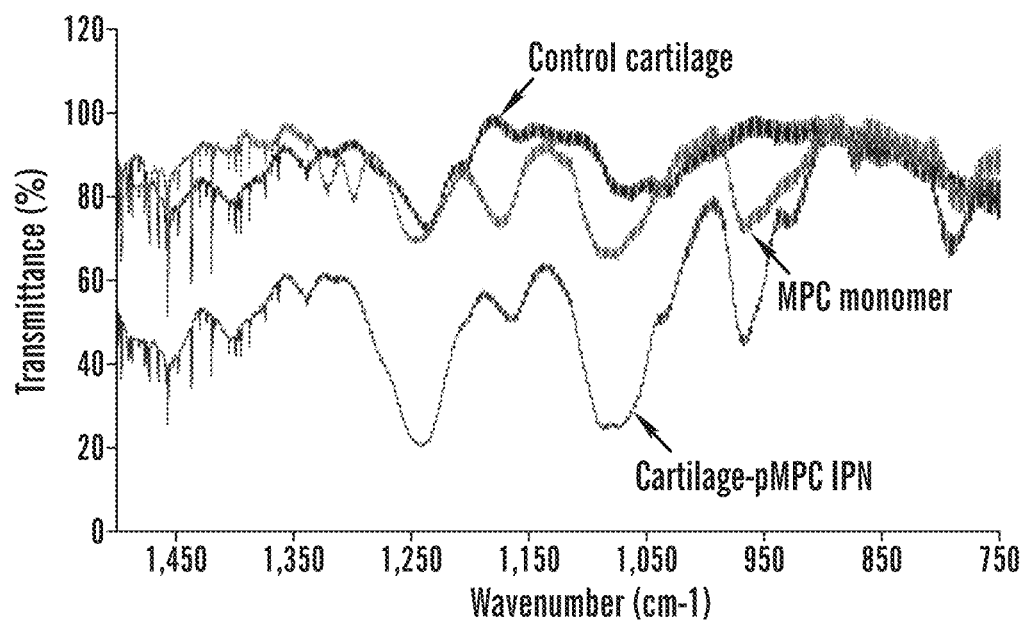
FIG. 18 shows the Fourier transform infrared spectra of 10-um histological slices of the following samples mounted onto potassium bromide crystals: control cartilage, MPC monomer, and cartilage-pMPC IPN. Absorbance at 1243 $cm^{-1}$ corresponds to P=O, absorbance at 1086 $cm^{-1}$ corresponds to P—O, and absorbance at 967 $cm^{-1}$ corresponds to NMe3.
Figure 19A:
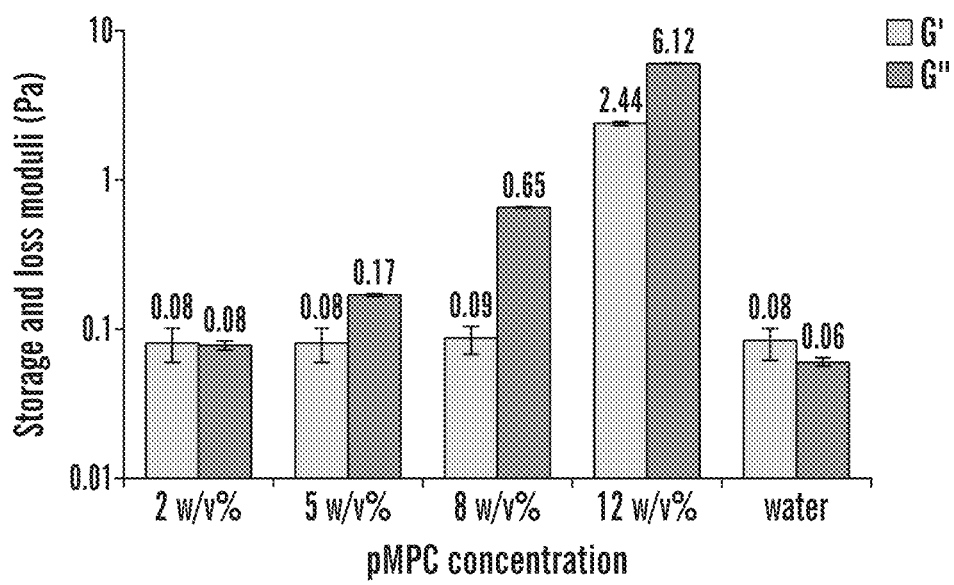
FIG. 19A displays storage and loss moduli (G' and G", respectively) of pMPC lubricants at various concentrations, all with a crosslinking density of 1% mol per mol monomer. For each set of columns, from left to right: G', G".
Figure 19B:
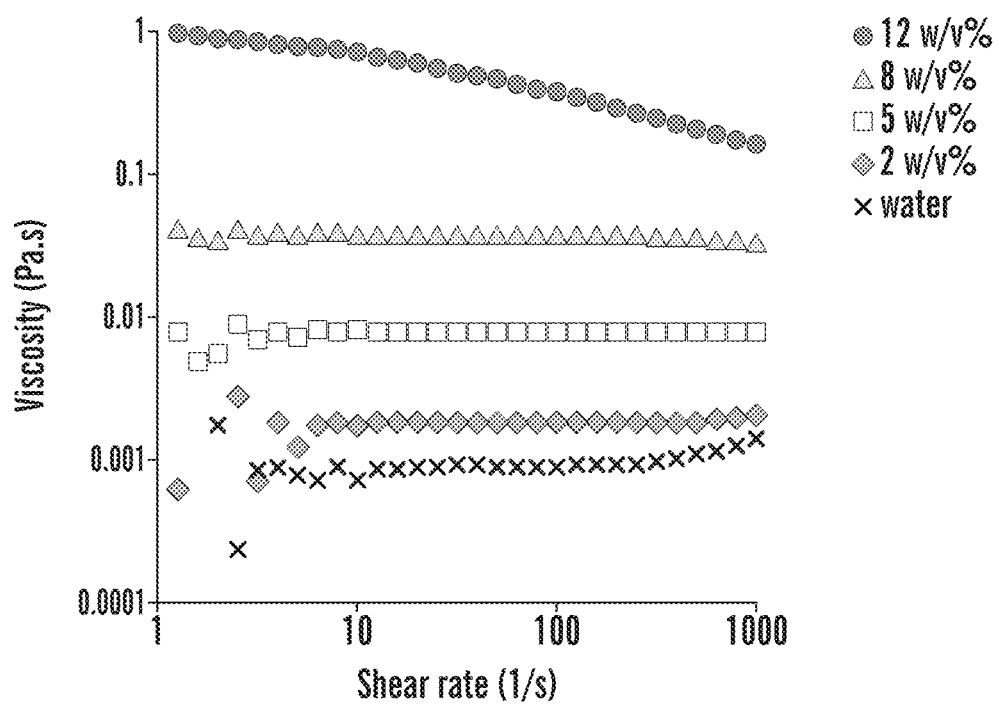
FIG. 19B displays viscosity as a function of shear rate for pMPC lubricants at various concentrations, all with a crosslinking density of 1% mol per mol monomer.
Figure 20A:
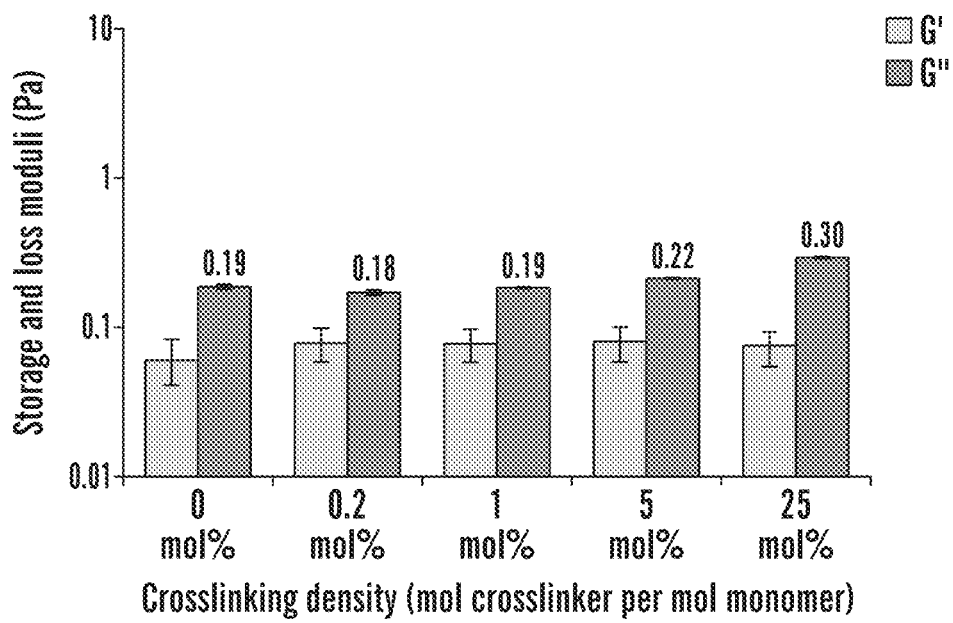
FIG. 20A displays storage and loss moduli (G' and G", respectively) of pMPC lubricants at concentrations of 5 w/v %, each with a varying density of crosslinking. For each set of columns, from left to right: G', G".
Figure 20B:
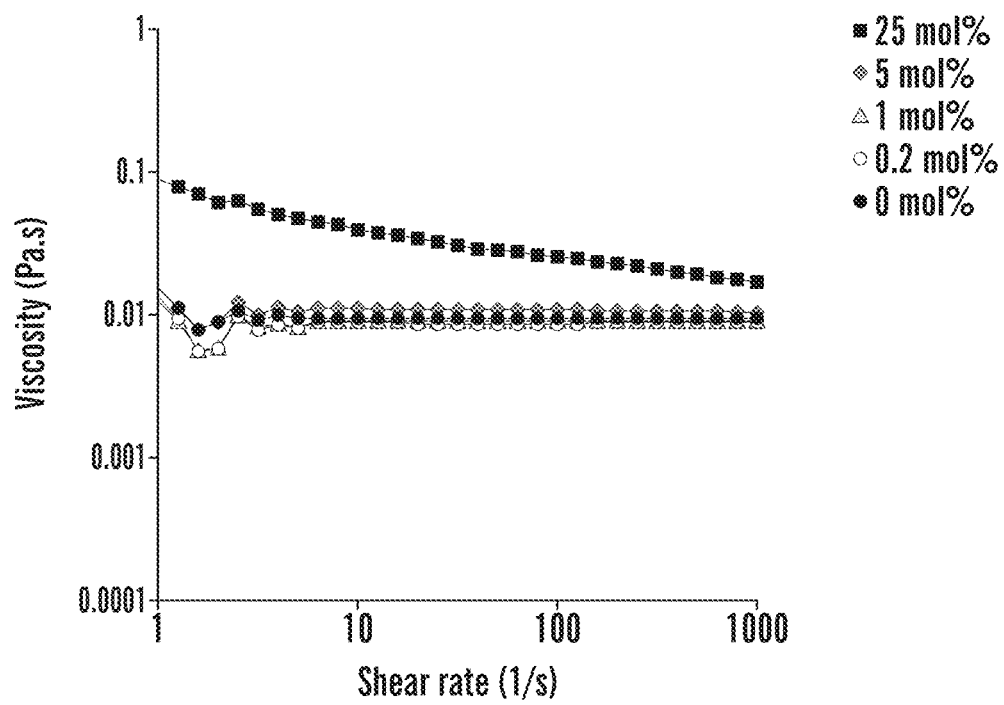
FIG. 20B displays viscosity as a function of shear rate for pMPC lubricants at concentrations of 5 w/v %, each with a varying density of crosslinking.

Infrared spectroscopy was performed to detect the change in the presence of phosphate functional groups following treatment of cartilage with MPC-containing hydrogel IPN treatment, as well as the change in the presence ether oxygen functional groups following treatment with PEG-containing hydrogel IPN treatment (FIG. 18). Histology was performed following decalcification, staining with hematoxylin and eosin, Masson's Trichrome, and Safranin-O. Fluorescence microscopy was performed following histological sectioning for an IPN containing a covalently incorporated Rhodamine derivative fluorophore by exciting the sample at 540 nm and detecting at 580 nm (FIGS. 9A and 9B).

Example 12. Magnetic Resonance Imaging of Cartilage-Hydrogel IPN

Figure 10A:
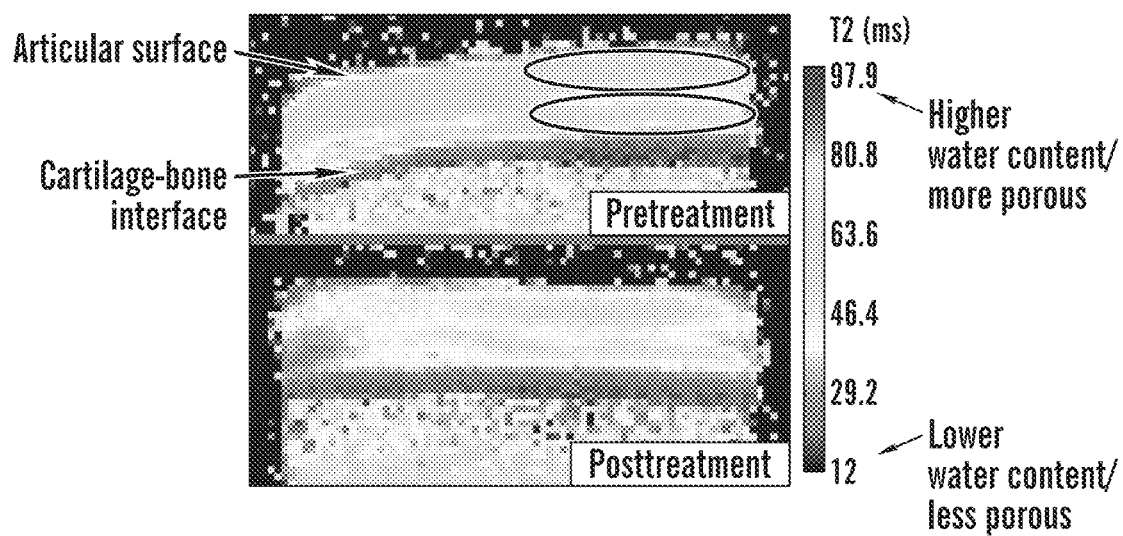
FIG. 10A displays a T2 relaxation map of bovine articular cartilage (pretreatment) and cartilage-polymer IPN (posttreatment).
Figure 10B:
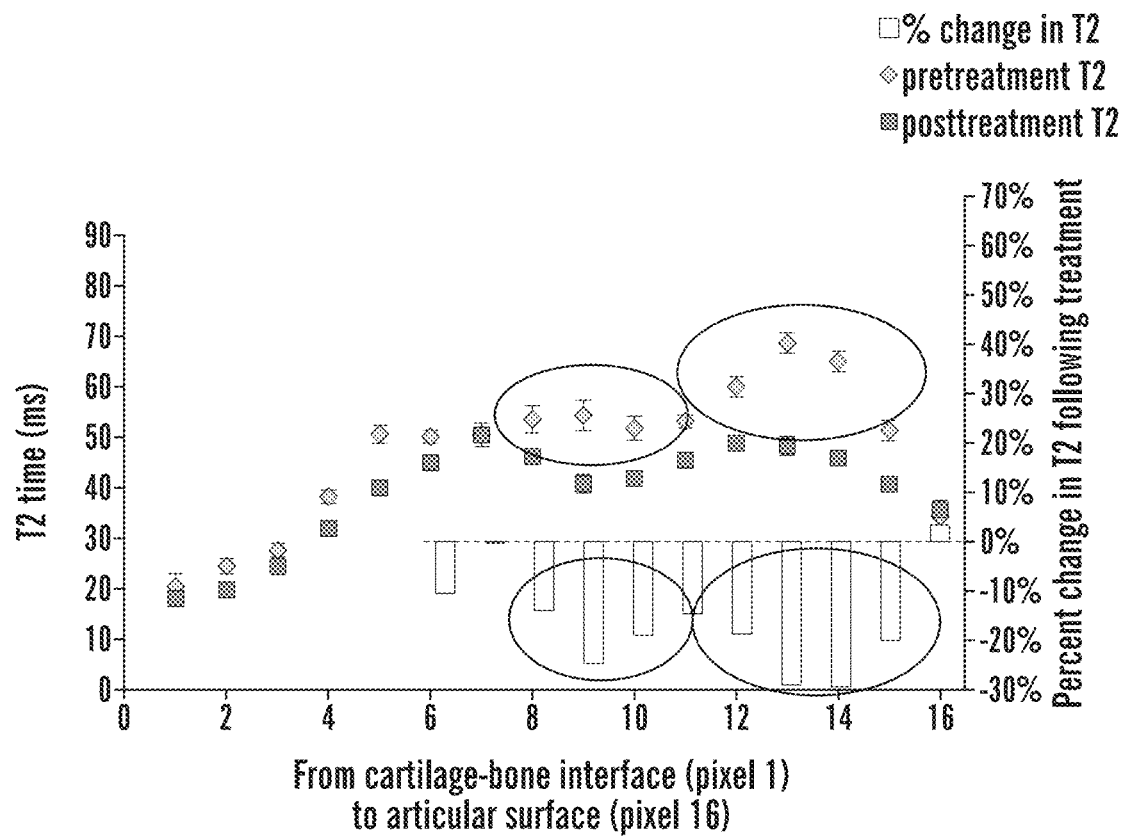
FIG. 10B displays the quantified relaxation times pre- and posttreatment over the region progressing from the cartilage-bone interface to the articular surface. Circled regions in the plot indicate where regions of increased pretreatment relaxation time correspond with the greatest decreases in relaxation time following treatment.

Analysis of an MPC-containing IPN is described as an example. Two nuclei were studied-hydrogen and phosphorus. T2-weighted proton MRI was performed as an indicator of water content or water volume fraction in the polymer-treated tissue. Change in relaxation time following hydrogel IPN treatment was analyzed by this method, and two results were found: 1) water content decreased throughout the tissue following treatment, indicating that the polymer occupies the pores of the cartilage tissue, and 2) regions of the tissue (on the order of several hundred μm in length) with relatively high water content experienced the greatest percent decrease in water content following treatment, indicating that the initially more porous regions (or, those with higher water volume fractions) preferentially experienced a proportionally greater amount of hydrogel incorporation following treatment, while the regions with lesser porosity before treatment received proportionally less hydrogel incorporation following treatment. Phosphorus MRI was used to evaluate the presence of high concentrations of phosphorus due to the phosphate group present on each monomer of pMPC (FIG. 10A). The large increase in phosphorous signal following hydrogel IPN treatment indicates distribution throughout the cartilage depth. An overlay of the T2-weighted and phosphorus image maps reveals greater increases in phosphorus signal coinciding with regions of greater water volume fraction, further indicating the hydrogel's preferentially filling of the most porous regions of tissue (FIG. 10B).

Example 13. Biochemical Analysis of Material Washed Out from Cartilage-Hydrogel IPN Containing MPC Immediately Following Laser Irradiation (for Crosslinking)

Figure 11:
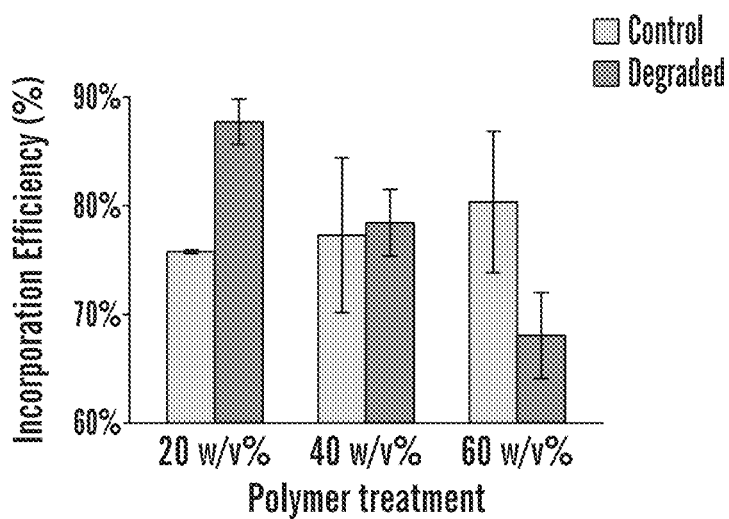
FIG. 11 displays incorporation efficiency of MPC into the cartilage tissue for polymer IPN treatments at 20, 40, and 60 w/v % MPC-based polymer. For each group of columns, from left to right: control, degraded.

Following photocrosslinking as described in Example 1, the osteochondral explant was allowed to incubate in saline for 48 hours. This saline washout solution was passed through a 0.2 μm polytetrafluoroethylene filter and subjected to high performance liquid chromatography. Nonreacted MPC monomer was detected by its distinct absorbance at 208 nm due to its methacrylic double bond. Via construction of a standard curve to obtain the value of the mass of nonreacted MPC monomer, the incorporation efficiency of MPC into the cartilage tissue was obtained by the ratio of incorporated MPC over theoretically incorporated MPC given the volume of the cartilage and assuming a water volume fraction of 80% for bovine articular cartilage, as has been reported previously by others (FIG. 11).

Example 14. Synthesis of Crosslinked MPC Polymer Using Alternate Crosslinker, MPC Concentration, and Crosslinking Density An aqueous solution of MPC (5 w/v %), methylene bisacrylamide (1 mol % of MPC), ammonium persulfate (0.1 mol % of MPC), and tetramethylethylenediamine (0.2 mol % of MPC) was allowed to incubate for 24 hours. Separately, aqueous solutions of MPC (concentrations varying 2, 5, 8, 12 w/v %), ethyleneglycol dimethacrylate (1 mol % of MPC), ammonium persulfate (0.1 mol % of MPC), and tetramethylethylenediamine (0.2 mol % of MPC) were allowed to incubate for 24 hours. Separately, aqueous solutions of MPC (5 w/v %), ethyleneglycol dimethacrylate (varying crosslinking densities of 0, 0.2, 1, 5, 25 mol % of MPC), ammonium persulfate (0.1 mol % of MPC), and tetramethylethylenediamine (0.2 mol % of MPC) were allowed to incubate for 24 hours. The resulting solutions were viscous and lubricious, and there rheological properties were determined (FIGS. 19A-19B, 20A-20B).

Figure 23:
FIG. 23 is a set of photographs of small pieces of cartilage-hydrogel IPN before (left) and after (right) incubation at 37° C. with papain (1 mg/mL) to induce nonspecific cleavage of peptides within the cartilage ECM, allowing for degradation and liberation of cartilage ECM and visualization of the hydrogel component of the cartilage-hydrogel IPN.

Example 15. Visualization of Interpenetrating pMPC Hydrogel Via Enzymatic Degradation of Cartilage Component from Cartilage-Hydrogel IPN Bovine cartilage explants were incubated for 24 hours in the dark in an aqueous solution containing MPC (60 w/v %), ethylene glycol dimethacrylate (1 mol % of MPC), eosin y (0.1 mM), triethanolamine (115 mM), and N-vinyl pyrrolidone (75 mM). The explants were removed from solution, irradiated with a 514 nm argon ion laser (500 mW/cm2, 7.5 min), and rinsed for 2 days in saline to wash out residual non-reacted monomer. The explants were then allowed to incubate for 1 week at 37° C. in a papain solution (1 mg/mL) buffered by sodium phosphate, ethylenediamine tetraacetate, and dithiothreitol, to induce proteolytic cleavage collagen fibrils. Photographs were taken of the cartilage-hydrogel IPNs before and after proteolytic removal of the cartilage component (FIG. 23).

Figure 24:
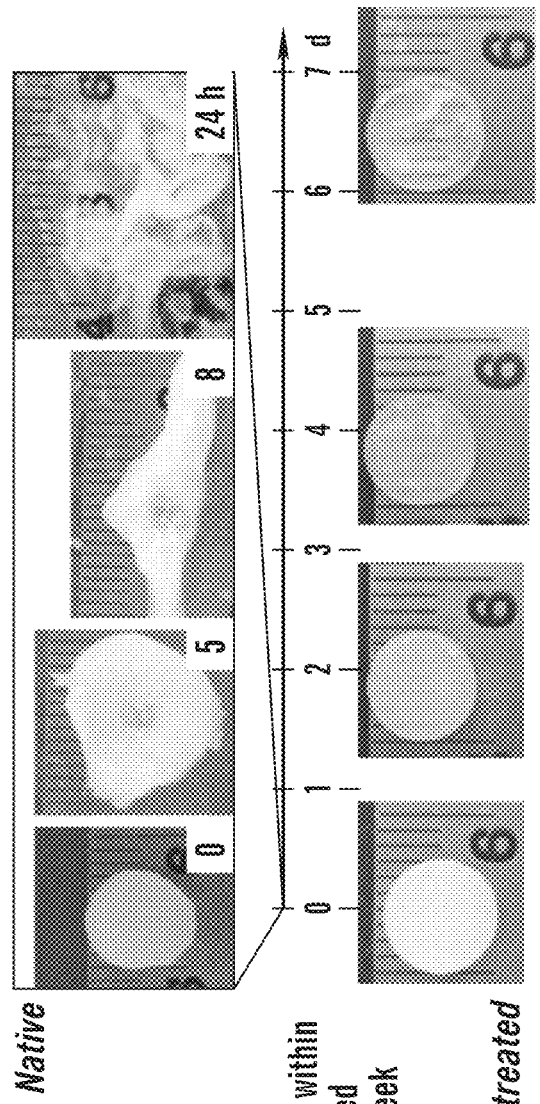
FIG. 24 is a set of photographs of a disc of native articular cartilage degrading upon exposure to papain (1 mg/mL) at 37° C. A hydrogel-treated disc of articular cartilage, i.e. a cartilage-hydrogel IPN, resists degradation and maintains its disc-like shape over 7 days.

Example 16. Observation of Interpenetrating Hydrogel's Ability to Delay Enzymatic Degradation of Cartilage Bovine cartilage explants were incubated for 24 hours in the dark in an aqueous solution containing MPC (60 w/v %), ethylene glycol dimethacrylate (1 mol % of MPC), eosin y (0.1 mM), triethanolamine (115 mM), and N-vinyl pyrrolidone (75 mM). The explants were removed from solution, irradiated with a 514 nm argon ion laser (500 mW/cm2, 7.5 min), and rinsed for 2 days in saline to wash out residual non-reacted monomer. The treated explants along with non-treated cartilage control explants were then allowed to incubate at 37° C. in a papain solution (1 mg/mL) buffered by sodium phosphate, ethylenediamine tetraacetate, and dithiothreitol. Photographs were taken of the cartilage-hydrogel IPNs and of the non-treated control explants periodically over the course of 1 week (FIG. 24). Non-treated cartilage became soft and highly deformable after 5 hours, and was nearly fully dissolved after 24 hours. In contrast, the IPN sample maintained its disc-like shape over 7 days.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. An aqueous solution comprising a polymer, wherein the polymer comprises: (a) monomers of Formula I; and (b) methylenebisacrylamide, wherein Formula I is:

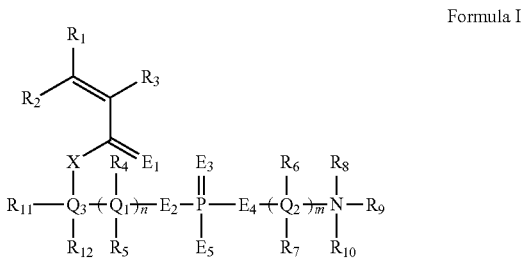

Formula I wherein:
$R_1$, $R_2$, $R_4$, $R_5$, $R_6$, $R_7$, $R_{11}$, and $R_{12}$ are each independently H;
$R_3$, $R_8$, $R_9$, and $R_{10}$ are independently methyl;
X is O;
$Q_1$, $Q_2$, and $Q_3$ are each independently C;
$E_1$, $E_2$, $E_3$, $E_4$, $E_5$ are each independently O;
n is 1;
m is 2; and
wherein the polymer is not a gel or hydrogel.

2. The solution of claim 1, further comprising a second cross-linker.

3. The solution of claim 1, wherein polymer is present in a concentration of less than 10% (w/v).

4. The solution of claim 1, wherein the solution has a viscosity of from about 100 to about $10^6$ centipose.

5. A method of treating a tissue in a subject, the method comprising administering to the subject a solution of claim 1.

* * * * *